(12) United States Patent
Lee

(10) Patent No.: US 9,750,819 B2
(45) Date of Patent: Sep. 5, 2017

(54) LIPID NANOPARTICLE COMPOSITIONS AND METHODS OF MAKING AND METHODS OF USING THE SAME

(71) Applicant: Ohio State Innovation Foundation, Columbus, OH (US)

(72) Inventor: Robert J. Lee, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/403,313

(22) PCT Filed: May 23, 2013

(86) PCT No.: PCT/US2013/042458
§ 371 (c)(1),
(2) Date: Nov. 24, 2014

(87) PCT Pub. No.: WO2013/177419
PCT Pub. Date: Nov. 28, 2013

(65) Prior Publication Data
US 2015/0118288 A1    Apr. 30, 2015

Related U.S. Application Data

(60) Provisional application No. 61/650,729, filed on May 23, 2012, provisional application No. 61/784,892, filed on Mar. 14, 2013.

(51) Int. Cl.
| | |
|---|---|
| *A61K 48/00* | (2006.01) |
| *A61K 9/127* | (2006.01) |
| *C12N 15/113* | (2010.01) |
| *C12N 15/88* | (2006.01) |
| *A61K 47/48* | (2006.01) |
| *A61K 31/713* | (2006.01) |
| *A61K 38/08* | (2006.01) |
| *A61K 38/10* | (2006.01) |
| *A61K 38/48* | (2006.01) |
| *C07K 16/00* | (2006.01) |
| *A61K 31/7088* | (2006.01) |
| *A61K 45/06* | (2006.01) |

(52) U.S. Cl.
CPC ........ *A61K 47/48284* (2013.01); *A61K 9/127* (2013.01); *A61K 9/1271* (2013.01); *A61K 9/1272* (2013.01); *A61K 31/7088* (2013.01); *A61K 31/713* (2013.01); *A61K 38/08* (2013.01); *A61K 38/10* (2013.01); *A61K 38/482* (2013.01); *A61K 45/06* (2013.01); *A61K 47/48046* (2013.01); *A61K 47/48192* (2013.01); *A61K 47/48815* (2013.01); *C07K 16/00* (2013.01); *C12N 15/113* (2013.01); *C12N 15/1135* (2013.01); *C12N 15/1137* (2013.01); *A61K 48/00* (2013.01); *C12N 2310/11* (2013.01); *C12N 2310/14* (2013.01); *C12Y 304/21064* (2013.01)

(58) Field of Classification Search
CPC .... A61K 9/127; A61K 9/1271; A61K 9/1272; A61K 31/7088; A61K 31/713; A61K 47/48046; A61K 47/48815; A61K 48/00; C12N 15/113; C12N 15/1135; C12N 2310/11; C12N 2310/14; C12N 2310/141
See application file for complete search history.

(56) References Cited

U.S. PATENT DOCUMENTS

| | | |
|---|---|---|
| 6,120,798 A | 9/2000 | Allen et al. |
| 7,025,987 B2 | 4/2006 | Cheresh et al. |
| 7,674,767 B2 | 3/2010 | Pai et al. |
| 7,976,868 B2 | 7/2011 | Thorpe |
| 8,067,380 B2 | 11/2011 | Wang et al. |
| 8,222,220 B2 | 7/2012 | Baranova et al. |
| 8,445,021 B2 | 5/2013 | Akhtari et al. |
| 2004/0208921 A1 | 10/2004 | Ho et al. |
| 2007/0135372 A1 | 6/2007 | MacLachlan et al. |
| 2009/0258923 A1* | 10/2009 | Toyobuku ............ A61K 9/1272 514/44 A |
| 2010/0216908 A1 | 8/2010 | Gao et al. |
| 2010/0239654 A1 | 9/2010 | Winter |
| 2011/0038941 A1 | 2/2011 | Lee et al. |
| 2011/0280913 A1 | 11/2011 | Byrd et al. |
| 2012/0058144 A1 | 3/2012 | Manoharan et al. |
| 2012/0183589 A1 | 7/2012 | Rodriguez Gascon et al. |
| 2012/0295832 A1 | 11/2012 | Constien et al. |

FOREIGN PATENT DOCUMENTS

| | | | |
|---|---|---|---|
| WO | WO2005/026372 | * 3/2005 | ............ C12N 15/88 |
| WO | 2009/120247 A2 | 10/2009 | |
| WO | 2011/133504 A2 | 10/2011 | |
| WO | 2011/133868 A2 | 10/2011 | |

(Continued)

OTHER PUBLICATIONS

Simeoni et al., Insight into the mechanism of the peptide-based gene delivery system MPG: implications for delivery of siRNA into mammalian cells. Nucleic Acids Research, 2003, vol. 31, No. 11 2717±2724.*
Roks et al., Synthesis and Characterization of Vesicles Stabilized by Polymerization of Isocyano Functions. Macromolecules 1987, 20, 920-929.*
PCT International Preliminary Report on Patentability, PCT/US2013/042458 filed May 23, 2013, dated Dec. 4, 2014.
PCT International Preliminary Report on Patentability, PCT/US2013/042461 filed May 23, 2013, dated Dec. 4, 2014.
PCT International Search Report and the Written Opinion, PCT/US2013/042461 filed May 23, 2013, dated Dec. 17, 2013.
PCT International Search Report and the Written Opinion, PCT/US2013/042458 filed May 23, 2013, dated Dec. 20, 2013.
Allahverdiyev et al., "Coping with Antibiotic Resistance: Combining Nanoparticles with Antibiotics and Other Antimicrobial Agents", Expert Review of Anti-infective Therapy, 2011, vol. 9, No. 11, pp. 1035-1052.

(Continued)

*Primary Examiner* — Scott Long
*Assistant Examiner* — Arthur S Leonard
(74) *Attorney, Agent, or Firm* — MacMillan, Sobanski & Todd, LLC

(57) ABSTRACT

Lipid nanoparticle formulations, methods of making, and methods of using same are disclosed.

40 Claims, 47 Drawing Sheets
(46 of 47 Drawing Sheet(s) Filed in Color)

(56) References Cited

FOREIGN PATENT DOCUMENTS

WO 2013/177419 A2 11/2013
WO 2013/177421 A2 11/2013

OTHER PUBLICATIONS

Fenske et al., "Liposomal Nanomedicines: An Emerging Field", Toxicologic Pathology, 2008, vol. 36, pp. 21-29.

Huang et al., "Non-Viral Vectors for Gene Therapy", Second Edition: Part I, Advances in Genetics, 2005, vol. 53, Chapters 1-13.

Huang et al., "Targeted Delivery of microRNA-29b by Transferrin-Conjugated Anionic Lipopolyplex Nanoparticles: A Novel Therapeutic Strategy in Acute Myeloid Leukemia", Clinical Cancer Research, 2013, vol. 19, No. 9, pp. 2355-2367.

Jin et al., "Targeted Delivery of Antisense Oligodeoxynucleotide by Transferrin Conjugated pH-sensitive Lipopolyplex Nanoparticles: a Novel Oligonucleotide-based Therapeutic Strategy in Acute Myeloid Leukemia", Molecular Pharmaceutics, 2010, vol. 7, No. 1, pp. 196-206, Abstract Only.

Petersen, "Structurally Modified Polyethylenimines and their Interpolyelectrolyte Complexes with DNA as Non-Viral Gene Delivery Systems", Dissertation, 2002, pp. 1-158.

Piao et al., "Human Serum Albumin-coated Lipid Nanoparticles for Delivery of siRNA to Breast Cancer", Nanomedicine: Nanotechnology, Biology, and Medicine, 2013, vol. 9, pp. 122-129.

Weecharangsan et al., "Efficient Delivery of Antisense Oligodeoxyribonucleotide G3139 by Human Serum Albumin-coasted Liposomes", Molecular Pharmaceutics, 2009, vol. 6, No. 6, pp. 1848-1855.

Wu et al., "Therapeutic Delivery of MicroRNA-29b by Cationic Lipoplexes for Lung Cancer", Molecular Therapy—Nucleic Acids, 2013, vol. 2, No. e84, pp. 1-10.

Yuan et al., "High PEGylation Efficiency of Pentaethylenehexamine-end Poly(ethylene glycol) (mPEG-N6) for Active-ester Surface", Colloids and Surfaces B: Biointerfaces, 2012, vol. 92, pp. 25-29.

Zhang et al., "Lactosylated Gramicidin-based Lipid Nanoparticles (Lac-GLN) for Targeted Delivery of Anti-miR-155 to Hepatocellular Carcinoma", Journal of Controlled Release, 2013, vol. 168, pp. 251-261.

Zhou et al., "Novel Lipoidal Amine-based Nanocarrier Formulations for siRNA Delivery", Therapeutic Delivery, 2012, vol. 3, No. 6, pp. 715-723.

* cited by examiner

| Formulation | Particle size (nm) | Zeta potential | Encapsulation efficiency (%) |
|---|---|---|---|
| GLN | 57.59 ± 2.73 | 14.72 ± 1.15 | 87.5 ± 1.9 |
| Lac-GLN | 72.66 ± 3.14 | 3.49 ± 0.77 | 88.9 ± 2.2 |

Figure 30

LIPID NANOPARTICLE COMPOSITIONS AND METHODS OF MAKING AND METHODS OF USING THE SAME

RELATED APPLICATIONS

This application claims priority to PCT application No. PCT/US2013/043458 filed May 23, 2013 which claims priority to U.S. Provisional Application 61/650,729, filed May 23, 2012, and U.S. Provisional Application 61/784,892, filed Mar. 14, 2013, the disclosures of which are hereby incorporated by reference in their entirety.

STATEMENT REGARDING FEDERALLY SPONSORED RESEARCH

This invention was made with government support under Grant Numbers R01 CA135243, DK088076, and CA152969 awarded by the National Institutes of Health. The government has certain rights in the invention.

SEQUENCE LISTING

The instant application contains a Sequence Listing which has been submitted via EFS-web and is hereby incorporated by reference in its entirety. The ASCII copy, created on May 22, 2013, is named 604_54848_SEQ_LIST_OSU-2013-246.txt, and is 3,490 bytes in size.

TECHNICAL FIELD

The present disclosure pertains to lipid nanoparticles (LNs) usable for the delivery of therapeutic compositions, including, but not limited to nucleic acids (NAs).

BACKGROUND OF THE INVENTION

A liposome is a vesicle composed of one or more lipid bilayers, capable of carrying hydrophilic molecules within an aqueous core or hydrophobic molecules within its lipid bilayer(s). As used herein, "Lipid nanoparticles" (LNs) is a general term to described lipid-based particles in the submicron range. LNs can have structural characteristics of liposomes and/or have alternative non-bilayer types of structures. Drug delivery by LNs via systemic route requires overcoming several physiological barriers. The reticuloendothelial system (RES) is responsible for clearance of LNs from the circulation. Once escaping the vasculature and reaching the target cell, LNs are typically taken up by endocytosis and must release the drug into the cytoplasm prior to degradation within acidic endosome conditions.

In particular, the delivery of such nucleic acids (NAs), including siRNA and other therapeutic oligonucleotides is a major technical challenge that has limited their potential for clinical translation.

The development of efficient delivery vehicles is a key to clinical translation of oligonucleotide (ON) therapeutics. It is desired that a LN formulation should be able to (1) protect the drug from enzymatic degradation; (2) transverse the capillary endothelium; (3) specifically reach the target cell type without causing excessive immunoactivation or off-target cytotoxicity; (4) promote endocytosis and endosomal release; and (5) form a stable formulation with colloidal stability and long shelf-life.

SUMMARY OF THE INVENTION

Provided herein are lipid nanoparticles that can encapsulate therapeutic oligonucleotides with high efficiency and fulfill physical and biological criteria for efficacious delivery. In certain embodiments, the lipid nanoparticles comprise a combination of cationic lipids with tertiary and quaternary amine headgroups. In certain embodiments, the lipid nanoparticles comprise small peptides, such as gramicidin, in addition to lipids. In certain embodiments, the lipid nanoparticles comprise an RNase- or DNase-degrading agent, such as proteinease K. Combinations of these embodiments are further provided. The incorporation of a combination of quaternary and tertiary amine-cationic lipids (QTsome), gramicidin (A, B, C, or D) (SPLN-G), and/or proteinase K (PrKsome) increases the transfection efficiency of lipid nanoparticle formulations.

In a first broad aspect, provided herein is a lipid nanoparticle comprising a combination of tertiary and quaternary amine-cationic lipids. In certain embodiments, the tertiary amine-cationic lipids are chosen from DODAP, DODMA, DC-CHOL, N,N-dimethylhexadecylamine, or combinations thereof. In certain embodiments, the quaternary amine-cationic lipids are selected from DOTAP, DOTMA, DDAB, or combinations thereof. In certain embodiments, the concentration of the tertiary amine-cationic lipids is below 50.0 molar percent of the total lipid content. In certain embodiments, the concentration of quaternary amine-cationic lipids is below 20.0 molar percent of the total lipid content. In particular embodiments, the lipid nanoparticle comprises the lipids DODMA and DOTMA in a molar ratio selected from 45:0, 5:40, 15:30, 22.5:22.5, 30:15, or 40:5. In certain embodiments, the lipid nanoparticle comprises the lipids DMHDA and DOTAP in a molar ratio selected from 90:10, 70:30, 50:50, 30:70, or 10:90.

In certain embodiments, the lipid nanoparticle encapsulates molecules selected from nucleic acids, proteins, polysaccharides, lipids, radioactive substances, therapeutic agents, prodrugs, nutritional supplements, biomarkers, or combinations thereof. In certain embodiments, the encapsulated molecules comprise a nucleic acid selected from plasmid DNAs, antisense oligonucleotides, miRs, anti-miRs, shRNAs, siRNAs, or combinations thereof. In certain embodiments, the encapsulation rate of therapeutic agents or nucleotides is 20% or higher.

In certain embodiments, the lipid nanoparticle further comprises a cationic polymer. In particular embodiments, the cationic polymer is selected from the group consisting of: spermine, dispermine, trispermine, tetraspermine, oligospermine, thermine, spermidine, dispermidine, trispermidine, oligospermidine, putrescine, polylysine, polyarginine, a polyethylenimine of branched or linear type, and polyallylamine.

In certain embodiments, the lipid nanoparticle further comprises a fusogenic peptide.

In certain embodiments, the lipid nanoparticle has a diameter under 300 nm.

In another broad aspect, there is provided herein a lipid nanoparticle having a diameter of less than 300 nm and comprising a peptide. In certain embodiments, the peptide is selected from gramicidin A, B, C, D, or S; JTS-1; proteinase K (PrK); trichorovin-Xlla; rabies virus glycoprotein; interleukin-1β; HIV-Tat; herpes simplex virus VP22 protein; and combinations thereof. In certain embodiments, the peptide comprises an antibiotic. In particular embodiments, the antibiotic is selected from gramicidin A, B, C, D, or S. In particular embodiments, the peptide consists essentially of a lipidated JTS-1 fusogenic peptide. In particular embodiments, the lapidated JTS-1 fusogenic peptide is present at about 0 to about 30 molar percent of the total formulation.

In certain embodiments, the lipid nanoparticle further comprises proteinase K. Proteinase K can be present at from about 0 to about 30 molar percent of the total formulation.

In certain embodiments, the lipid nanoparticle encapsulates molecules selected from nucleic acids, proteins, polysaccharides, lipids, radioactive substances, therapeutic agents, prodrugs, nutritional supplements, biomarkers, or combinations thereof. In certain embodiments, the encapsulated molecules comprise a nucleic acid selected from plasmid DNAs, antisense oligonucleotides, miRs, anti-miRs, shRNAs, siRNAs, or combinations thereof.

In another broad aspect, provided herein is a lipid nanoparticle comprising a DNase- or RNase-degrading agent. In certain embodiments, the DNase- or RNase-degrading agent consists essentially of proteinase K. In certain embodiments, the nanoparticle encapsulates molecules selected from nucleic acids, proteins, polysaccharides, lipids, radioactive substances, therapeutic agents, prodrugs, nutritional supplements, biomarkers, or combinations thereof. In particular embodiments, the encapsulated molecules comprise an oligonucleotide selected from pDNAs, antisense oligonucleotides, miRs, anti-miRs, shRNAs, siRNAs, or combinations thereof. In certain embodiments, the lipid nanoparticle has a diameter under 300 nm.

In another broad aspect, provided herein is a lipid nanoparticle having a diameter of less than 300 nm and comprising a combination of two or more of: a mixture of tertiary and quaternary amine-cationic head groups; an antibiotic; and a DNase or RNase-degrading agent. In certain embodiments, the RNase or RNase-degrading agent consists essentially of proteinase K. In certain embodiments, the antibiotic comprises gramicidin A, B, C, D, or S.

Any of the lipid nanoparticle formulations described herein may comprise a polyethyleneglycol-lipid conjugate. In certain embodiments, the polyethyleneglycol-lipid conjugate selected from polysorbate 80, TPGS, mPEG-DSPE, PEG-DMG. In certain embodiments, the polyethyleneglycol-lipid is present at a concentration less than about 10.0 molar percent. In certain embodiments, the lipid nanoparticle further comprises N,N-dimethylhexadecylamine. In particular embodiments, the N,N-dimethylhexadecylamine is present at a concentration of less than about 60.0 molar percent of the formulation.

In certain embodiments, the lipid nanoparticle further comprises a ligand capable of binding to a target cell or a target molecule. In certain embodiments, the ligand is an antibody or an antibody fragment. In particular embodiments, the ligand is selected from cRGD, galatose-containing moieties, transferrin, folate, low density lipoprotein, or epidermal growth factors.

In another broad aspect, provided herein is a pharmaceutical composition comprising a lipid nanoparticle as described herein and a pharmaceutically acceptable excipient. In certain embodiments, the pharmaceutical composition is administered perorally, intravenously, intraperitoneally, subcutaneously, or transdermally. In certain embodiments, the pharmaceutical composition is prepared as an orally administered tablet, a sterile solution, a sterile suspension, a lyophilized powder, or a suppository.

In another broad aspect, provided herein is a method of diagnosing or treating a cancer or infectious disease. The method comprises administering an effective amount of a pharmaceutical composition as described herein to a patient in need thereof.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 15A shows serum-free; FIG. 15B shows 5% FBS.

FIG. 28A shows particle size and zeta potential of GLN with varying degrees of lactosylation. Each value represented the mean±SD of five measurements. FIG. 28B shows Morphology of anti-miR-155-Lac-GLN by TEM. Scale bar represents 100 nm.

FIG. 29A) Colloidal stability of Lac-GLB. Lac-GLN-anti-miR-155 was stored at 4° C. or 25° C. and particle size was measured over time. Results are the mean of three separate experiments. Error bars stand for standard deviation. FIG. 29B) Serum stability of anti-miR-155-Lac-GLN. Anti-miR-155 alone or anti-miR-155-Lac-GLN were mixed with 50% FBS at 37° C. for 0 hr, 4 hr, and 12 hr. Samples were then analyzed with gel electrophoresis.

FIG. 30: Physicochemical properties of anti-miR-155 containing GLN and Lac-GLN. Value are mean±SD (n=5).

FIG. 32A shows HepG2 cells were treated with GLN or Lac-GLN. FIG. 32B and FIG. 32C show the effect of pre-incubation with 20 mM lactose and 1% BSA on Lac-GLN, respectively. Results are shown in the histogram with the X- and Y-axis indicating the fluorescence intensity and the cell count, respectively.

FIG. 33A) In vitro delivery of Luci-siRNA containing Lac-GLN and other control formulations. SK-HEP-1-cells were transfected with luci-siRNA containing Lac-GLN at the concentration of 100 nM for 4 hr, and luciferase gene expression was evaluated 48 hr post transfection. The results are the mean of four repeats. Error bar stand for standard deviations. FIG. 33B) Cytotoxicity of Lac-GLN from MTS analysis. Results represent the mean±SD. FIG. 33C) In vitro delivery of anti-miR-155 containing Lac-GLN and control formulations. HepG2 cells were transfected with anti-miR-155 containing Lac-GLN at the concentration of 100 nM for 4 hr, and miR-155 expression was evaluated 48 hr after transfection. The results are the mean of three repeats. Error bars stand for standard deviations.

FIG. 34A shows evaluation of different concentrations of anti-miR-155 treatments on miR-155 expression. HepG2 cells were transfected with 100 nM or 200 nM anti-miR-155 containing Lipofectamine2000 and Lac-GLN for 4 hr, and miR-155 expression was evaluated 48 hr after transfection. Values represent the mean±SD (n=3). FIG. 34B shows evaluation of miR-155 targeting gene expressions. C/EBPβ and FOXP3 gene expression were evaluated 48 hr after HepG2 cells were transfected with positive control or Lac-GLN containing 100 nM and 200 nM anti-miR-155. The results are the mean of three repeats. Error bars stand for standard deviations.

FIG. 36A shows liver, lung, and spleen were harvested from C57Bl/6 mice after 4 hr intravenous administration of Cy3-anti-miR-155 containing GLN or Lac-GLN. Cye3 fluorescence signals were visualized on an Olympus FV1000 Filter Confocal Microscope. In FIG. 36A, the red and yellow arrows indicate the uptake of Cy4-anti-miR-155 by hepatocytes and Kupffer cells, respectively.

FIG. 37A shows the expression of miR-155 was analyzed by real time RT-PCR. FIGS. 37B and 37C show the expression of the mir-155 downstream targets, C/EBPβ and FOXP3, were analyzed by real time RT-PCR. Each value represents the mean±SD of three measurements.

DETAILED DESCRIPTION OF THE INVENTION

Figure 1:
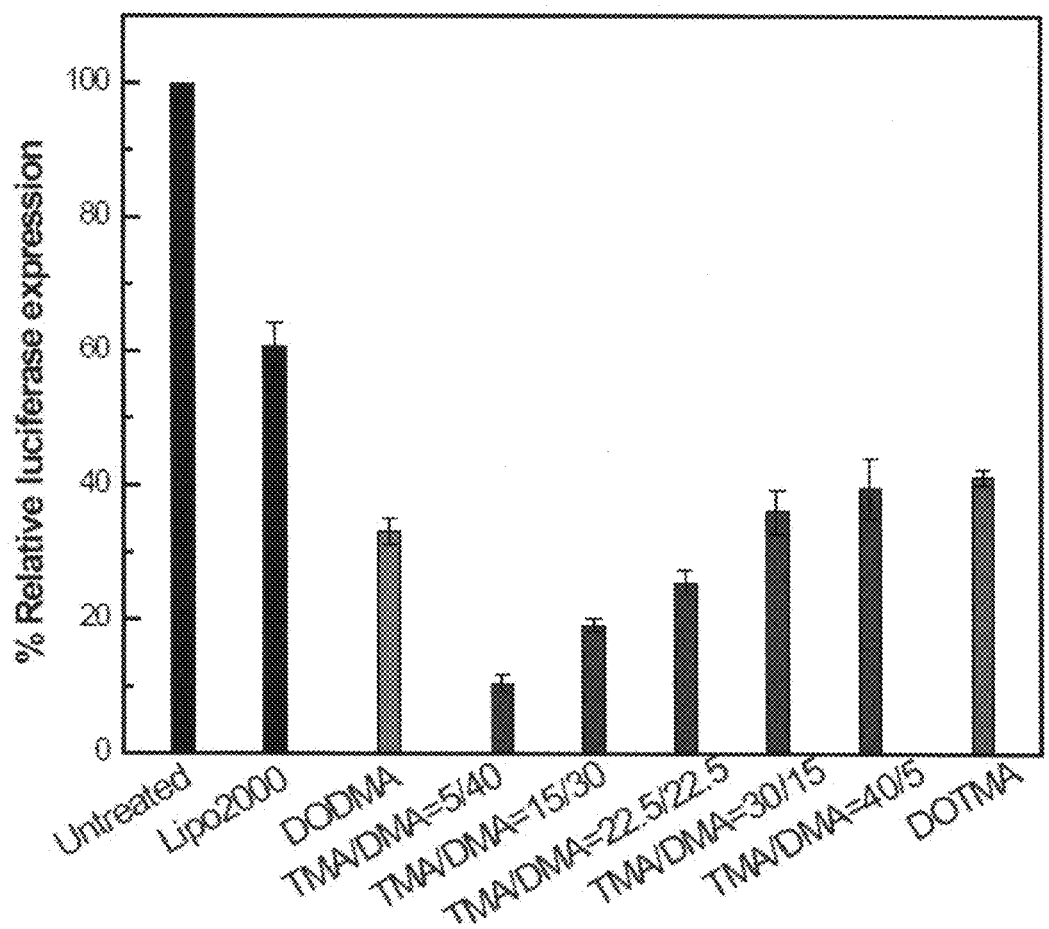
FIG. 1: Downregulation of luciferase expression in SK-HEP-1 cells. Cells expressing luciferase were treated with luciferase-specific siRNA delivered by LNs comprising several different combinations of tertiary amine (DODMA, DMA) and quaternary amine (DOTMA, TMA), (QTsome). Lipofectamine 2000 (Lipo2000) is used as a positive control. Luciferase activity is expressed as a percentage relative to untreated cells.

Various embodiments are described herein in the context of lipid nanoparticles. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

Not all of the routine features of the implementations or processes described herein are shown and described. It will, of course, be appreciated that in the development of any such actual implementation, numerous implementation-specific decisions will be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking for those of ordinary skill in the art having the benefit of this disclosure.

General Description

Nucleic acid (NA)-based therapies are being developed to promote or inhibit gene expression. As mutations in genes and changes in miRNA profile are believed to be the underlying cause of cancer and other diseases, NA-based agents can directly act upon the underlying etiology, maximizing therapeutic potential. Non-limiting examples of NA-based therapies include: plasmid DNA (pDNA), small interfering RNA (siRNA), small hairpin RNA (shRNA), microRNA (miR), mimic (mimetic), anti-miR/antagomiR/miR inhibitor, and antisense oligonucleotide (ASO). Until the development of the nanoparticle compositions described herein, the clinical translation of NA-based therapies faced several obstacles in their implementation since transporting NAs to their intracellular target was particularly challenging and since NAs are relatively unstable and subject to degradation by serum and cellular nucleases. Further, the high negative charges of NAs made it impossible for transport across the cell membrane, further limiting utility.

The LNs described herein provide a useful platform for the delivery of both traditional therapeutic compounds and NA-based therapies. Drugs formulated using LNs provide desirable pharmacokinetic (PK) properties in vivo, such as increased blood circulation time and increased accumulation at the site of solid tumors due to enhanced permeability and retention (EPR) effect. Moreover, in certain embodiments, the LNs may be surface-coated with polyethylene glycol to reduce opsonization of LNs by serum proteins and the resulting RES-mediated uptake, and/or coated with cell-specific ligands to provide targeted drug delivery.

It is desired that the zeta potential of LNs not be excessively positive or negative for systemic delivery. LNs with a highly positive charge tend to interact non-specifically with non-target cells, tissues, and circulating plasma proteins, and may cause cytotoxicity. Alternatively, LNs with a highly negative charge cannot effectively incorporate NAs, which are themselves negatively charged, and may trigger rapid RES-mediated clearance, reducing therapeutic efficacy. LNs with a neutral to moderate charge are best suited for in vivo drug and gene delivery.

Provided herein are lipid nanoparticles (LNs) with improved transfection activity. The lipid nanoparticles may either partition hydrophobic molecules within the lipid membrane or encapsulate water-soluble particles or molecules within the aqueous core. In certain embodiments, the LN formulations comprise a mixture of lipids, generally including a charged lipid and a neutral lipid, and optionally further including a PEGylating lipid and/or cholesterol. The LN formulations of the present disclosure may comprise combinations of quaternary and tertiary amines, peptides such as gramicidin (A, B, C, D, or S), or RNase- or DNase-degrading agents such as proteinase K. In certain embodiments, the lipid nanoparticles are produced by combining cationic lipids with quaternary amine headgroups and cationic lipids with tertiary amine headgroups. In certain embodiment, the lipid nanoparticles are small peptidic lipid nanoparticles (SPLN) and comprise a peptide such as gramicidin or JTS1. In certain embodiments, the lipid nanoparticles are coated with proteinase K, which enhances transfection in the presence of serum. For ease of reference, the SPLNs comprising gramicin are referred to herein as SPLN-Gs, the SPLNs comprising JTS-1 peptide are referred to herein as SPLN-J, and the lipid nanoparticles comprising proteinase K are referred to herein as PrKsomes. Combinations of these different embodiments are further provided. The LNs have a diameter of less than 300 nm, or in particular embodiments between about 50 and about 200 nm. These LNs show enhanced transfection and reduced cytotoxicity, especially under high serum conditions found during systemic administration. The LNs are applicable to a wide range of current therapeutic agents and systems, serum stability, and targeted delivery, with high transfection efficiency.

The term "lipid nanoparticle" as used herein refers to any vesicles formed by one or more lipid components. The LN formulations described herein may include cationic lipids. Cationic lipids are lipids that carry a net positive charge at any physiological pH. The positive charge is used for association with negatively charged therapeutics such as ASOs via electrostatic interaction.

Suitable cationic lipids include, but are not limited to: 3β-[N—(N',N'-dimethylaminoethane)-carbamoyl]cholesterol hydrochloride (DC-Chol); 1,2-dioleoyl-3-trimethylammonium-propane (DOTAP); 1,2-dioleoyl-3-dimethylammonium-propane (DODAP); dimethyldioctadecylammonium bromide salt (DDAB); 1,2-dilauroyl-sn-glycero-3-ethylphosphocholine chloride (DL-EPC); N-[1-(2,3-dioleyloyx) propyl]-N—N—N-trimethyl ammonium chloride (DOTMA); N-[1-(2,3-dioleyloyx) propyl]-N—N—N-dimethyl ammonium chloride (DODMA); N,N-dioctadecyl-N,N-dimethylammonium chloride (DODAC); N-(1-(2,3-dioleyloxyl)propyl)-N-2-(sperminecarboxamido)ethyl)-N,N-dimethylammonium trifluoracetate (DOSPA); 1,2-dimyristyloxypropyl-3-dimethylhydroxyethyl ammonium bromide (DMRIE); dioctadecylamidoglycylspermine (DOGS); neutral lipids conjugated to cationic modifying groups; and combinations thereof. In addition, a number of cationic lipids in available preparations could be used, such as LIPOFECTIN® (from GIBCO/BRL), LIPOFECTAMINE® (from GIBCO/MRL), siPORT NEOFX® (from Applied Biosystems), TRANSFECTAM® (from Promega), and TRANSFECTIN® (from Bio-Rad Laboratories, Inc.). The skilled practitioner will recognize that many more cationic lipids are suitable for inclusion in the LN formulations. The cationic lipids of the present disclosure may be present at concentrations ranging from about 0 to about 80.0 molar percent of the lipids in the formulation, or from about 5.0 to about 50.0 molar percent of the formulation.

In certain embodiments, the LN formulations presently disclosed may also include anionic lipids. Anionic lipids are lipids that carry a net negative charge at physiological pH. These anionic lipids, when combined with cationic lipids, are useful to reduce the overall surface charge of LNs and introduce pH-dependent disruption of the LN bilayer structure, facilitating nucleotide release by inducing nonlamellar phases at acidic pH or induce fusion with the cellular membrane.

Examples of suitable anionic lipids include, but are not limited to: fatty acids such as oleic, linoleic, and linolenic acids; cholesteryl hemisuccinate; 1,2-di-O-tetradecyl-sn-glycero-3-phospho-(1'-rac-glycerol) (Diether PG); 1,2-dimyristoyl-sn-glycero-3-phospho-(1'-rac-glycerol) (sodium salt); 1,2-dimyristoyl-sn-glycero-3-phospho-L-serine (sodium salt); 1-hexadecanoyl,2-(9Z,12Z)-octadecadienoyl-sn-glycero-3-phosphate; 1,2-dioleoyl-sn-glycero-3-[phospho-rac-(1-glycerol)] (DOPG); dioleoylphosphatidic acid (DOPA); and 1,2-dioleoyl-sn-glycero-3-phospho-L-serine (DOPS); anionic modifying groups conjugated to neutral lipids; and combinations thereof. The anionic lipids of the present disclosure are present at concentrations up to about 60.0 molar percent of the formulation, or from about 5.0 to about 25.0 molar percent of the formulation.

In certain embodiments, charged LNs are advantageous for transfection, but off-target effects such as cytotoxicity and RES-mediated uptake may occur. Hydrophilic molecules such as polyethylene glycol (PEG) may be conjugated to a lipid anchor and included in the LNs described herein to discourage LN aggregation or interaction with membranes. Hydrophilic polymers may be covalently bonded to lipid components or conjugated using crosslinking agents to functional groups such as amines.

Suitable conjugates of hydrophilic polymers include, but are not limited to: polyvinyl alcohol (PVA); polysorbate 80; 1,2-distearoyl-sn-glycero-3-phosphoethanolamine-N-PEG2000 (DSPE-PEG2000); D-alpha-tocopheryl polyethylene glycol 1000 succinate (TPGS); dimyristoylphosphatidylethanolamine-PEG2000 (DMPE-PEG2000); and dipalmitoylphosphatidlyethanolamine-PEG2000 (DPPE-PEG2000). The hydrophilic polymer may be present at concentrations ranging from about 0 to about 15.0 molar percent of the formulation, or from about 5.0 to about 10.0 molar percent of the formulation. The molecular weight of the PEG used is between about 100 and about 10,000 Da, or from about 100 to about 2,000 Da.

The LNs described herein may further comprise neutral and/or amphipathic lipids as helper lipids. These lipids are used to stabilize the formulation, reduce elimination in vivo, or increase transfection efficiency. The LNs may be formulated in a solution of saccharides such as, but not limited to, glucose, sorbitol, sucrose, maltose, trehalose, lactose, cellubiose, raffinose, maltotriose, dextran, or combinations thereof, to promote lyostability and cryostability.

Neutral lipids have zero net charge at physiological pH. One or a combination of several neutral lipids may be included in any LN formulation disclosed herein.

Suitable neutral lipids include, but are not limited to: phosphatidylcholine (PC), phosphatidylethanolamine, ceramide, cerebrosides, sphingomyelin, cephalin, cholesterol, diacylglycerols, glycosylated diacylglycerols, prenols, lysosomal PLA2 substrates, N-acylglycines, and combinations thereof.

Other suitable lipids include, but are not limited to: phosphatidylcholine, phosphatidic acid, phosphatidylethanolamine, phosphatidylglycerol, phosphatidylcholine, and lysophosphatidylethanolamine; sterols such as cholesterol, demosterol, sitosterol, zymosterol, diosgenin, lanostenol, stigmasterol, lathosterol, and dehydroepiandrosterone; and sphingolipids such as sphingosines, ceramides, sphingomyelin, gangliosides, glycosphingolipids, phosphosphingolipids, phytoshingosine; and combinations thereof.

The LN formulations described herein may further comprise fusogenic lipids or fusogenic coatings to promote membrane fusion. Examples of suitable fusogenic lipids include, but are not limited to, glyceryl mono-oleate, oleic acid, palmitoleic acid, phosphatidic acid, phosphoinositol 4,5-bisphosphate ($PIP_2$), and combinations thereof.

The LN formulations described herein may further comprise cationic lipids. The headgroups of such lipids may be primary, secondary, tertiary, or quaternary amines in nature. In certain embodiments, the LNs comprise a mixture of tertiary and quaternary amines.

Suitable tertiary aminolipids include, but are not limited to: DODAP; DODMA; N,N-dimethylhexadecylamine (DMHDA); and DC-CHOL. Suitable quaternary aminolipids include, but are not limited to: DOTAP, DOTMA, and DDAB. Combinations of multiple aminolipids, particularly of tertiary and quaternary cationic lipids, are beneficial towards LN delivery of therapeutic agents. Cationic lipids may be present in concentrations up to about 60 molar percent combined.

The LN formulations described here may further comprise cationic polymers or conjugates of cationic polymers. Cationic polymers or conjugates thereof may be used alone or in combination with lipid nanocarriers.

Suitable cationic polymers include, but are not limited to: polyethylenimine (PEI); pentaethylenehexamine (PEHA); spermine; spermidine; poly(L-lysine); poly(amido amine) (PAMAM) dendrimers; polypropyleneiminie dendrimers; poly(2-dimethylamino ethyl)-methacrylate (pDMAEMA); chitosan; tris(2-aminoethyl)amine and its methylated derivatives; and combinations thereof. Chain length and branching are important considerations for the implementation of polymeric delivery systems. High molecular weight polymers such as PEI (MW 25,000) are used as transfection agents, but suffer from cytotoxicity. Low molecular weight PEI (MW 600) does not cause cytotoxicity, but is limited due to its inability to facilitate stable condensation with nucleic acids.

Anionic polymers may be incorporated into the LN formulations presently disclosed as well. Suitable anionic polymers include, but are not limited to: poly(propylacrylic acid) (PPAA); poly(glutamic acid) (PGA); alginates; dextrans; xanthans; derivatized polymers; and combinations thereof.

In certain embodiments, the LN formulation includes conjugates of polymers. The conjugates may be crosslinked to targeting agents, lipophilic moieties, peptides, proteins, or other molecules that increase the overall therapeutic efficacy.

Suitable crosslinking agents include, but are not limited to: N-succinimidyl 3-[2-pyridyldithio]-propionate (SPDP); dimethyl 3,3'-dithiobispropionimidate (DTBP); dicyclohexylcarbodiimide (DCC); diisopropyl carbodiimide (DIC); 1-ethyl-3-[3-dimethylaminopropyl]carbodiimide (EDC); N-hydroxysulfosuccinimide (Sulfo-NHS); N'—N'-carbonyldiimidazole (CDI); N-ethyl-5-phenylisoxazolium-3'sulfonate (Woodward's reagent K); and combinations thereof.

The LN formulations may further comprise peptides and/or proteins. Peptides and proteins, especially those derived from bacteria and viruses or used as antibiotic agents, may aid in membrane permeation. The peptides or proteins may be directly mixed with lipids, covalently attached, or conjugated to lipid moieties with crosslinking agents.

Suitable peptides and proteins include, but are not limited to: gramicidin A, B, C, D, and S; HA2; JTS-1; proteinase K (PrK); trichorovin-Xlla (TV-Xlla); rabies virus glycoprotein (RVG); interleukin-1β; HIV-Tat; herpes simplex virus (HSV) VP22 protein; and combinations thereof. In certain embodiments, JTS-1 and/or gramicidin is used at about 0 to about 40 molar percent. In certain embodiments, PrK at a concentration of about 0 to about 30 molar percent is applied by direct mixing with oligonucleotide or conjugation to hexadecyl isothiocyanate for LN surface coating of PrK.

The addition of targeting agents to the LN provides increased efficacy over passive targeting approaches. Targeting involves incorporation of specific targeting moieties such as, but not limited to, ligands or antibodies against cell surface receptors, peptides, lipoproteins, glycoproteins, hormones, vitamins, antibodies, antibody fragments, prodrugs, and conjugates or combinations of these moieties.

In certain embodiments, maximization of targeting efficiency includes the surface coating of the LN with the appropriate targeting moiety rather than encapsulation of the targeting agent. This method optimizes interaction with cell surface receptors.

It is to be understood that targeting agents may be either directly incorporated into the LN during synthesis or added in a subsequent step. Functional groups on the targeting moiety as well as specifications of the therapeutic application (e.g., degradable linkage) dictate the appropriate means of incorporation into the LN. Targeting moieties that do not have lipophilic regions cannot insert into the lipid bilayer of the LN directly and require prior conjugation to lipids before insertion or must form an electrostatic complex with the LNs.

Also, under certain circumstances, a targeting ligand cannot directly bind to a lipophilic anchor. In these circumstances, a molecular bridge in the form of a crosslinking agent may be utilized to facilitate the interaction. In certain embodiments, it is advantageous to use a crosslinking agent if steric restrictions of the anchored targeting moiety prevent sufficient interaction with the intended physiological target. Additionally, if the targeting moiety is only functional under certain orientations (e.g., monoclonal antibody), linking to a lipid anchor via crosslinking agent is beneficial. Traditional methods of bioconjugation may be used to link targeting agents to LNs. Reducible or hydrolysable linkages may be applied to prevent accumulation of the formulation in vivo and subsequent cytotoxicity.

Various methods of LN preparation are suitable to synthesize the LNs of the present disclosure. For example, ethanol dilution, freeze-thaw, thin film hydration, sonication, extrusion, high pressure homogenization, detergent dialysis, microfluidization, tangential flow diafiltration, sterile filtration, and/or lyophilization may be utilized. Additionally, several methods may be employed to decrease the size of the LNs. For example, homogenization may be conducted on any devices suitable for lipid homogenization such as an Avestin Emulsiflex C5® device. Extrusion may be conducted on a Lipex Biomembrane extruder using a polycarbonate membrane of appropriate pore size (0.05 to 0.2 μm). Multiple particle size reduction cycles may be conducted to minimize size variation within the sample. The resultant LNs may then be passed through a size exclusion column such as Sepharose CL4B or processed by tangential flow diafiltration to purify the LNs.

Any embodiment of the LNs described herein may further include ethanol in the preparation process. The incorporation of about 30-50% ethanol in LN formulations destabilizes the lipid bilayer and promotes electrostatic interactions among charged moieties such as cationic lipids with anionic ASO and siRNA. LNs prepared in high ethanol solution are diluted before administration. Alternatively, ethanol may be removed by dialysis, or diafiltration, which also removes non-encapsulated NA.

In certain embodiment, it is desirable that the LNs be sterilized. This may be achieved by passing of the LNs through a 0.2 or 0.22 μm sterile filter with or without pre-filtration.

Physical characterization of the LNs can be carried through many methods. Dynamic light scattering (DLS) or atomic force microscopy (AFM) can be used to determine the average diameter and its standard deviation. In certain embodiments, it is especially desirable that the LNs have about a 200 nm diameter. Zeta potential measurement via zeta potentiometer is useful in determining the relative stability of particles. Both dynamic light scattering analysis and zeta potential analysis may be conducted with diluted samples in deionized water or appropriate buffer solution. Cryogenic transmission electron microscopy (Cryo-TEM) and scanning electron microscopy (SEM) may be used to determine the detailed morphology of LNs.

The LNs described herein are stable under refrigeration for several months. LNs requiring extended periods of time between synthesis and administration may be lyophilized using standard procedures. A cryoprotectant such as 10% sucrose may be added to the LN suspension prior to freezing to maintain the integrity of the formulation. Freeze drying loaded LN formulations is recommended for long term stability.

Quaternary and Tertiary Amine-Cationic Lipids (QTsome)

While the physical characteristics of LNs promote enhanced permeation and retention (EPR) in the fenestrated tumor vasculature, endosomal escape remains a challenge for conventional LN formulations. To this end, lipid nanoparticles comprising positively charged quaternary or tertiary amine-based cationic lipids for the complexation of nucleic acids have been developed. Quaternary amine-based cationic lipids carry a permanent positive charge and are capable of forming stable electrostatic complexes with nucleic acids. Tertiary amine-cationic lipids, however, are conditionally ioniziable and their positive charge is largely regulated by pH. Provided herein are LNs comprising a combination of quaternary and tertiary amine-cationic lipids (QTsomes), which provides a mechanism by which therapeutic agents may be released from LNs within the endosome. QTsomes are conditionally ionizable and facilitate disruption of the lipid bilayer and oligonucleotide endosomal release under the acidic conditions of the endosome. Quaternary amino-catinoic lipids are permanently charged, ensuring strong interaction between the lipids and the oligonucleotide, thereby ensuring stability. The combination of tertiary and quaternary cationic lipids provides an optimum pH response profile that is not possible with each class of lipid individually. QTsomes are more active than regular cationic liposomes in transfecting cells.

QTsomes demonstrate greater transfection activity than standard cationic lipid formulations. Fine tuning the balance between quaternary and tertiary amine-cationic lipids allows for the precise controlled release of nucleic acids into the cytosol. In a particular embodiment, the use of particular release parameters provides a technique whereby the activity of nucleic acid-based therapeutics can be maximized. For example, it is noted that tertiary amine-cationic lipids have pH-dependent ionization profiles when used alone. Since a single lipid species may not provide a desired level of control of LN charge characteristics, a combination of a tertiary and a quaternary amine-cationic lipid can be used, thus resulting in significantly improved activity of such combinations in siRNA delivery.

Figure 20:
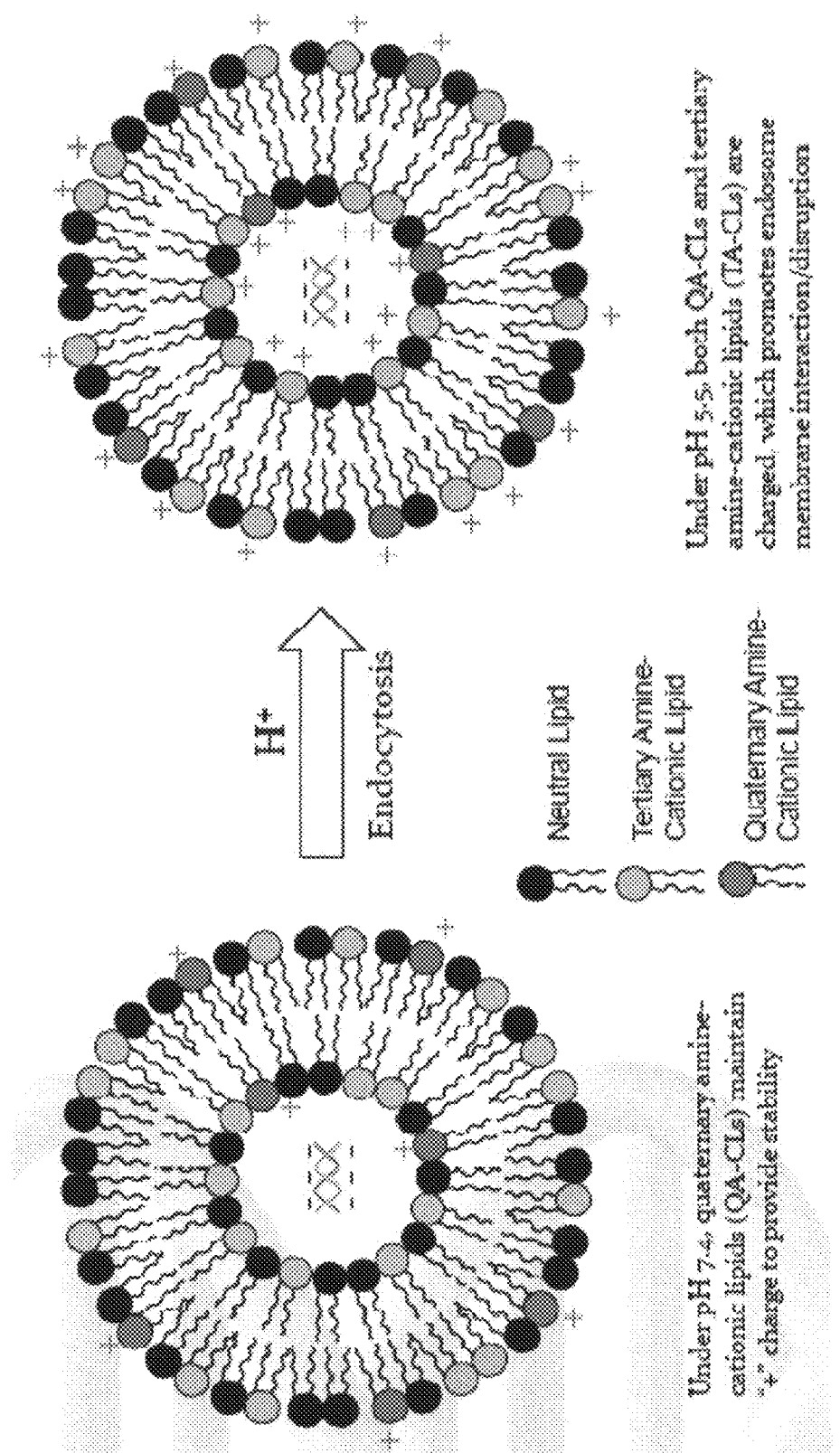
FIG. 20: QTsome mechanism of action.

FIG. 1 depicts the relative luciferase expression of combinations of tertiary and quaternary cationic lipids. At a Q-to-T amine-cationic lipid ratio of 5:40, over 85% down-regulation is demonstrated for luciferase siRNA transfection in HCC cells expressing luciferase. FIG. 20 depicts the QTsome mechanism of action. Under pH 7.4, quaternary amine-cationic lipids (QA-CLs) maintain "+" charge to provide stability. Under pH 5.5, both QA-CLs and tertiary amine-cationic lipids (TA-CLs) are charged, which promotes endosome membrane interaction/disruption.

Small Peptidic Lipid Nanoparticles (SPLN)

Further provided herein are LNs comprising that are small peptidic lipid nanoparticles (SPLNs). In certain embodiments, the SPLNs comprise the antibiotic gramicidin. Described herein are certain variants of gramicidin (A, B, C, D) that have not previously been investigated as transfection agents. Though these gramicidin subtypes share a conserved sequence of peptides with gramicidine S, gramicidin A, B, C, and D form a beta-helix structure while gramicidin forms a cyclic structure. Therefore, gramicidins A-D are different from gramicidin S. Gramicidins dimerize and form an ionophore and promote membrane fusion, which promotes destabilization of the lipid bilayers of the endosome and the LN. Consequently, SPLNs comprising gramicidin are ideal in nucleic acid-based therapies. Incorporation of gramicidin A, B, C, D, or S into LNs significantly increases the cellular transfection efficiency of ASO and siRNA.

Figure 21:
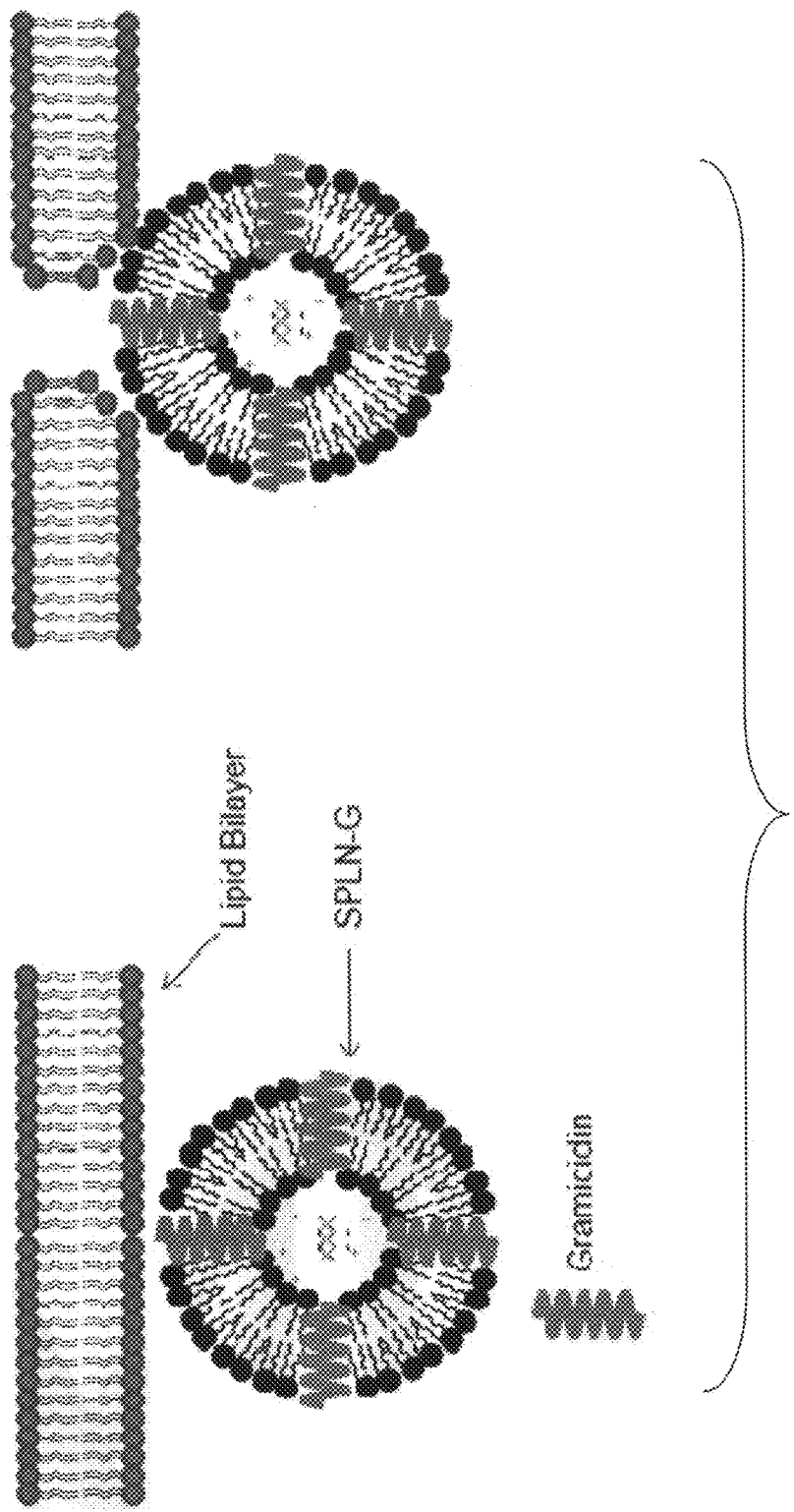
FIG. 21: Depiction of SPLN-Gs.
Figure 22:
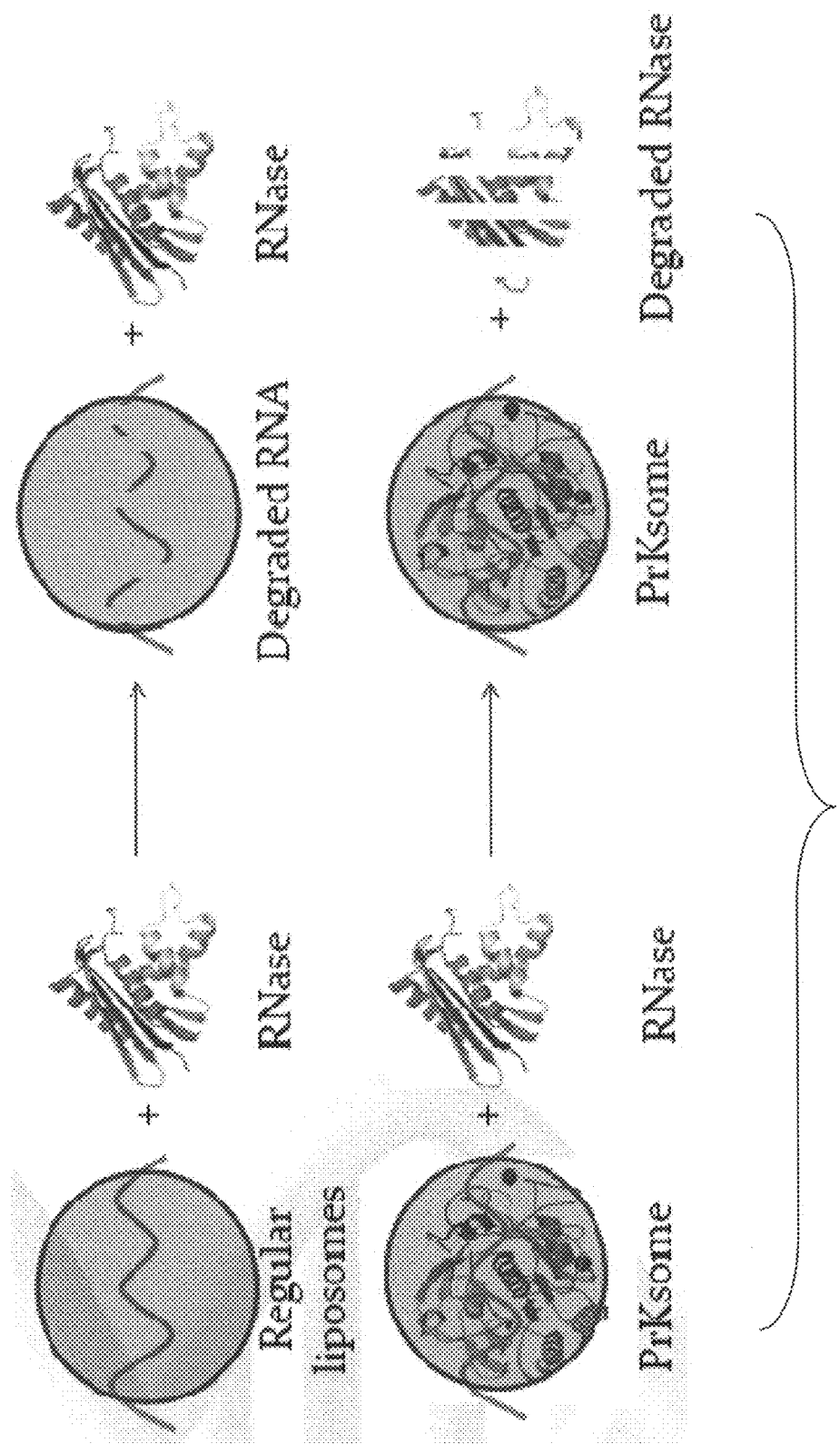
FIG. 22: The proteinase K coating protects oligonucleotides from DNase and RNase present in serum.

In certain embodiments, SPLNs utilizing gramicidin are designated SPLN-G, followed by a number corresponding to the molar percentage of gramicidin in the formulation. FIG. 21 depicts SPLN-Gs.

Figure 5:
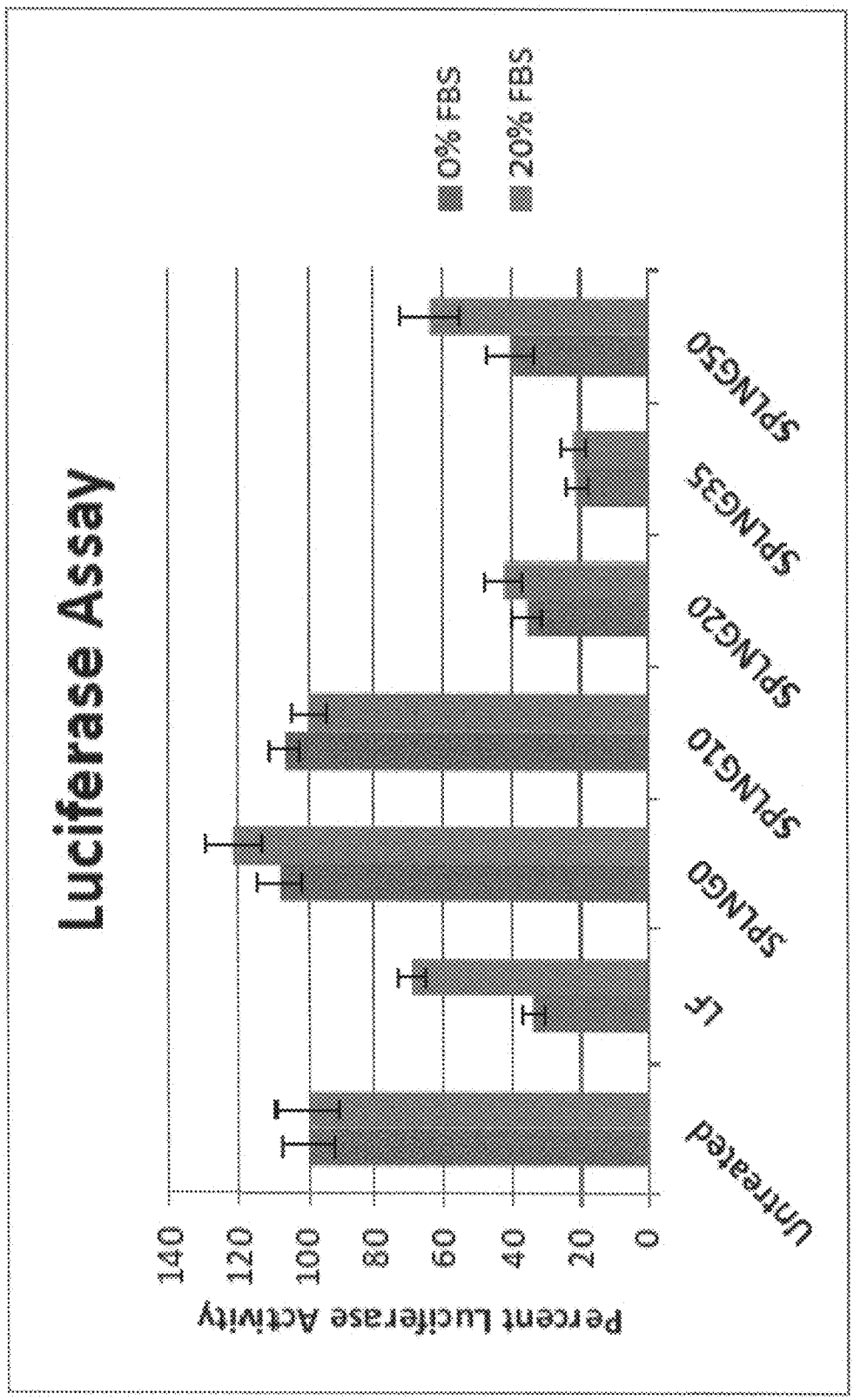
FIG. 5: Downregulation of luciferase expression in SK-HEP-1 cells by luciferase-siRNA delivered using SPLN-G. Lipofectamine 2000 (Lipo2000) is used as a positive control. Luciferase activity is expressed as a percentage relative to untreated cells.

Combining gramicidin A, B, C, D, or S into lipid nanoparticle formulations increases the transfection efficiency of ASO and siRNA formulations in the presence of serum. The gramicidin assists permeabilization of endosome membrane bilayers to ODNs. In contrast, transfection agents such as Lipofectamine™ 2000 show markedly diminished transfection activity in the presence of serum. SPLN-G with luciferase siRNA demonstrates low cytotoxicity and greater transfection activity than the transfection agent Lipofectamine 2000 (LF) in the presence of serum in HCC cells, as shown in FIG. 5. Lipid nanoparticle formulations that do not show reduction in transfection activity in the presence of serum are advantageous as serum conditions best simulate those in the actual patient, thus facilitating a better translation into clinical study.

Further provided herein are SPLNs incorporating lapidated JTS-1 fusogenic peptide. These SPLN-J particles show high transfection activity, and have a high membrane fusion activity that is triggered by pH-dependent conformational change of JTS-1 from a coil to a helix.

Proteinase K (PrK) (PrKsome)

Figure 23:
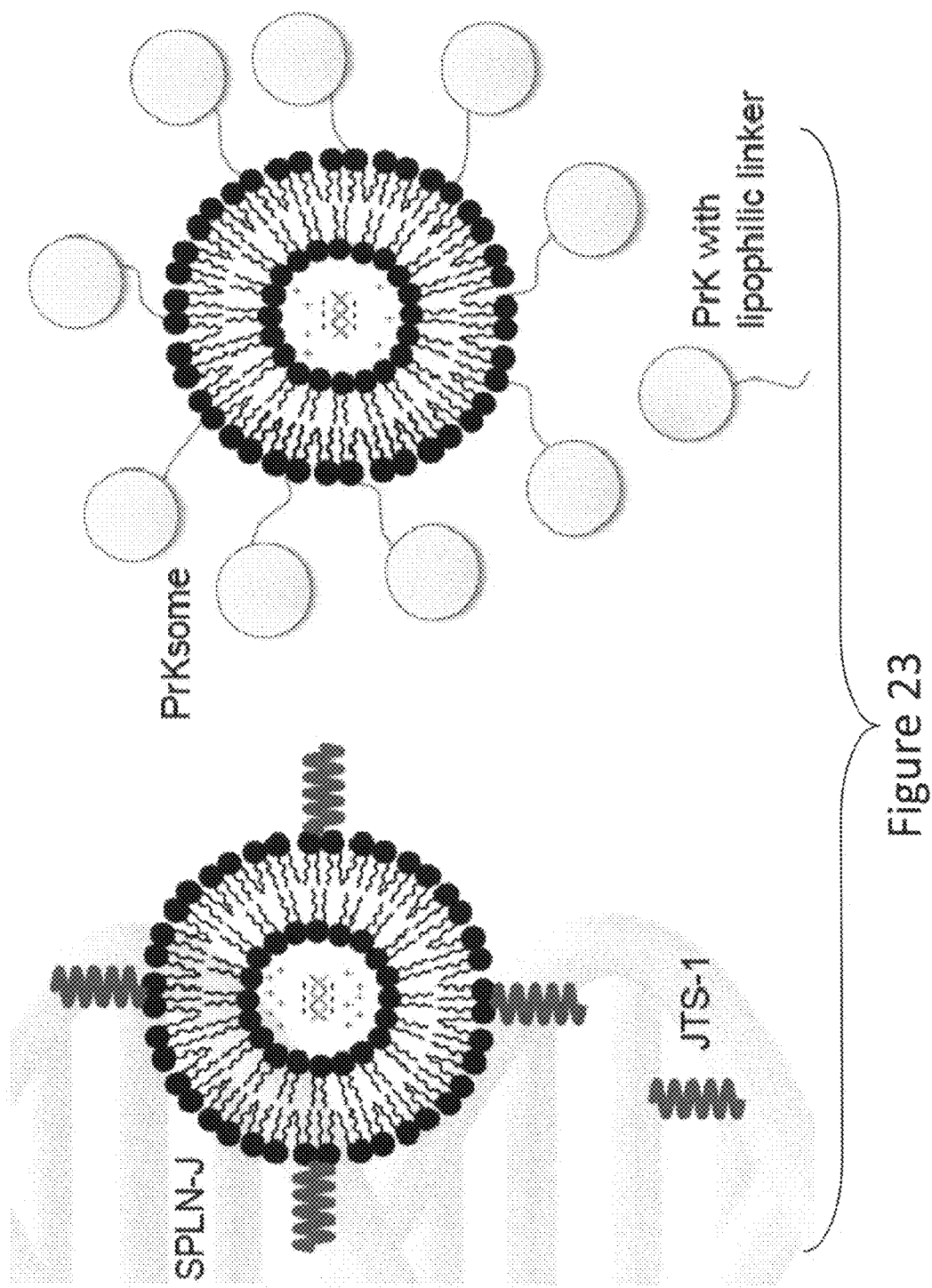
FIG. 23: Diagrams of SPLN-J with the JTS-1 fusogenic peptide and a LN with proteinase K coating.

Degradation of nucleotides in serum after administration is a perpetual concern for nucleic acid-based therapies, even those involving lipid or polymer carriers. Often, alterations to the nucleotide, such as backbone and base pair modifications, are conducted to better protect the nucleotide against degradation. However, these modifications may result in reduced or off-target activity of the drug. In order to overcome this problem, provided herein are lipid nanoparticle formulations comprising a DNase- or RNase-degrading agent. In particular embodiments, the DNase- or RNase-degrading agent is proteinase K (PrK). The proteinase K coating protects oligonucleotides from DNase and RNase present in serum. This is depicted by FIG. 23. Proteinase K is able to protect siRNA better than lipid nanoparticles without proteinase K. Inclusion of proteinase K increases transfection efficiency in the presence of serum without significant cytotoxicity in KB cells. PrKsomes are highly versatile and applicable to both natural and chemically modified oligonucleotides.

Figure 24:
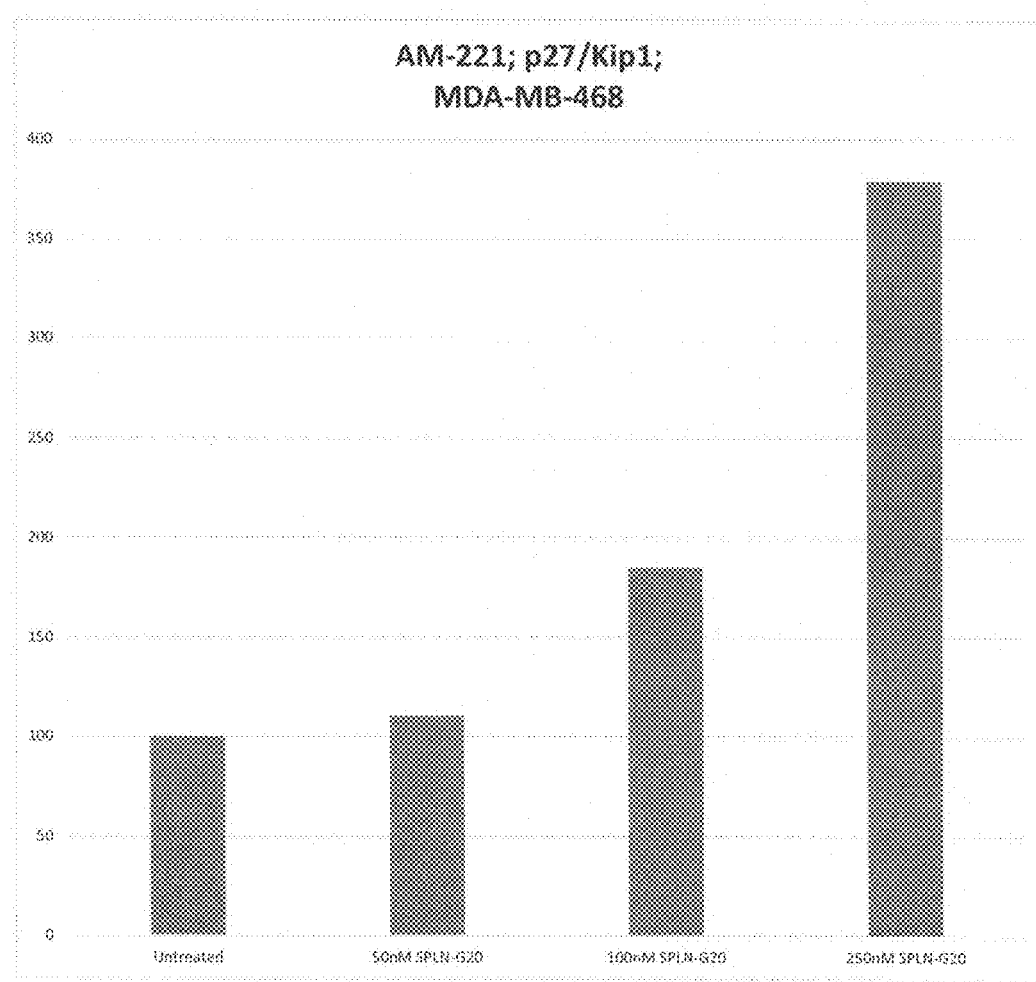
FIG. 24: Upregulation of p27/kip1 mRNA by SPLN-G20 loaded with anti-miR-221 in MDA-MB-468 breast cancer cells. This shows that SPLN-G20 is an effective vehicle for delivery of anti-miRs. P27/Kip1 are targets of miR-221. This upregulation indicates inhibition of miR-221 function.

Proteinase K coatings can be incorporated into any embodiment of LNs described here. By way of non-limiting example, FIG. 24 depicts a SPLN-J with a proteinase K coating.

Applications

Depending on the application, the lipid nanoparticles disclosed herein may be designed to favor characteristics such as increased interaction with nucleic acids, increased serum stability, lower RES-mediated uptake, targeted delivery, or pH sensitive release within the endosome. Because of the varied nature of LN formulations, any one of the several methods provided herein may be applied to achieve a particular therapeutic aim. Cationic lipids, anionic lipids, PEG-lipids, neutral lipids, fusogenic lipids, aminolipids, cationic polymers, anionic polymers, polymer conjugates, peptides, targeting moieties, and combinations thereof may be applied to meet specific aims.

The lipid nanoparticles described herein can be used as platforms for therapeutic delivery of oligonucleotide (ON) therapeutics, such as siRNA, shRNA, miRNA, anti-miR, and antisense ODN. These therapeutics are useful to manage a wide variety of diseases such as various types of cancers, leukemias, viral infections, and other diseases. For instance, targeting moieties such as cyclic-RGD, folate, transferrin, or antibodies greatly enhance activity by enabling targeted drug delivery. A number of tumors overexpress receptors on their cell surface. Non-limiting examples of suitable targeting moieties include transferrin (Tf), folate, low density lipoprotein (LDL), and epidermal growth factors. In addition, tumor vascular endothelium markers such as alpha-v-beta-3 integrin and prostate-specific membrane antigen (PSMA) are valuable as targets for targeted LNs. In certain embodiments, LN formulations having particles measuring about 300 nm or less in diameter with a zeta potential of less than 50 mV and an encapsulation efficiency of greater than 20.0% are useful for NA delivery.

Implementation of embodiments of the LN formulations described herein alone or in combination with one another synergizes with current paradigms of lipid nanoparticle design.

A wide spectrum of therapeutic agents may be used in conjunction with the LNs described herein. Non-limiting examples of such therapeutic agents include antineoplastic agents, anti-infective agents, local anesthetics, anti-allergics, antianemics, angiogenesis, inhibitors, beta-adrenergic blockers, calcium channel antagonists, anti-hypertensive agents, anti-depressants, anti-convulsants, anti-bacterial, anti-fungal, anti-viral, anti-rheumatics, anthelminithics, antiparasitic agents, corticosteroids, hormones, hormone antagonists, immunomodulators, neurotransmitter antagonists, anti-diabetic agents, anti-epileptics, anti-hemmorhagics, anti-hypertonics, antiglaucoma agents, immunomodulatory cytokines, sedatives, chemokines, vitamins, toxins, narcotics, imaging agents, and combinations thereof.

Nucleic acid-based therapeutic agents are highly applicable to the LN formulations of the present disclosure. Examples of such nucleic acid-based therapeutic agents include, but are not limited to: pDNA, siRNA, miRNA, anti-miRNA, ASO, and combinations thereof. To protect from serum nucleases and to stabilize the therapeutic agent, modifications to the substituent nucleic acids and/or phosphodiester linker can be made. Such modifications include, but are not limited to: backbone modifications (e.g., phosphothioate linkages); 2' modifications (e.g., 2'-O-methyl substituted bases); zwitterionic modifications (6'-aminohexy modified ODNs); the addition of a lipophilic moiety (e.g., fatty acids, cholesterol, or cholesterol derivatives); and combinations thereof. The modified sequences synergize with the LN formulations disclosed herein. For example, addition of a 3'-cholesterol to an ODN supplies stability to a LN complex by adding lipophilic interaction in a system otherwise solely held together by electrostatic interaction. In addition, this lipophilic addition promotes cell permeation by localizing the ODN to the outer leaflet of the cell membrane. Applying a peptide such as gramicidin or JTS-1 further promotes cell permeation of the formulation due to its fusogenic properties. Alternatively, addition of an enzyme such as proteinase K could further aid the ODN in resisting degradation.

Depending on the therapeutic application, the LNs described herein may be administered by the following methods: peroral, parenteral, intravenous, intramuscular, subcutaneous, intraperitoneal, transdermal, intratumoral, intraarterial, systemic, or convection-enhanced delivery. In particular embodiments, the LNs are delivered intravenously, intramuscularly, subcutaneously, or intratumorally. Subsequent dosing with different or similar LNs may occur using alternative routes of administration.

Pharmaceutical compositions of the present disclosure comprise an effective amount of a lipid nanoparticle formulation disclosed herein, and/or additional agents, dissolved or dispersed in a pharmaceutically acceptable carrier. The phrases "pharmaceutical" or "pharmacologically acceptable" refers to molecular entities and compositions that produce no adverse, allergic or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it will be understood that preparations should meet sterility, pyrogenicity, general safety and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, topically, intramuscularly, subcutaneously, mucosally, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight or surface area, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agents is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158; 5,641,515; and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

Sterile injectable solutions are prepared by incorporating the compositions in the required amount in the appropriate solvent with various of the other ingredients enumerated above, as required, followed by filter sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream or powder. Ointments include all oleaginous, adsorption, emulsion and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Lipid stock solutions were created by dissolving lipids in 100% ethanol. All lipids were obtained from Avanti Polar Lipids (USA) or Sigma Aldrich (USA) and used without further purification. Lipids (egg phosphatidylcholine:cholesterol:TPGS, 15:35:5) were combined with varying concentrations of tertiary (DODMA) and quaternary (DOTMA) amine (45:0, 5:40, 15:30, 22.5:22.5, 30:15, 40:5, 45:0; DODMA:DOTMA) in 1.0 mL vials. Additional ethanol was added to reach a volume of 180 µL. This was then combined with 420 µL 10 mM citric acid buffer to reach a final concentration of 30% ethanol. The formulations were combined with SILENCER Firefly Luciferase (GL2+GL3) siRNA (Invitrogen) at an amine to phosphate (N:P) ratio of 15:1. Formulations were allowed to incubate for 15 minutes prior to dilution with serum-free DMEM (GIBCO) to a total volume of 300 µL. Lipofectamine 2000 (Invitrogen) was used as a positive control and combined with the same amount of siRNA at the same N:P and diluted to the same total volume.

SK-HEP-1 (hepatocellular carcinoma) cells expressing luciferase, grown in DMEM medium at 37° C. under 5% $CO_2$ atmosphere, were plated 24 h prior to transfection at a density of $2 \times 10^4$ cells per well in a 96-well plate. Cells were grown to approximately 80% confluency and the serum containing media was removed. Cells were transfected with 70 µL transfection media and treated for 4 h. Experiments were performed with four replicates. After treatment was completed, cells were washed with 1×PBS and serum-containing DMEM was restored. 48 h after treatment was completed, cells were analyzed for luciferase expression by a Luciferase Assay Kit (Promega) per the manufacturer's instructions. The results are shown in FIG. 1. The most efficacious transfection activity was exhibited by the formulation containing 5% DOTMA and 40% DODMA, showing over 85% knockdown in luciferase expression.

Example 2

Lipid stock solutions were created by dissolving lipids in 100% ethanol. All lipids were obtained from Avanti Polar Lipids (USA) or Sigma Aldrich (USA) and used without further purification. Lipids (egg phosphatidylcholine:cholesterol:TPGS, 15:35:5) were combined with varying concentrations of tertiary (DMHDA) and quaternary (DOTMA) amine (90:10, 70:30, 50:50, 30:70, 10:90; DMHDA:DOTMA) in 1.0 mL vials. Additional ethanol was added to reach a volume of 180 µL. This was then combined with 420 µL 10 mM citric acid buffer to reach a final concentration of 30% ethanol. The formulations were combined with G3139 (Genasense) ODN at an amine to phosphate ratio (N:P) of 15:1. Formulations were allowed to incubate for 15 min prior to dilution with serum-free RPMI 1640 (Mediatech) to a total volume of 300 µL. Lipofectamine 2000 (Invitrogen) was used as a positive control and combined with the same amount of ODN at the same N:P and diluted to the same total volume.

Figure 2:
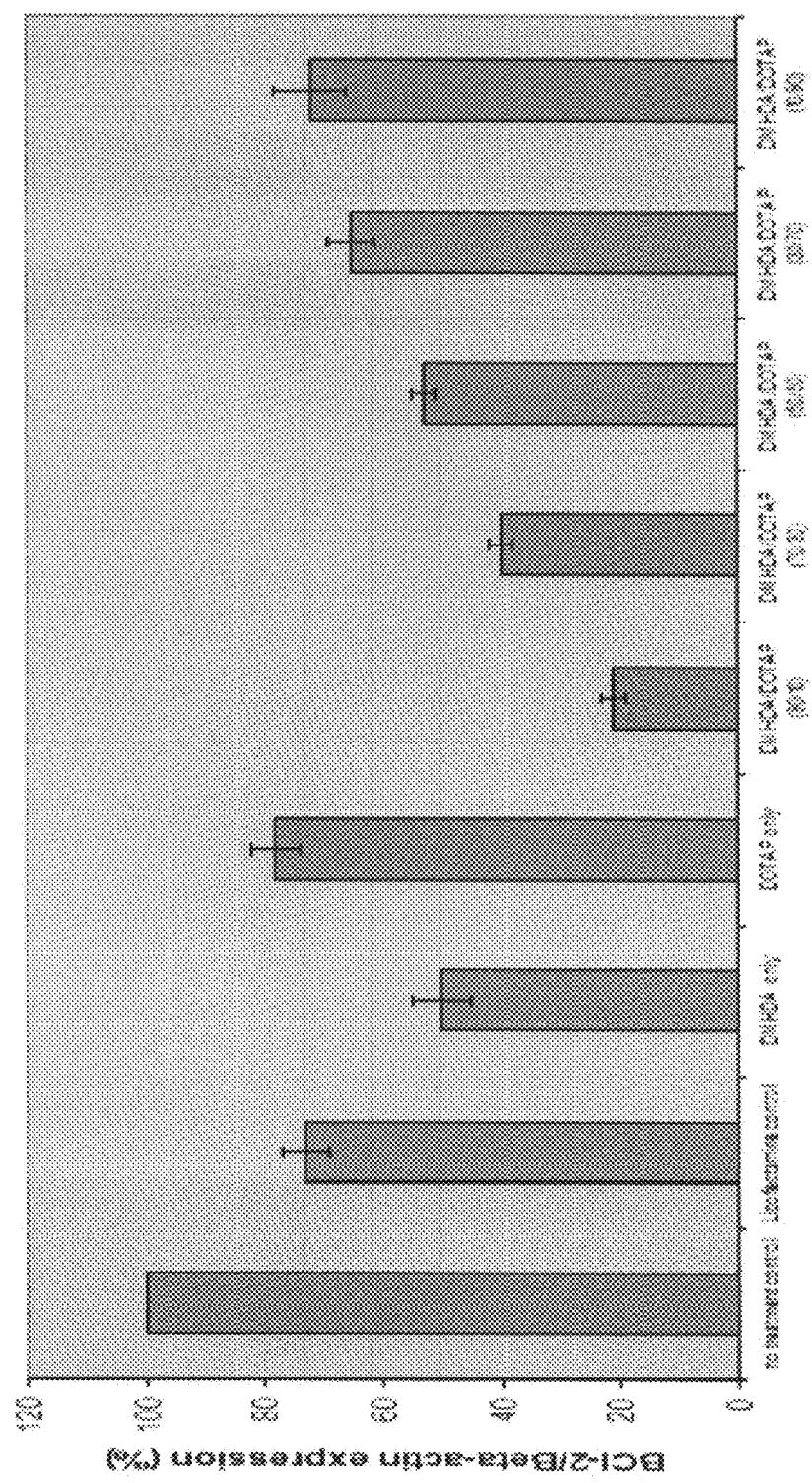
FIG. 2: Downregulation of Bcl-2 expression in KB cells by G3139 in QTsome. QTsomes containing varying amounts of DMHDA were evaluated. Lipo2000 is used as a positive control. Bcl-2 mRNA expression relative to actin was determined by RT-PCR where untreated KB cells served as a baseline for mRNA expression.

KB (a subline of HeLa) cells, grown in RPMI 1640 medium at 37° C. under 5% $CO_2$ atmosphere, were plated 24 h prior to transfection at a density of $2 \times 10^4$ cells per well in a 96-well plate. Cells were grown to approximately 80% confluency and the serum containing media was removed. Cells were transfected with 70 µL transfection media and treated for 4 h. Experiments were performed with four replicates. After treatment was completed, cells were washed with 1×PBS and serum-containing RPMI 1640 was restored. 48 h after treatment was completed, cells were analyzed for Bcl-2 downregulation. Real-time polymerase chain reaction (RT-PCR) was used to assess the downregulation of Bcl-2 relative to actin. As shown in FIG. 2, transfection with the formulation containing DMHDA/DOTAP (90/10 molar ratio) results in greater than 75% downregulation of Bcl-2 expression compared to untransfected cells. Lipofectamine™, DMHDA alone, and DOTAP alone served as controls. Formulations of DMHDA/DOTAP at alternative ratios showed lower rates of transfection efficiency.

Example 3

Figure 3:
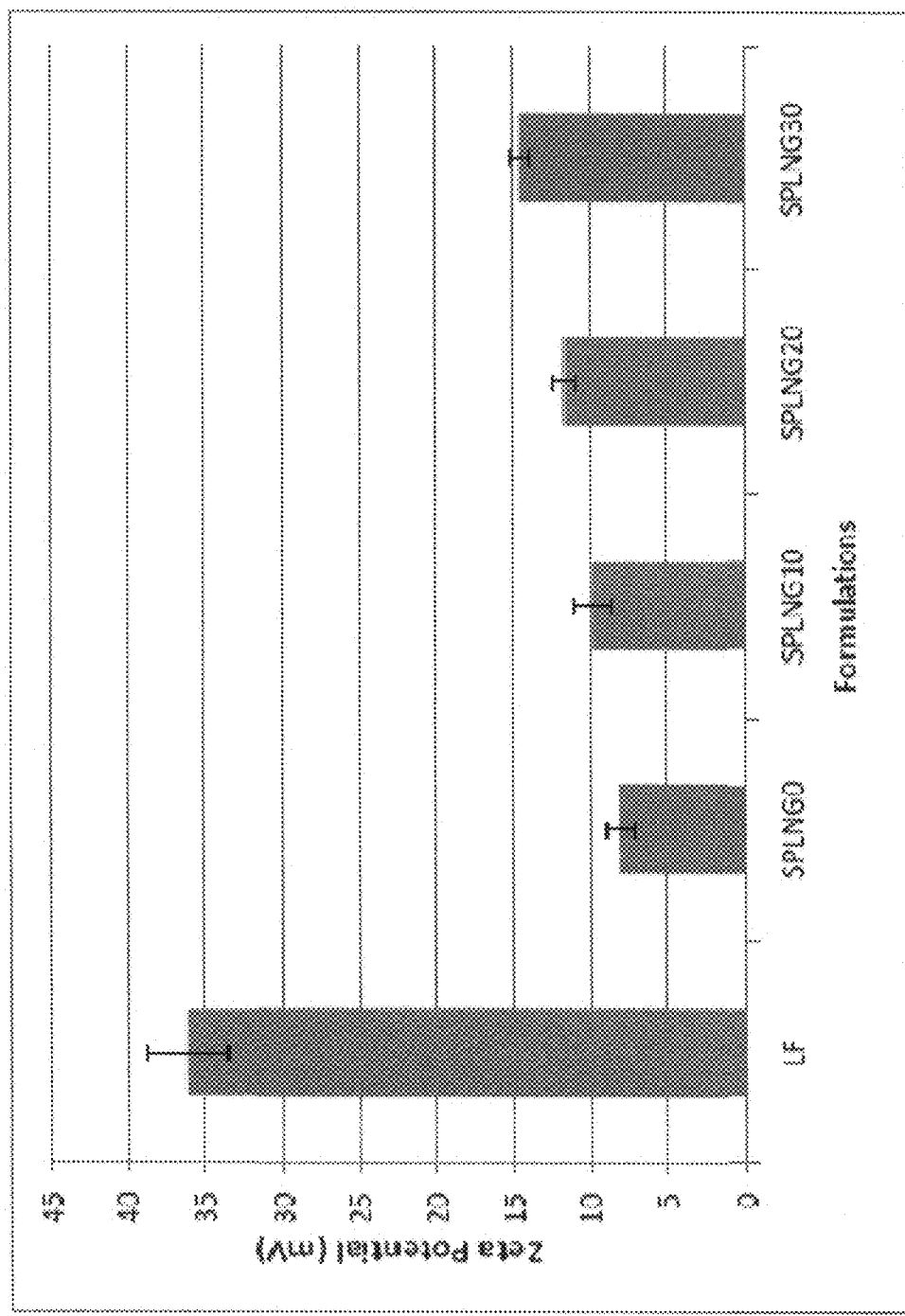
FIG. 3: Zeta potential of SPLN-G condensed with c-myb at a N:P of 15:1.

Various SPLN-G formulations were analyzed for transfection efficacy: SPLN-G50 (DMHDA, DOTAP, GRAM, TPGS at a molar ratio of 40:5:50:5), SPLN-G35 (DMHDA, DOTAP, GRAM, DOPE, TPGS at a molar ratio of 40:5:35:15:5), SPLN-G30 (DMHDA, DOTAP, GRAM, DOPE, TPGS at a molar ratio of 40:5:30:20:5), SPLN-G20 (DMHDA, DOTAP, GRAM, DOPE, TPGS at a molar ratio of 40:5:20:30:5), SPLN-G10 (DMHDA, DOTAP, GRAM, DOPE, TPGSS at a molar ratio of 40:5:10:40:5), and SPLN-GO (DMHDA, DOTAP, DOPE, TPGS at a molar ratio of 40:5:50:5). All lipids were purchased from Avanti Polar Lipids (USA) or Sigma Aldrich (USA) and used without further purification. Lipids and peptides were dissolved in ethanol and combined at the appropriate ratios to form LNs. Additional ethanol and citric acid buffer was added to attain a final ethanol content of 30%. The 2.0 mg/mL LN solution was combined with siRNA or ODN at an N:P of 15:1 and allowed to react at room temperature for 15 min before further dilution. Particle sizes of the formulation ranged between 100-300 nm. Zeta potential measurements (FIG. 3) of the formulation diluted with deionized water and combined with c-myb ODN demonstrated zeta potentials ranging between 5-15 mV for gramicidin-containing formulations. This is in contrast to the positive control, Lipofectamine 2000, which exhibited a zeta potential above 35 mV.

Figure 4:
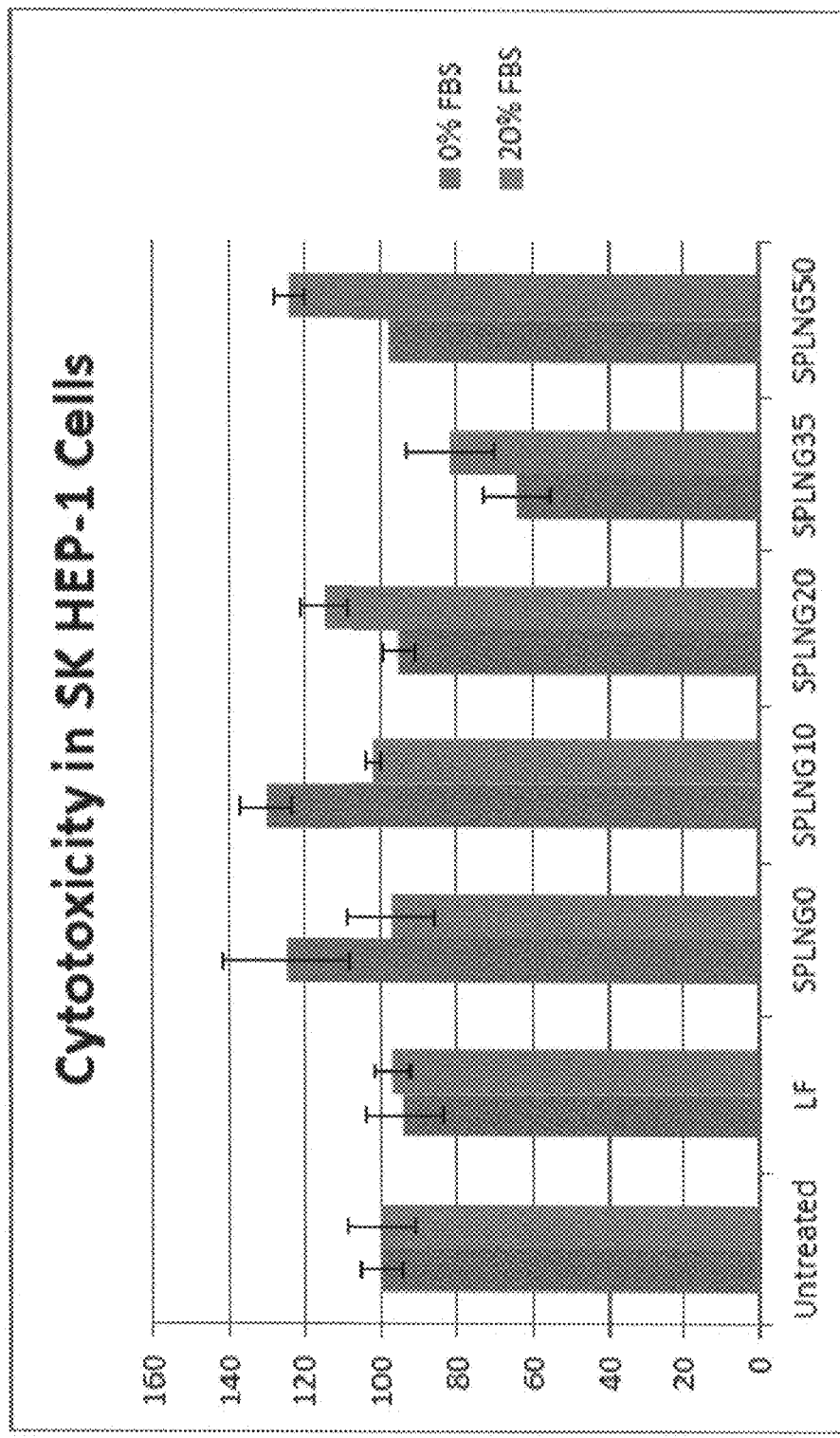
FIG. 4: Viability of SK-HEP-1 cells treated with SPLN-G under 0% and 20% serum conditions. Cell viabilities are expressed as a percentage relative to the mean viability of the untreated SK-HEP-1 cells.

SK-HEP-1 cells, cultured in DMEM media (GIBCO) supplemented with 10% FBS and 1% streptomycin/penicillin at 37° C. under 5% $CO_2$ atmosphere were grown to confluency and plated at a density of $2 \times 10^4$ cells per well in a 96-well plate. Firefly Luciferase (GL2+GL3) siRNA was combined with the formulations at N:P 15:1. Formulations were allowed to combine with lipid formulations for 15 min at room temperature prior to dilution with DMEM. Transfection efficiency was tested in both serum-free and 20% serum conditions. Culture medium was removed and replaced with 70 µL transfection medium per well. Cells were treated for 4 h before washing three times with 1×PBS. 48 h after treatment, cell viability (FIG. 4) and luciferase expression (FIG. 5) were analyzed by MTS assay and Luciferase Assay Kit, respectively. Formulations containing 35% or less gramicidin exhibited lower cytotoxicity and greater transfection efficiency than Lipofectamine 2000 under high serum transfection conditions.

Figure 6:
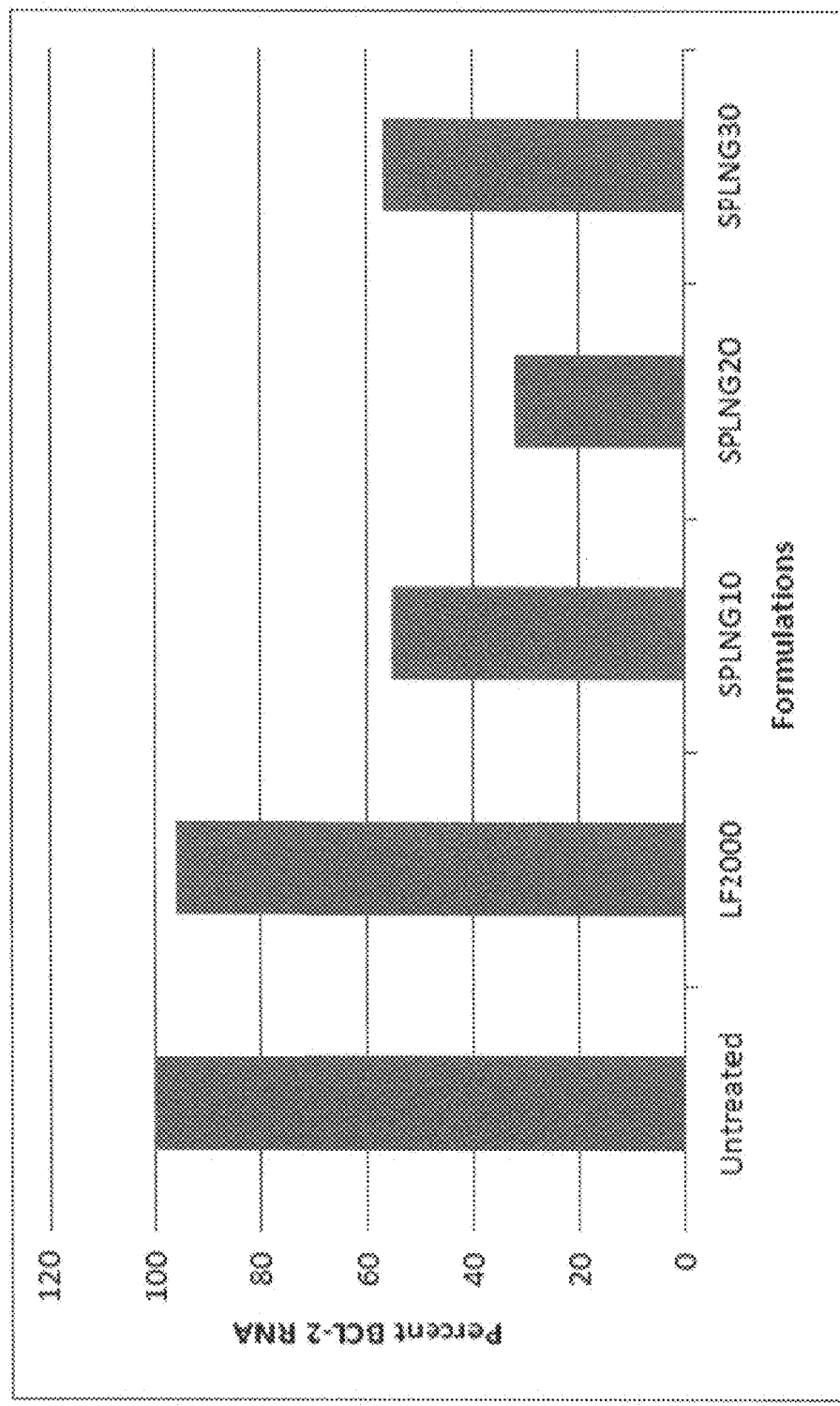
FIG. 6: Downregulation of Bcl-2 expression in MCF-7 cells using SPLN-G loaded with G3139, an ASO against Bcl-2. Lipo2000 is used as a positive control Bcl-2 mRNA expression relative to actin was determined by RT-PCR where untreated MCF-7 cells served as a baseline for mRNA expression.
Figure 7:
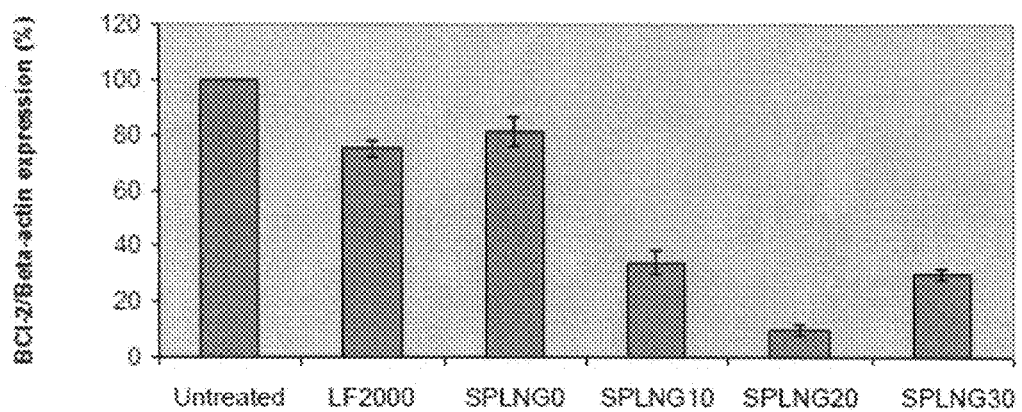
FIG. 7: Downregulation of Bcl-2 expression in KB cells using SPLN-G loaded with G 3139, an ASO against Bcl-2. Lipo2000 is used as a positive control. Bcl-2 mRNA expression relative to actin was determined by RT-PCR where untreated KB cells served as a baseline for mRNA expression.

Bcl-2 downregulation via ODN G3139 was investigated in MCF-7 (ER positive breast cancer) cells. Transfection occurred in the presence of 20% serum RT-PCR (FIG. 6) was used to assess the downregulation of Bcl-2 relative to actin. SLN-G20 exhibited significant downregulation of Bcl-2 relative to Lipofectamine 2000. This was repeated in KB cells with replicates (n=3), as seen in FIG. 7.

Example 4

Figure 8:
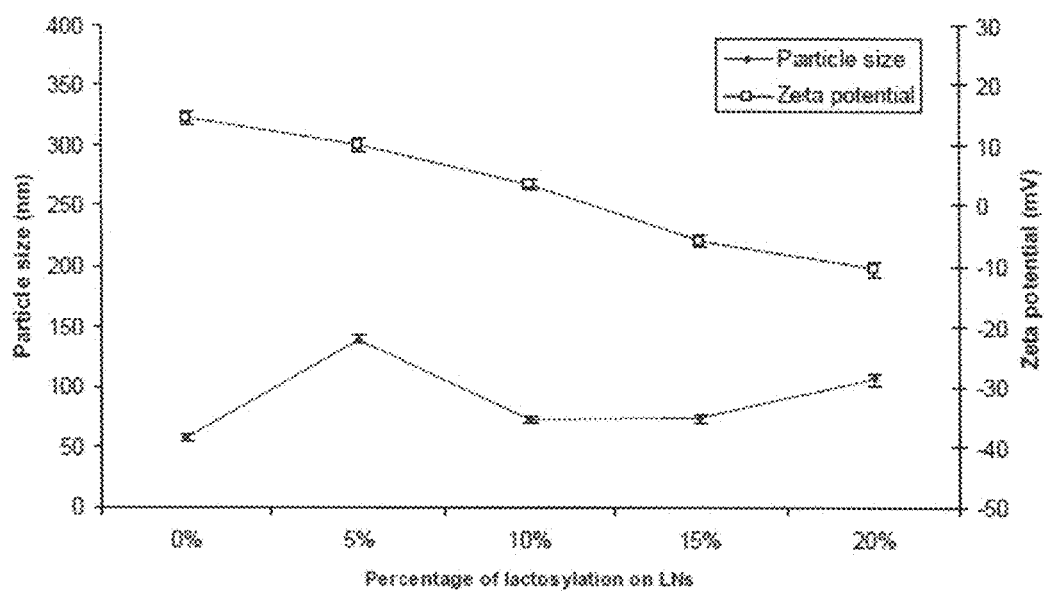
FIG. 8: Effect of lactosylation on SPLN-G size and zeta potential. These are targeting liver and liver cancer cells via the asialoglycoprotein receptor (ASGR).

Lactosylated DOPE (L-DOPE) was formed by crosslinking lactobionic acid with DOPE using EDC/NHS (1:5:10:5, DOPE:LA:EDC:NHS). Lipids and peptide (DODAP: DOTAP:L-DOPE:DMG-PEG:Gramicidin at a molar ratio of 45:5:5:10:28:2:10) were combined in 1×PBS. Other control formulations were completed with L-DOPE (substituted with DOPE) and/or gramicidin. The particle size (FIG. 8) of the formulated LNs fell between 50 and 150 nm. The formulation displayed colloidal stability over a 30 day period. Zeta potential (FIG. 8) of the LNs ranged between −10 and 10 mV. Investigation of ODN loading efficiency revealed over 75% condensation.

Figure 9:
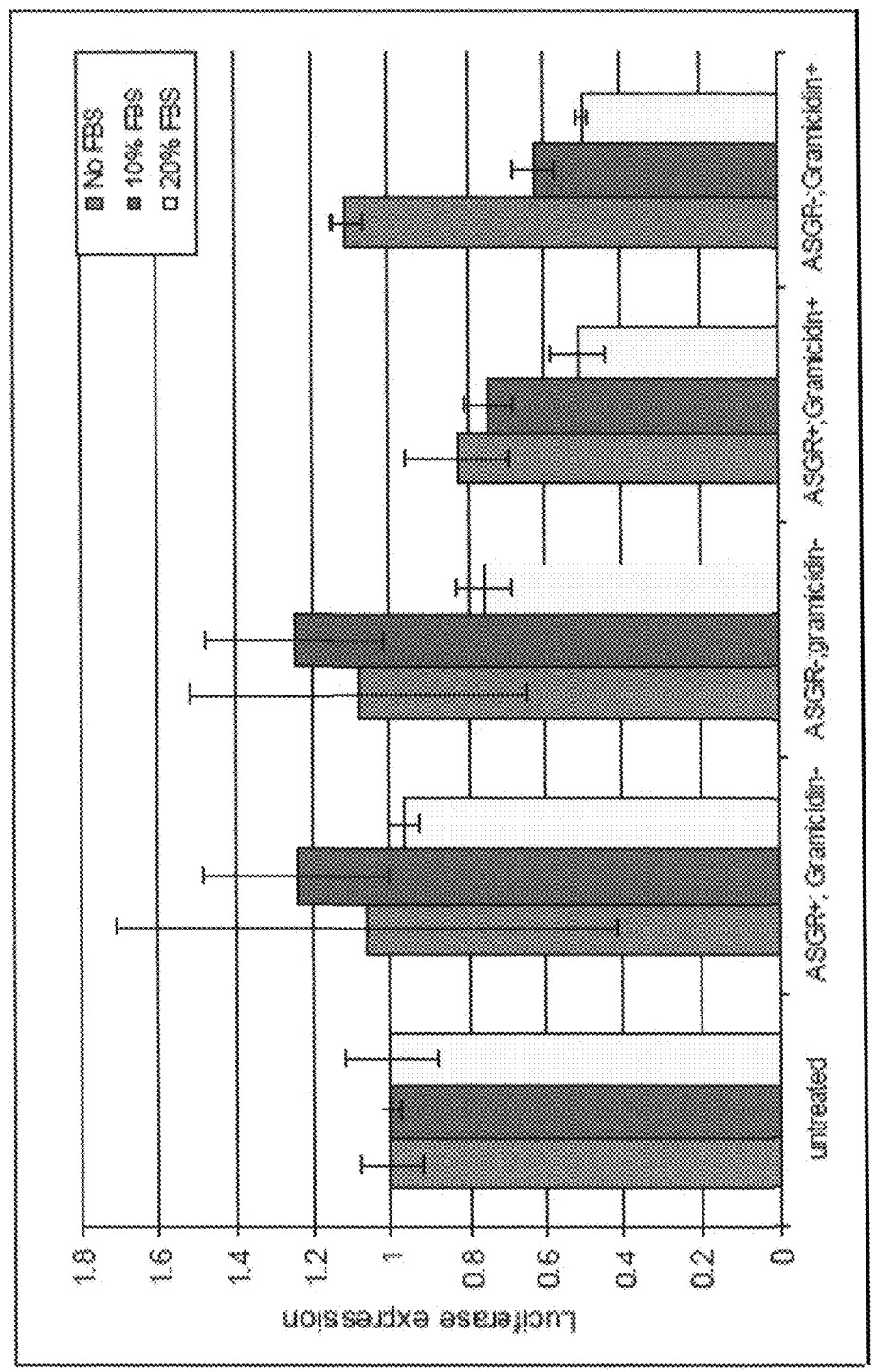
FIG. 9: Evaluation of asialoglycoprotein receptor (ASGR) targeting and gramicidin in SPLN-G by luciferase assay in luciferase-expressing SK-HEP-1 cells. Luciferase activity is expressed as a percentage relative to untreated cells.

Luciferase assay was used to determine targeting efficiency of LLNs in SK-HEP-1 cells expressing luciferase. SK-HEP-1 cells, cultured in DMEM media (GIBCO) supplemented with 10% FBS and 1% streptomycin/penicillin at 37° C. under 5% $CO_2$ atmosphere were grown to confluency and plated at a density of $2\times10^4$ cells per well in a 96-well plate. Firefly Luciferase (GL2+GL3) siRNA was combined with the formulations at N:P 10:1. Formulations were allowed to combine with lipid formulations for 10 m at room temperature prior to dilution with DMEM. Transfection efficiency was tested in serum-free, 10%, and 20% serum conditions. Culture medium was removed and replaced with 70 μL transfection medium per well (siRNA 100 nM). Cells were treated for 4 h before washing three times with 1×PBS. 48 h after treatment, luciferase expression (FIG. 9) was analyzed by a luciferase assay kit. Formulations containing both gramicidin as well as ASGR showed greater transfection efficiency than either LN modification alone.

Figure 10:
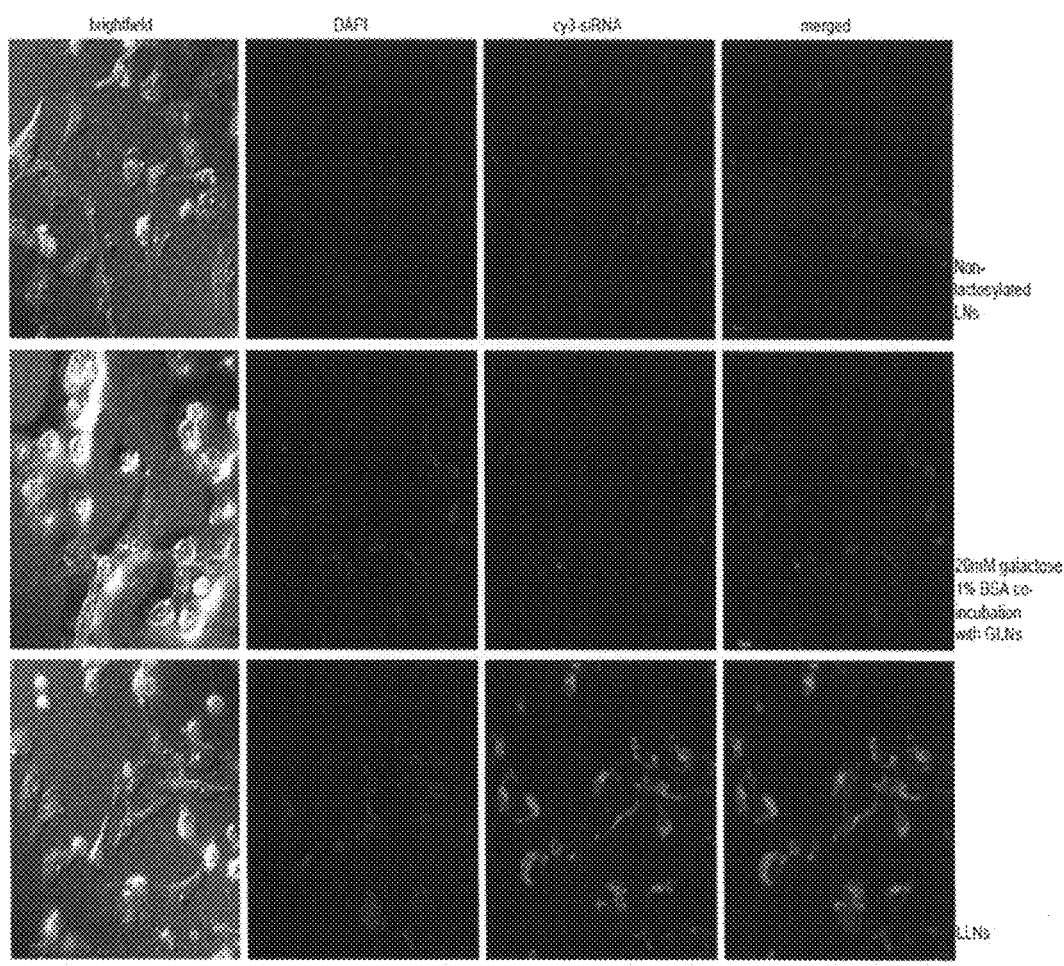
FIG. 10: Cellular trafficking of SPLN-G via confocal microscopy. DAPI (blue) was used to stain the nuclei of cells. siRNA-Cy3 (red) was used to track siRNA for internalization. The overlay shows that a high percentage of siRNA is delivered to the cytosol.
Figure 11:
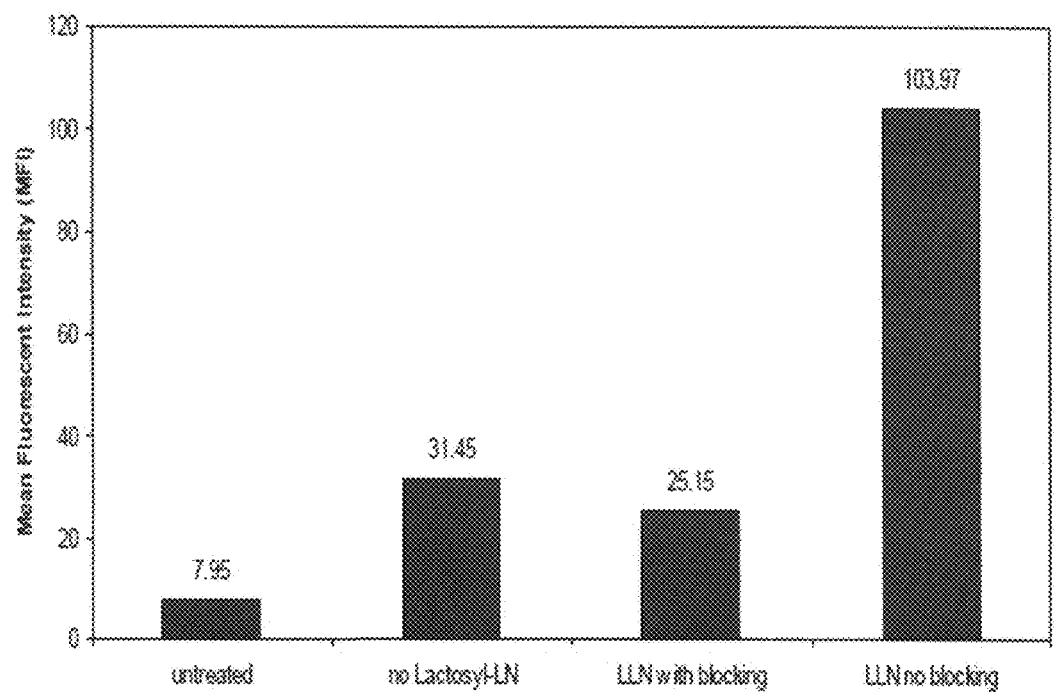
FIG. 11: Cellular uptake of non-targeted SPLN-G and lactosylated SPLN-G (Lac-SPLN-G) encapsulating Cy3-siRNA via flow cytometry.
Figure 12:
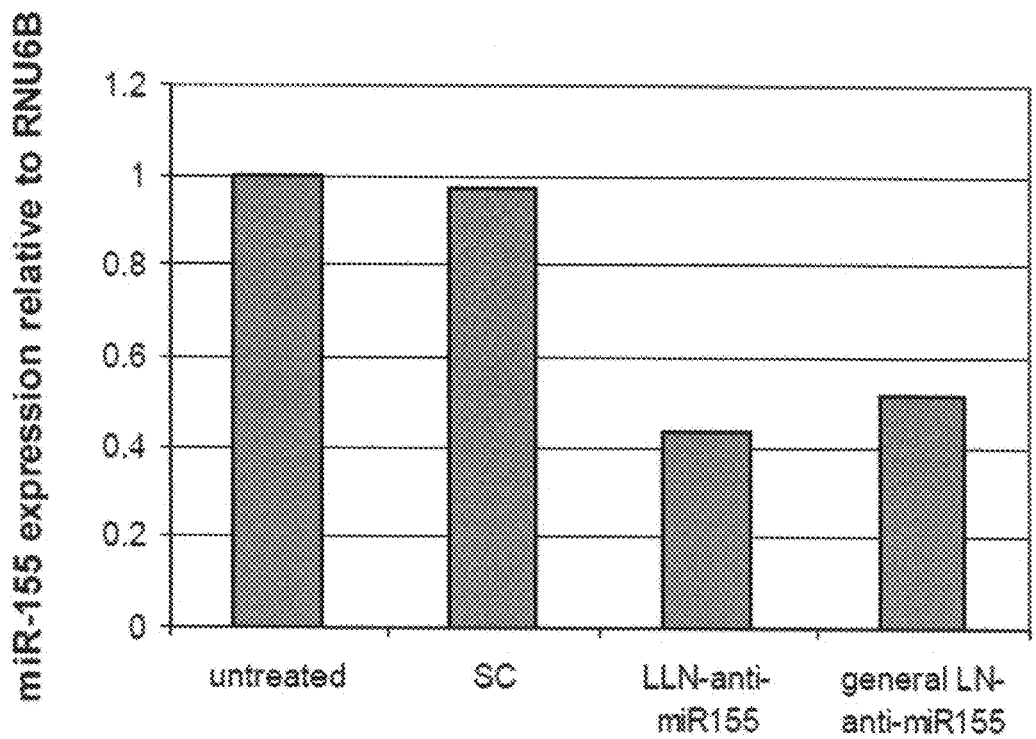
FIG. 12: Downregulation of miR-155 in SK-HEP-1 cells by Lac-SPLN-G-anti-miR-155. Scrambled control miRNA (SC) was used as a negative control. miR-155 expression relative to RNU6B was determined by RT-PCR where untreated SK-HEP-1 cells served as a baseline for mRNA expression.

Uptake of LLNs was analyzed by fluorescent microscopy (FIG. 10) and flow cytometry (FIG. 11). DAPI nuclear was applied to hepatocellular carcinoma (HCC) cells cy3-labeled oligonucleotides were added to indicate the cellular uptake. As demonstrated by the fluorescent images, ASGR targeting is necessary for efficacious delivery of siRNA and ODN to the cytosol of cells. Flow cytometry data showed an approximate 3.3 fold difference between targeted LLNs and non-targeted LLNs, further substantiating the advantages of targeted delivery. Downregulation of miR-155 by LN-antagomir formulations was assessed by RT-PCR (FIG. 12). About 60% downregulation of miR-155 was achieved relative to RNU6B. 100 nM anti-miR-155 was used.

Example 5

Figure 13:
FIG. 13: Gel mobility shift analysis of Lac-SPLN-G-siRNA complexes at varying lipid-to-siRNA (w/w) ratios.
Figure 14:
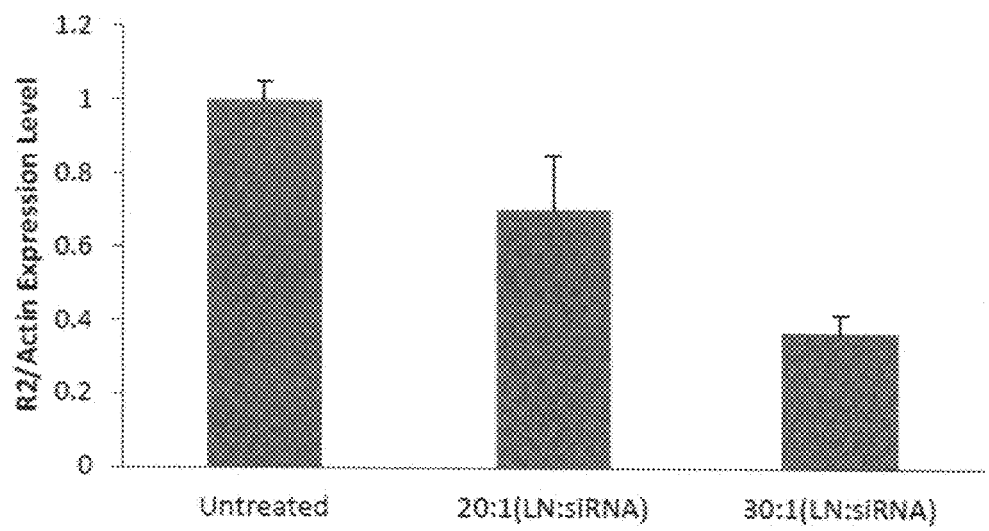
FIG. 14: Downregulation of RNR R2 expression in KB cells using PrKsome carrying LOR-1284, an siRNA targeting ribonucleotide reductase RNR R2 subunit (purchased from Dharmacon). RNR R2 mRNA expression relative to actin was determined by qRT-PCR where untreated KB cells served as a baseline for mRNA expression.

Lipids (DDAB, CHOL, Tween 80 at a molar ratio of 60:35:5) were dissolved in 100% ethanol. 100 μL of this solution was diluted in 900 μL 1×PBS. LNs at various w/w ratios were combined with LOR-1284 (siRNA purchased from Dharmacon) (0.1 μg) for gel mobility shift analysis (FIG. 13). Retardation occurred at 1:8 (siRNA:LN). LNs were combined with 0.1 μM siRNA for downregulation studies. Downregulation of RNR R2 by LN-siRNA LOR-1281 formulations was assessed by RT-PCR using actin as a control and w/w ratios 1:20 and 1:30 (siRNA:LN). KB cells, grown in RPMI 1640 medium at 37° C. under 5% $CO_2$ atmosphere, were plated 24 h prior to transfection at a density of $3.0\times10^5$ cells per well in a 6-well plate. Cells were grown to approximately 80% confluency and the serum containing media was removed. Cells were transfected with 1000 μL transfection media and treated for 4 h. Transfection occurred in the presence of 10% serum-containing RPMI 1640 media. Experiments were performed with 3 replicates. After treatment was completed, cells were washed with 1×PBS and serum-containing RPMI 1640 was restored. 48 h after treatment was completed, cells were analyzed for RNR R2 expression levels by RT-PCR with actin as a housekeeping gene. Results are located in FIG. 14. Significant downregulation occurred for the 1:30 siRNA:LN formulation.

Figure 15A:
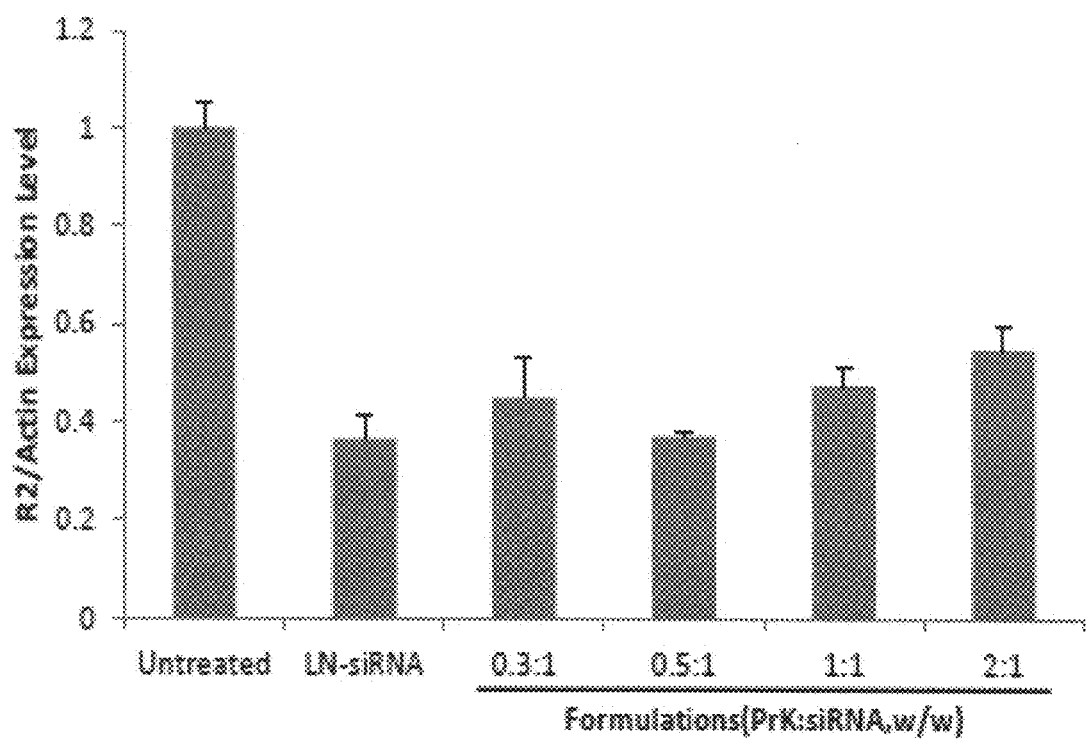
FIGS. 15A-B: Downregulation of RNR R2 expression levels with PrKsome in varying serum conditions.
Figure 15B:
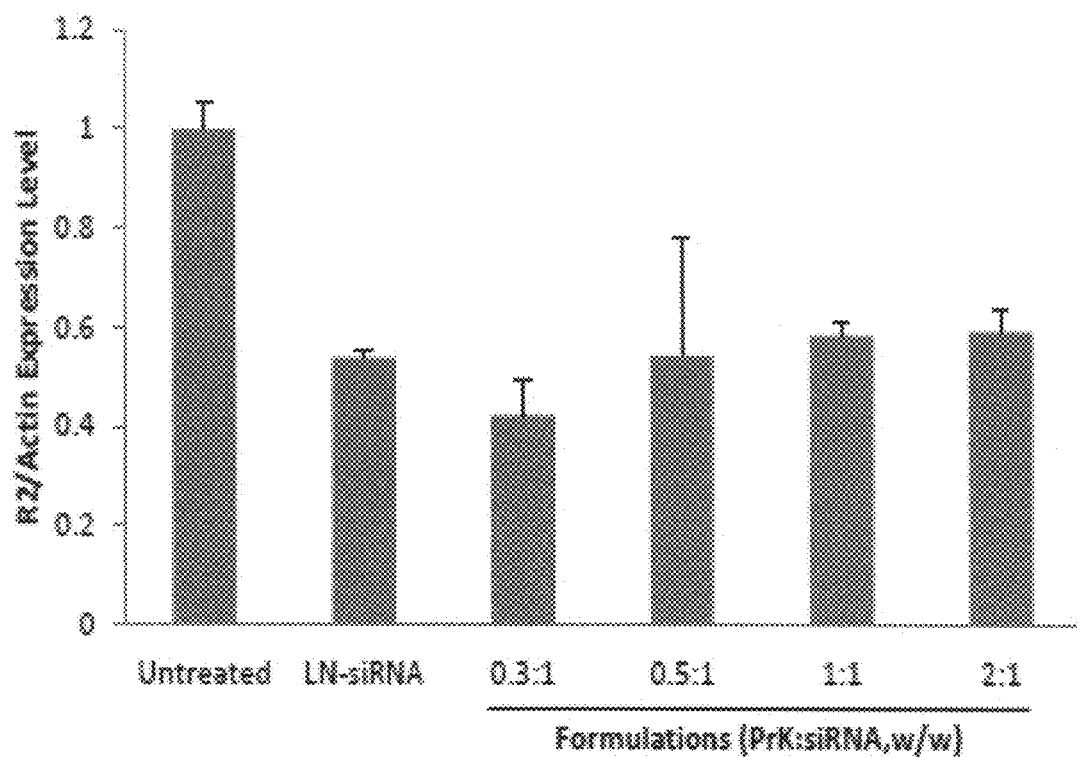
Figure 15C:
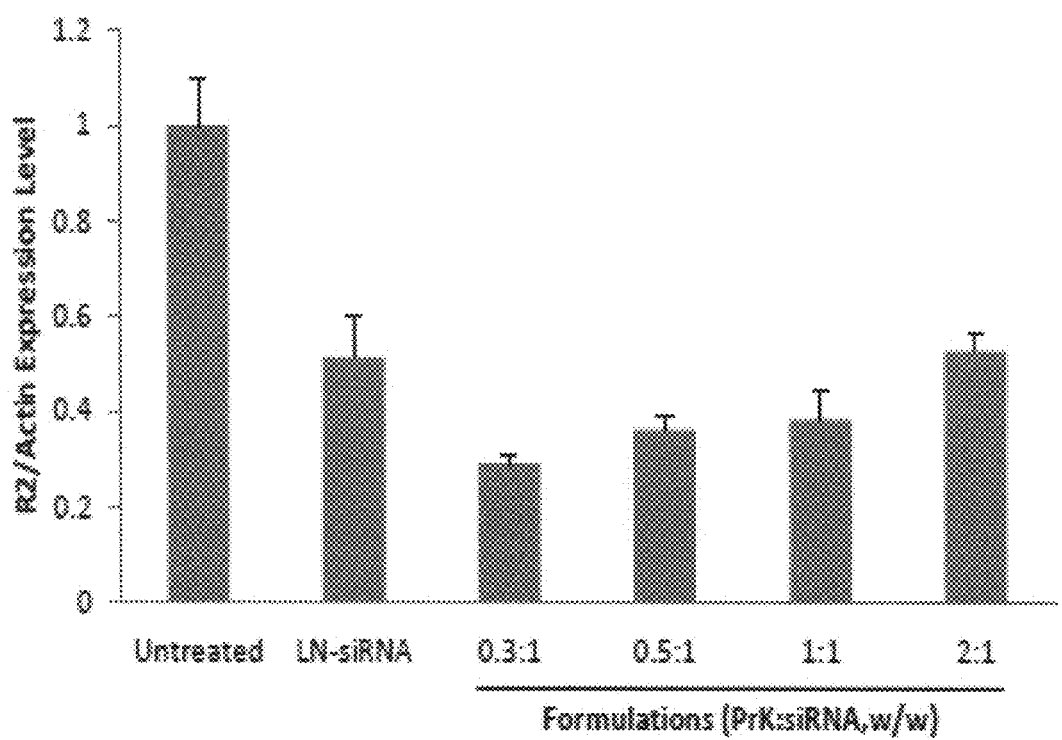
FIG. 15C shows 10% FBS. RNR R2 mRNA expression relative to actin was determined by real-time RT-PCR where untreated KB cells served as a baseline for mRNA expression.
Figure 16:
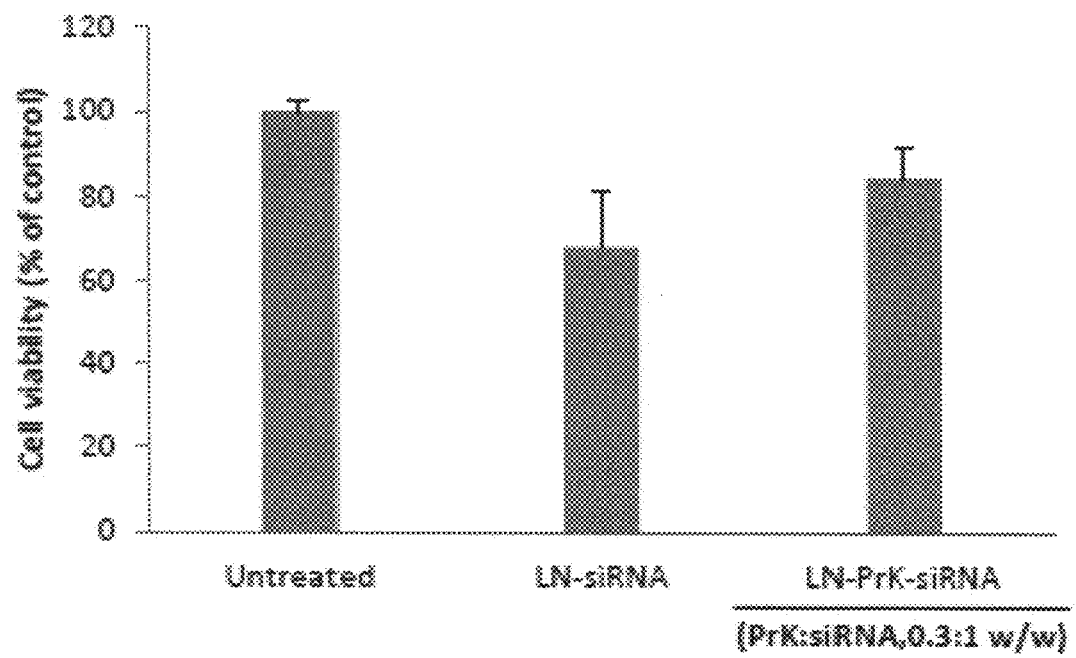
FIG. 16: Comparative cell viability study of lipid nanoparticle with and without PrK. Cell viabilities are expressed as a percentage relative to the mean viability of the untreated KB cells.
Figure 17:
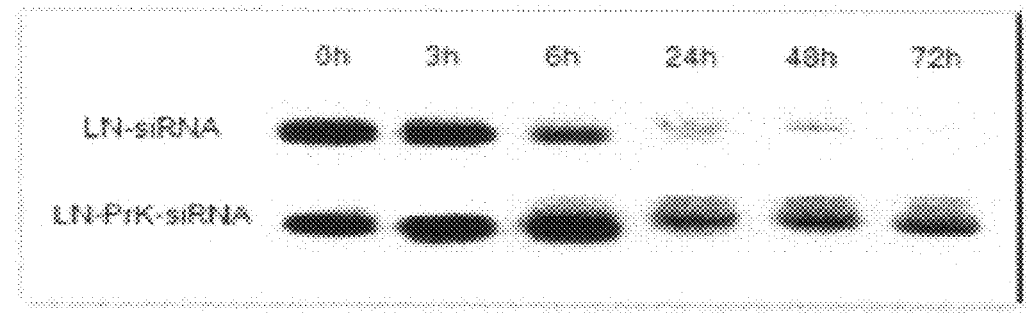
FIG. 17: Stability study of LOR-1284 siRNA in blood plasma. PrKsome formulations were incubated in mouse plasma over a period of 72 hours and the relative amount of siRNA remaining was visualized by gel electrophoresis.

The LNs (1:30, siRNA:LN) of the previous step were combined with various amounts of PrK pre-mixed with LOR-1284 for 15 min in room temperature. KB (mouth carcinoma) cells, grown in RPMI 1640 medium at 37° C. under 5% $CO_2$ atmosphere, were plated 24 h prior to transfection at a density of $3.0\times10^5$ cells per well in a 6-well plate. Cells were grown to approximately 80% confluency and the serum containing media was removed. Cells were transfected with 1000 μL transfection media and treated for 4 h. Transfection occurred in the presence of 0%, 5%, and 10% serum-containing RPMI 1640 media. Experiments were performed with 3 replicates. After treatment was completed, cells were washed with 1×PBS and serum-containing RPMI 1640 was restored. 48 h after treatment was completed, cells were analyzed for RNR R2 expression levels by RT-PCR with actin as a housekeeping gene. Results are shown in FIG. 15. For serum-containing media, the 0.3:1:LN-PrK:siRNA LOR-1281 formulation showed significant downregulation compared to the formulation without PrK. Cell viability studies were also carried out under the same transfection parameters with 10% serum-containing media. Neither the LNs nor the PrK-LNs showed significant toxicity at the treated levels (FIG. 16). The protective effect of PrK-siRNA complexes in serum was investigated by incubating LN-siRNA and PrK-LN-siRNA complexes in fresh mouse plasma (FIG. 17). Inclusion of PrK in the formulation showed significant protective activity over the non-protected formulation over a three day period.

Figure 18:
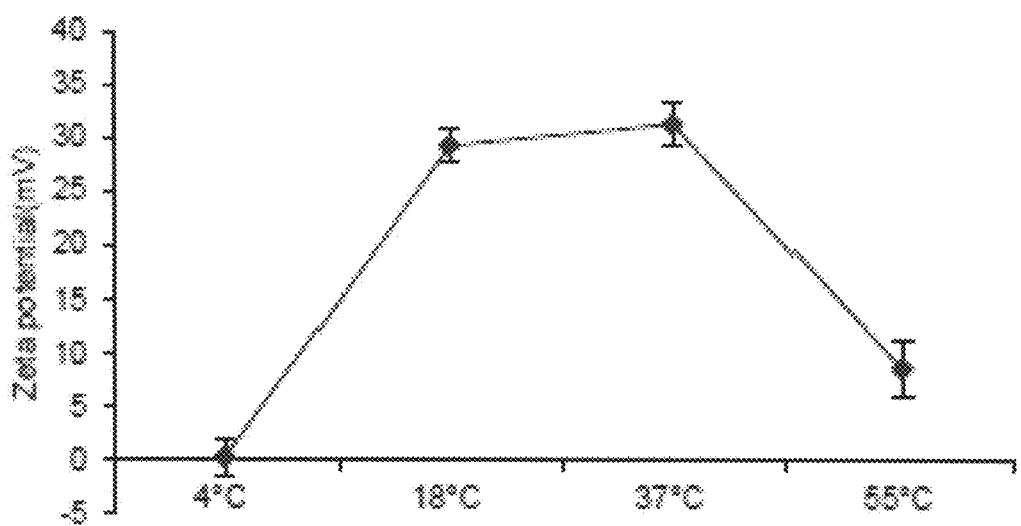
FIG. 18: Temperature dependent zeta potential of PrKsome containing 1:0.3 siRNA:PrK (w/w).
Figure 19:
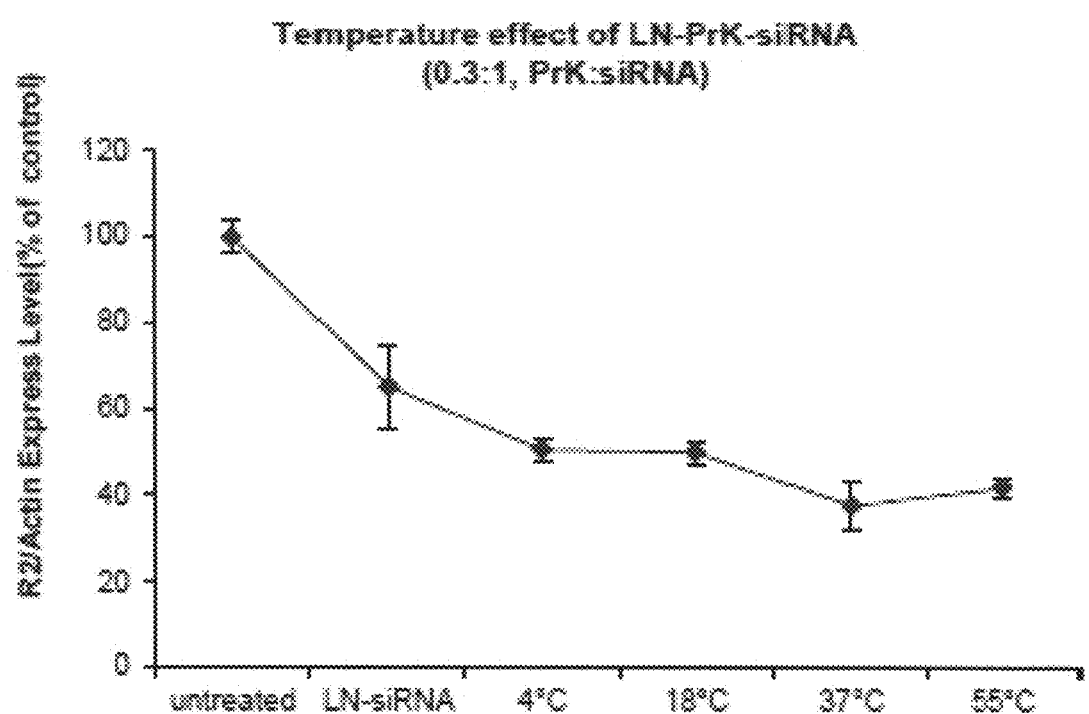
FIG. 19: Temperature-dependent efficacy of RNR R2 downregulation by LOR-1284 siRNA delivered by PrKsome in 10% FBS medium. RNR R2 mRNA expression relative to actin was determined by real-time RT-PCR where untreated KB cells served as a baseline for mRNA expression.

Further study investigated the temperature effect of PrK-LNs. PrK, LOR-1284, and LNs were combined at a weight ratio of 0.3:1:30 with vortexing and were maintained at temperatures of 4° C., 18° C., 37° C., and 55° C. Zeta potentials (FIG. 18) of the formed complexes were measured. Complexes mixed at 18° C. and 37° C. had a much higher zeta potential than those mixed at 4° C. and 55° C. The complexes formed at the various temperatures were tested for in vitro activity. KB cells, grown in RPMI 1640 medium at 37° C. under 5% $CO_2$ atmosphere, were plated 24 h prior to transfection at a density of $3\times10^5$ cells per well in a 96-well plate. Cells were grown to approximately 80% confluency and the serum containing media was removed. Cells were transfected with 1000 μL transfection media and treated for 4 h. Transfection occurred in the presence of 10% serum-containing RPMI 1640 media. Experiments were performed with 2 replicates. After treatment was completed, cells were washed with 1×PBS and serum-containing RPMI 1640 was restored. 48 h after treatment was completed, cells were analyzed for RNR R2 expression levels by RT-PCR with actin as a housekeeping gene. Results are shown in FIG. 19. Formulations complexed at higher temperatures (37° C. and 55° C.) displayed a small increase in transfection efficiency relative to formulations formed at lower temperatures.

Example 6

SPLN-G20 for anti-miR delivery into MDA-MB-468 cells was studied. SPLN-G20 were prepared as described above. MDA-MB-468 (triple negative breast cancer) cells were plated 24 h prior to transfection in a 6-well plate at a density of $2\times10^4$ cells/cm$^2$ in DMEM/F12 media supplemented with 1% penicillin/streptomycin and 10% FBS. SPLN-G20 was combined with anti-miR-221 to gauge its ability to upregulate the downstream target of miR-221, p27/Kip1, a tumor suppressor. The sequence of anti-miR-221 was as follows: 5'-g$_s$a$_s$aacccagcagacaaugu$_s$a$_s$g$_s$c$_s$u-Chol-3' [SEQ ID NO. 1]. This sequence included 2'-O-

Methyl-modified oligonucleotides (lower case letters) and phosphorothioate linkages (s subscript) to aid in nuclease stability of antisense oligonucleotides. Furthermore, the addition of a hydrophobic moiety (cholesterol (Chol)) to the 3' end was added to better facilitate association with the lipid nanoparticle formulation. MDA-MB-468 cells were transfected using SPLN-G20 with 50, 100, and 250 nM anti-miR-221 in the presence of 20% serum. Treatment was allowed to proceed for 4 h at which time the transfection medium was removed and replaced with fresh media (supplemented with 10% FBS). Cells were allowed to proliferate for an additional 44 h before the start of RT-PCR. RNA from cells was extracted by TRIzol Reagent (Life Technologies) and cDNA was generated by SuperScript® III First-Strang Synthesis System (Life Technologies) per the manufacturer's instructions. RT-PCR was then performed using SYBR green (Life Technologies) and primers for p27/kip1 (Alpha DNA)

```
forward:
                                     [SEQ ID NO. 2]
5'CGTGCGAGTGTCTAACGG-3', reverse:
                                     [SEQ ID NO. 3])
5'-CGGATCAGTCTTTGGGTC-3'.

β-actin (forward:
                                     [SEQ ID NO. 4]
5'-CGTCTTCCCCTCCATCG-3',
``` reverse: 5'-CTCGTTAATGTCAC GCAC-3') [SEQ ID NO. 5] was used as a control. As seen in FIG. 24, the mRNA was upregulated several fold in a dose dependent manner through the treatment of SPLN-G/anti-miR-221.

Example 7

SPLN-G20 version 1 (SPLN-G20v1) composed of DMHDA, DOTAP, GRAM, DOPE, TPGS at a molar ratio of 40:5:20:30:5 was prepared as described previously. A second version of SPLN-G20 (SPLN-G20v2) was also generated, replacing DMHDA and DOPE with DODAP and Soy PC (SPC), respectively. DODAP is also a tertiary amine and is better characterized than DMHDA in transfection. In this embodiment, the choice to replace the helper lipid with SPC was made because DOPE based formulations generally show reduced activity in vivo due to interaction with serum proteins. The final composition was set at a molar ratio of 40:5:20:30:5 (DODAP:DOTAP:GRAM:SPC:TPGS). All lipids and peptide were purchased from Avanti Polar Lipids (USA) or Sigma-Aldrich (USA) and used without further purification. Lipids and peptides were dissolved in ethanol and combined at the appropriate ratio. Additional ethanol and citric acid buffer, pH 4.0, was added to reach a final ethanol content of 30%. At this point, the 2.0 mg/mL lipid nanoparticle solution was combined with anti-miR at an N:P of 15:1, bath-sonicated for 5 min, and allowed to form electrostatic complexes at room temperature for 15 min before further dilution. Particle size of the formulation ranged between 100-200 nm.

Figure 25:
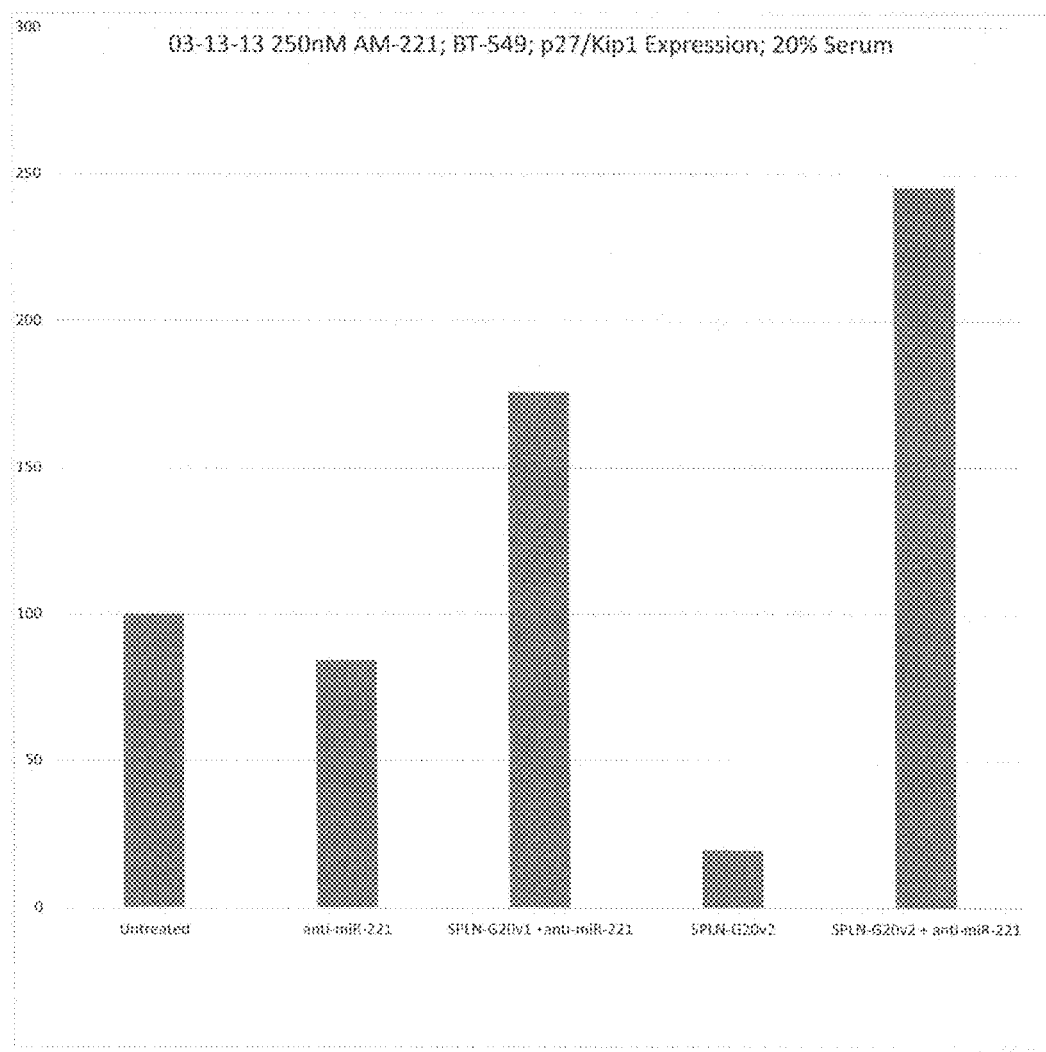
FIG. 25: SPLN-G20 transfection in p27/Kip1 of BT-549 cells.
Figure 26:
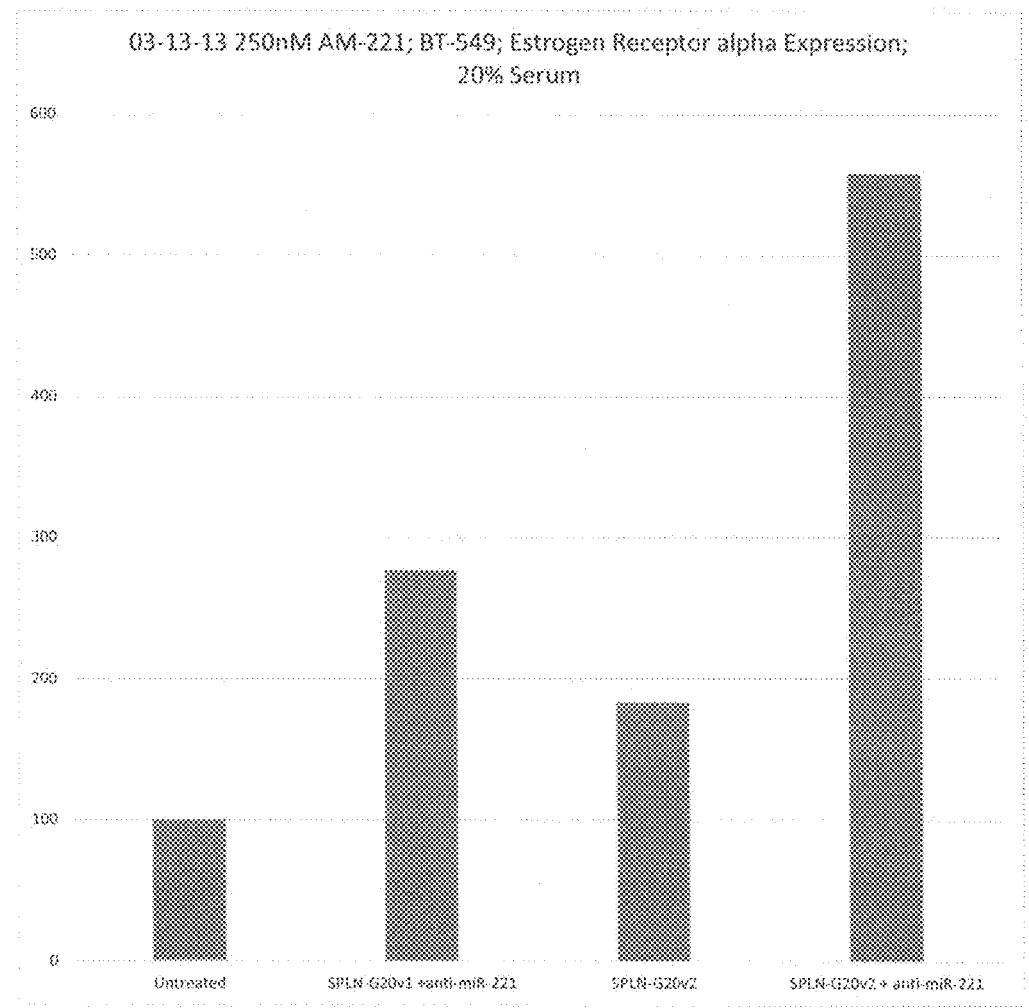
FIG. 26: SPLN-G20 transfection in ERα of BT-549 cells.

Anti-miR-221 was combined with SPLN-G20v1 and SPLN-G20v2 at an N:P of 15:1. BT-549, a triple negative breast cancer cell line, was tested for upregulation of miR-221's downstream targets p27/kip1 (a gene involved in apoptosis regulation) and estrogen receptor alpha (ERα, a gene responsible for expression of the estrogen receptor and thus sensitization to hormone based therapy). Cells were plated in 6-well plates 24 h prior to transfection at a density of $2\times10^4$ cells/cm$^2$ in DMEM/F12 cell culture media supplemented with 5% FBS and 1% penicillin/streptomycin (Life Technologies). At the time of transfection, culture medium was replaced with 20% serum containing media. 20% serum was used to simulate the high serum conditions in vivo. Cells were transfected with appropriate controls or 250 nM anti-miR-221 loaded SPLN-G based formulations for 4 h at 37° C. At the end of the treatment period, cells were washed twice with 1×PBS. Cells were allowed to proliferate for 44 h before the start of RT-PCR. RNA from cells was extracted by TRIzol Reagent (Life Technologies) and cDNA was generated by SuperScript® III First-Strand Synthesis System (Life Technologies) per the manufacturer's instructions. RT-PCR was then performed using SYBR green (Life Technologies) and primers for p27/kip1 and estrogen receptor α. β-actin was used as a reference gene. As demonstrated in FIG. 25, free anti-miR-221 displayed minimal activity while SPLN-G20v1 and SPLN-G20v2 demonstrated ~1.75 and ~2.5-fold upregulation in p27/Kip1 respectively. Similar results were observed for ERα expression, as seen in FIG. 26. SPLN-G20v1 upregulated ERα by nearly 3-fold while SPLN-G20v2 upregulated ERα by over 5-fold. These data show that SPLN-G20v2 is an especially useful nanocarrier for in vivo anti-miR delivery.

Example 8

A lipophilic asialoglycoprotein receptor (ASGR) targeting ligand composed of lactobionic acid (LA), bearing a galactose moiety, and linked to a phospholipid, was synthesized and incorporated into a LN for liver-specific delivery of anti-miR-155. Gramicidin A was also incorporated into the LN to facilitate endosomal release of the anti-miR. This formulation is referred to herein as lactosylated gramicidin-based LN (Lac-GLN). The hepatocyte targeting was evaluated in HepG2 cells and in mice. The physiochemical properties, cellular uptake, in vitro and in vivo delivery efficacy were investigated.

1,2-dioleoyl-3-dimethylammonium-propane (DODAP), and L-α-dioleoyl phosphatidylethanolamine (DOPE) were purchased from Avanti Polar Lipids (Alabaster, Ala.); 1,2-dimyristoyl-sn-glycerol and methoxypolyethylene glycol (DMG-PEG) were purchased from NOF America Corporation (Elysian, Minn.); 1-ethyl-3-[3-dimethylaminopropyl] carbodiimide hydrochloride (EDC) and N-hydroxysuccinimide (NHS) were from Thermo Scientific (Rockford, Ill.). Monomethoxy polyethylene glycol 2000-distearoyl phosphatidylethanolamine (mPEG-DSPE) was obtained from Genzyme Pharmaceuticals (Cambridge, Mass.). Cholesterol, lactobionic acid, gramicidin A and all other reagents were purchased from Sigma-Aldrich (St. Louis, Mo.) without further purification. Firefly Luciferase (GL2+GL3) siRNA (Luci-siRNA) (AM 4629), negative scrambled control (AM 17010), and Lipofectamine 2000 were purchased from Invitrogen (Grand Island, N.Y.).

Anti-miR-155 (sequence: 5'-A\*C\*CCCUAUCACGAUUAGCAUU\*A\*A-3' (SEQ ID NO. 6), containing phosphorothioate linkages (\*) and 2'-O-Methyl), Cy3 labeled anti-miR-155 (Cy3-anti-miR-155), and Cy5.5 labeled anti-miR-155 (Cy5.5-anti-miR-155) were synthesized by Alpha DNA (Montreal, Canada). The Taqman kits for real-time RT-PCR assay of miR-155 (002623) and RNU6B (001093) were purchased from Applied Biosystems (Carlsbad, Calif.).

Lactobionic acid was activated by EDC and converted to its NHS ester, which was then reacted with DOPE to yield n-lactobionyl-DOPE (Lac-DOPE). The product was characterized by Fourier transform infrared (FTIR) spectrometry on a Nexus 470 FTIR Spectrometer (Thermo Scientific, Rockford, Ill.). Lac-GLNs were prepared by the ethanol injection method. The lipid mixture, composed of DODAP, Lac-DOPE, DOPE, DMG-PEG and gramicidin A at a molar ratio of 50:10:28:2:10, was dissolved in ethanol, and rapidly injected into RNAse- and DNAse-free HEPES buffered solution (20 mM, pH 7.4). The resulting lipid nanoparticles were sonicated for 2 min by a bath sonicator and dialyzed against RNAse- and DNAse-free water for 4 hr at room temperature to remove ethanol using a molecular weight cut-off (MWCO) 10,000 Dalton Float-A-Lyzer (Spectrum Laboratories Inc., Ranco Dominguz, Calif.).

The anti-miR-155 containing Lac-GLN was prepared by adding an equal volume of anti-miR-155 dissolved in RNAse- and DNAse-free HEPES buffer to Lac-GLN, followed by brief vortexing for 10 sec and incubation at room temperature for 10 min. The weight ratio of lipids:anti-miR was fixed at 10:1, and the concentration of anti-miR-155 was 1 mg/kg. The resulting nanoparticles were sterilized using 0.22 μm filters (Fisher Scientific, Pittsburgh, Pa.). Control formulations were prepared by the same method.

The particle size of anti-miR-155 containing Lac-GLN was determined by dynamic light scattering on a Model 370 NICOMP Submicron Particle Sizer (NICOMP, Santa Barbara, Calif.) in the volume-weighted distribution mode. Particles were dispersed in cell culture medium. The morphology of Lac-GLN was examined by a FEI Tecnai G2 Bio TWIN transmission electron microscope (FEI Company, OR, USA). Samples were prepared as described above, and a drop of the sample was negatively stained with uranyl acetate for 1 min on a perforated carbon grid for analysis. Images were recorded using a Gatan 791 MultiScan CCS camera and processed by the Digital Micrograph 3.1 software package.

The surface charge of anti-miR-155 containing Lac-GLN was examined in 20 mM HEPES buffer using ZetaPALS zeta potential analyzer (Brookhaven Instruments Corp., Holtsville, N.Y.). Encapsulation efficiency of Lac-GLN was determined by Quant-iT™ RiboGreen RNA Kit (Invitrogen, Grand Island, N.Y.) following the manufacturer's protocol, and the fluorescence intensity (FI) was determined using a luminescence spectrometer (KS 54B, Perkin Elmer, UK) at an excitation of 480 nm and an emission of 520 nm. The encapsulation efficiency was calculated.

The colloidal stability of anti-miR-155 containing Lac-GLN was determined by monitoring changes in its particle size over a 30-day period during storage at 4° C. or 25° C. The serum stability test was used to investigate the ability of Lac-GLN to protect anti-miR from serum nuclease degradation. Anti-miR-155-lac-GLN and free anti-miR-155 were exposed to 50% fetal bovine serum (FBS) and incubated at 37° C. for various time periods. Aliquots of each sample were then loaded onto a 1.5% (w/v) agarose gel containing ethidium bromide.

Human HCC cell lines SK-Hep-1 and HepG2 cells were cultured in DMEM medium supplemented with 10% fetal bovine serum (FBS), 100 U/ml penicillin and 100 μg/ml streptomycin at 37° C. and 5% $CO_2$.

For Luci-siRNA transfection, $2 \times 10^4$ SK-Hep-1 cells stably expressing luciferase, were seeded per well in 800 μl culture medium in 48-well plates and allowed to grow overnight at 37° C. under 5% $CO_2$ atmosphere. Next day, the culture medium was replaced with medium containing 0%, 10% and 20% FBS, and cells were transfected with Luci-siRNA containing Lac-GLN and various control formulations at 100 nM for 4 hr. After transfection, the medium was replaced with fresh medium containing 10% FBS and 48 hrs post transfection cells were washed with PBS and luciferase activity in cell lysates was determined using Luciferase Assay Kit (Promega, Madison, Wis.) following manufacturer's instruction. Briefly, the total amount of protein of each well was determined using BCA Assay Kit (Pierce, Rockford, Ill.), and luciferase activity was determined by normalization to the total amount of protein. The luciferase down-regulation was then calculated as the relative value compared to the untreated negative control.

For anti-miR-155 transfection, HepG2 cells were plated at $2 \times 10^5$ cells per well in 6-well plates with 2 ml cultured medium, and incubated overnight at 37° C. under 5% $CO_2$ atmosphere. Culture medium was then replaced with fresh medium, and cells were transfected with 100 nM anti-miR-155 using Lipofectamine 2000, Lac-GLN, and control formulations and after 4 hr incubation, the medium was replaced with fresh medium. Cells were incubated for an additional 48 hr at 37° C., then miR-155 and its target gene expression level was determined by real time RT-PCR analysis. As a positive control, cells transfected with Luc-siRNA and anti-miR-155 using Lipofectamine 2000 were performed following manufacturer's protocol. Untreated cells and empty Lac-GLN were used as negative controls.

The cytotoxicity of Lac-GLN was evaluated by MTS assay (Promega, Madison, Wis.). HepG2 cells were seeded in 96-well plates at a density of $1 \times 10^4$ cells per well. After overnight incubation, cells were treated with empty Lac-GLN, negative control RNA alone, anti-miR-155 alone, negative control RNA containing Lac-GLN, and anti-miR-155 containing Lac-GLN at RNA concentration of 100 nM for 24 hr. MTS reagent (20 μL was then added to each well, and cells were incubated for another 2 hr. The optical density (OD) at 490 nm of each well was measured using a Multiskan Ascent automatic plate reader. Untreated cells were used as control and defined as 100% viability. Cell viability was calculated as a percentage of the untreated cells.

Analysis of the cellular uptake of Lac-GLN was performed by transfecting fluorescent Cy3-anti-miR-155 in HepG2 cells, and evaluated by confocal microscopy and flow cytometry. For confocal microscopy, $2 \times 10^5$ HepG2 cells per well were seeded in 6-well plates containing a sterile glass coverslip at the bottom of each well (Fisher Scientific, 12-545-82, Pittsburgh, Pa.) and allowed to grow overnight. Cells were then treated with 100 nM Cy3-anti-miR-155 containing GLN, Lac-GLN, and Lac-GLN with 20 mM lactose and 1% BSA for 1 hr at 37° C., followed by a wash step with PBS five times. Cells were fixed with 4% paraformaldehyde for 15 min, and stained with Hoechst 33342 (Invitrogen, Grand Island, N.Y.) and Alexa-488 phalloidin (Invitrogen, Grand Island, N.Y.) for 10 min each at room temperature. The glass coverslip with the cells was then detached from the plates and covered with a regular glass slide. Confocal analysis was performed on an Olympus FV 1000 Filter Confocal Microscope (Olympus Optical Co., Tokyo, Japan).

For the flow cytometric analysis, $2 \times 10^5$ HepG2 cells were treated with 100 nM Cy3-anti-miR-155 containing GLN, Lac-GLN, GLN with 20 mM lactose and 1% BSA, and Lac-GLN with 20 mM lactose and 1% BSA for 1 hr at 37° C. Cells were suspended using 0.25% trypsin, washed with PBS five times, and fixed with 4% paraformaldehyde. The fluorescence intensity was measured on a Becton Dickinson FACScalibur Flow Cytometer (Franklin Lakes, N.J.), and a total of 10,000 events were collected for each sample.

Total RNA from transfected cells or tissue extracts was isolated by TriZol reagent (Invitrogen, Grand Island, N.Y.) and purified by following the standard protocol. The miR-155 cDNA was synthesized using TaqMan MicroRNA reverse transcription Kit (Applied Biosystems, Carlsbad, Calif.), and the cDNA was amplified and quantified using the TaqMan MicroRNA Kit (Applied Biosystems, Carlsbad, Calif.). The cDNA of C/EBPβ and FOXP3 was synthesized using the first-strand cDNA synthesis kit (Invitrogen, Grand Island, N.Y.) and resulting cDNA was amplified and quantified using SYBR Green method (Applied Biosystems, Carlsbad, Calif.).

Primers were designed by the Primer Express Program (Applied Biosystems):

```
C/EBPβ:
forward:
                                            [SEQ ID NO. 7]
5'-AGAAGACCGTGGACAAGCACAG-3, reverse:
                                            [SEQ ID NO. 8]
5'-TTGAACAAGTTCCGCAG GGTGC-3';

FOXP3
forward:
                                            [SEQ ID NO. 9]
5'-AATGGCACTGACCAAGGCTTC-3', reverse:
                                            [SEQ ID NO. 10]
5'-TGTG GAGGAACTCTGGGAATGTG-3';
and GAPDH:
forward:
                                            [SEQ ID NO. 11]
5'-CCCCTGGCCAAGGTCATC CATGACAACTTT-3, reverse:
                                            [SEQ ID NO. 12])
5'-GGCCATGAGGTCCACCACCCTGTTGCTGTA-3'.
``` miR-155 level was normalized to that of RUN6B, while C/EBPβ and FOXP3 levels were normalized to that of GAPDH. Their expressions were calculated using the $2^{-\Delta CT}$ approach.

Fluorescent Cy3-anti-miR-155 containing GLN and Lac-GLN were used for confocal microscopy analysis. Male C57BL/6 mice were given Cy3-anti-miR-155 (50 µg) containing GLN and Lac-GLN intravenously with a total injection volume of 200 µl. After 4 hr, mice were sacrificed and tissues were collected. Harvested tissues were fixed in 4% paraformaldehyde for 6 hr and soaked in 30% sucrose overnight at 4° C. Tissues were then transferred to block holders, embedded with O.C.T. freezing medium (Fisher Scientific, Pittsburgh, Pa.), and frozen in liquid nitrogen. Tissue samples were processed for tissue sectioning, and stained with Hoechst 33342 (Invitrogen, Grand Island, N.Y.) and Alexa-488 phalloidin (Invitrogen, Grand Island, N.Y.) for 10 min each at room temperature. The Fluorescent images were captured using an Olympus FV 1000 Filter Confocal Microscope (Olympus Optical Co., Tokyo, Japan).

Fluorescent Cy5-anti-miR-155 containing GLN and Lac-GLN were used for measuring in vivo uptake in different tissues by IVIS imaging. The same treatment as described above was applied for this experiment. Whole tissues were harvested and fixed in 4% paraformaldehyde for 6 hr and immersed in 30% sucrose for 12 hr at 4° C. Whole tissue Cy5 fluorescent signals were measured using Xenogen IVIS-200 Optical In Vivo Imaging system (Caliper Life Sciences, Hopkinton, Mass.).

Negative control RNA or anti-miR-155 containing Lac-GLN and other controls were administered to male C57BL/6 mice by intravenous injection at a dose of 1.5 mg/kg. 48 hr post administration, mice were anesthetized, and liver tissues were harvested and immediately frozen in liquid nitrogen. RNA extraction and RT-PCR were performed as described in the previous section.

Results were reported as mean±standard deviation, and a minimum of triplicates were performed for each experiment. Comparisons between the groups were analyzed by Student's t test for two groups or ANOVA for multiple groups. Results were considered as statistically significant when p values were <0.05. All the statistical analysis was performed by Microsoft Excel 2003 software.

Figure 27:
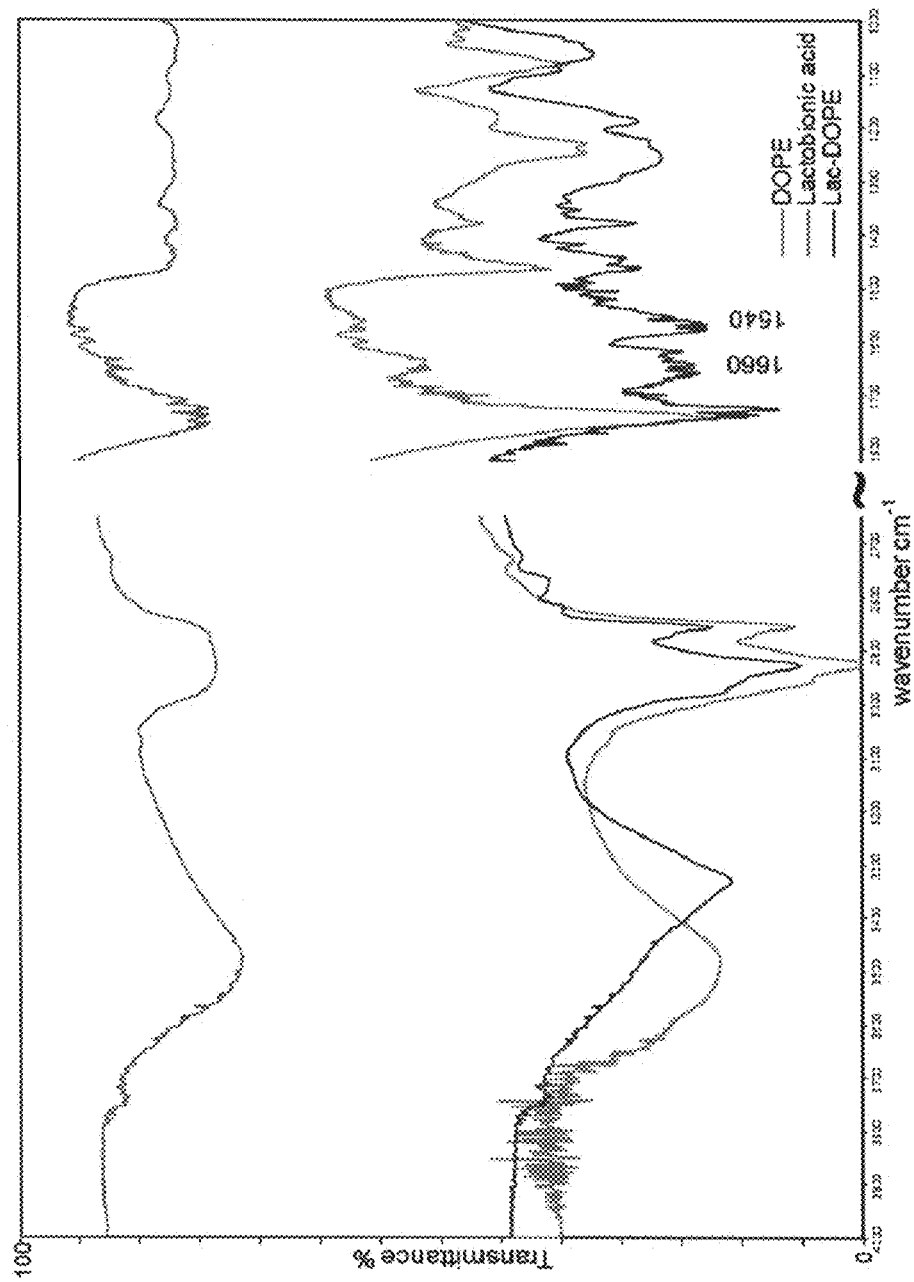
FIG. 27: FTIR spectra of Lac-DOPE (blue), DOPE (red), and lactobionic acid (green).

FTIR was used to confirm the formation of the conjugate. FIG. 27 is an FTIR spectrum of Lac-DOPE, DOPE, and lactobionic acid. The absorption peaks of lac-DOPE are in blue at 1660 cm$^{-1}$ and 1540 cm$^{-1}$, indicating amide bond formation.

Figure 28A:
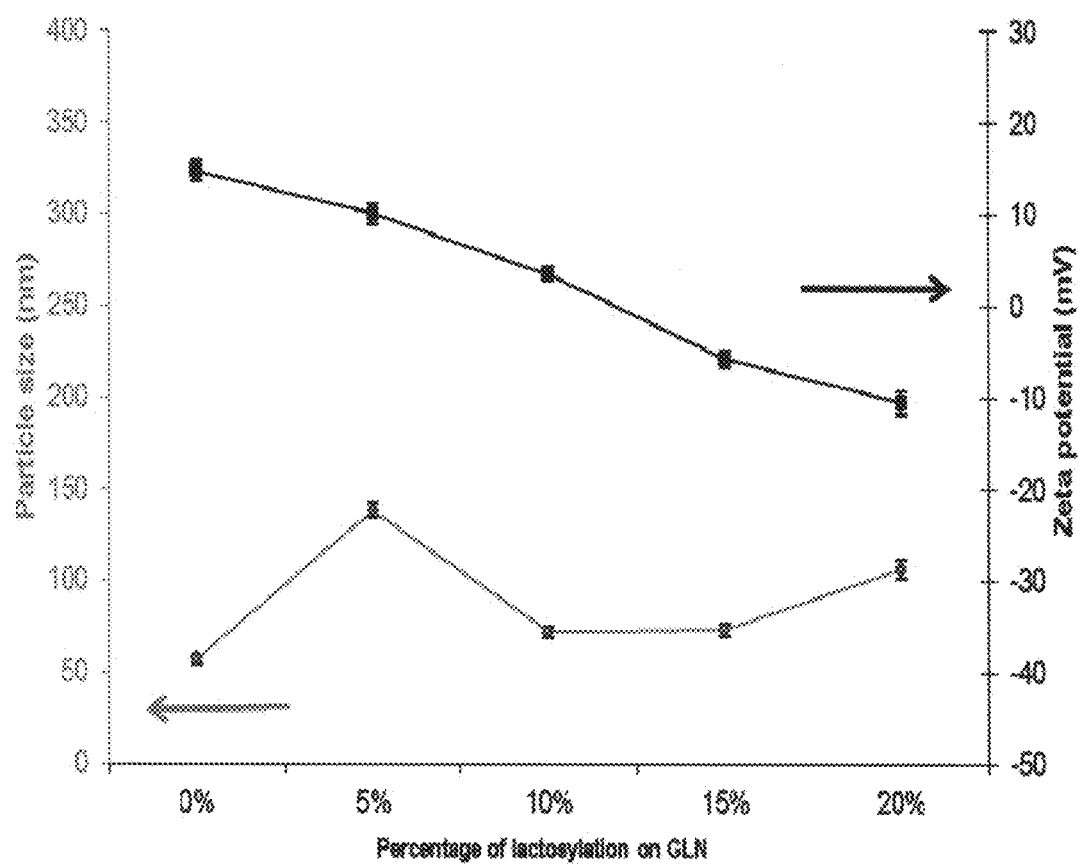
FIGS. 28A-B: Characterization of Lac-GLN.
Figure 28B:
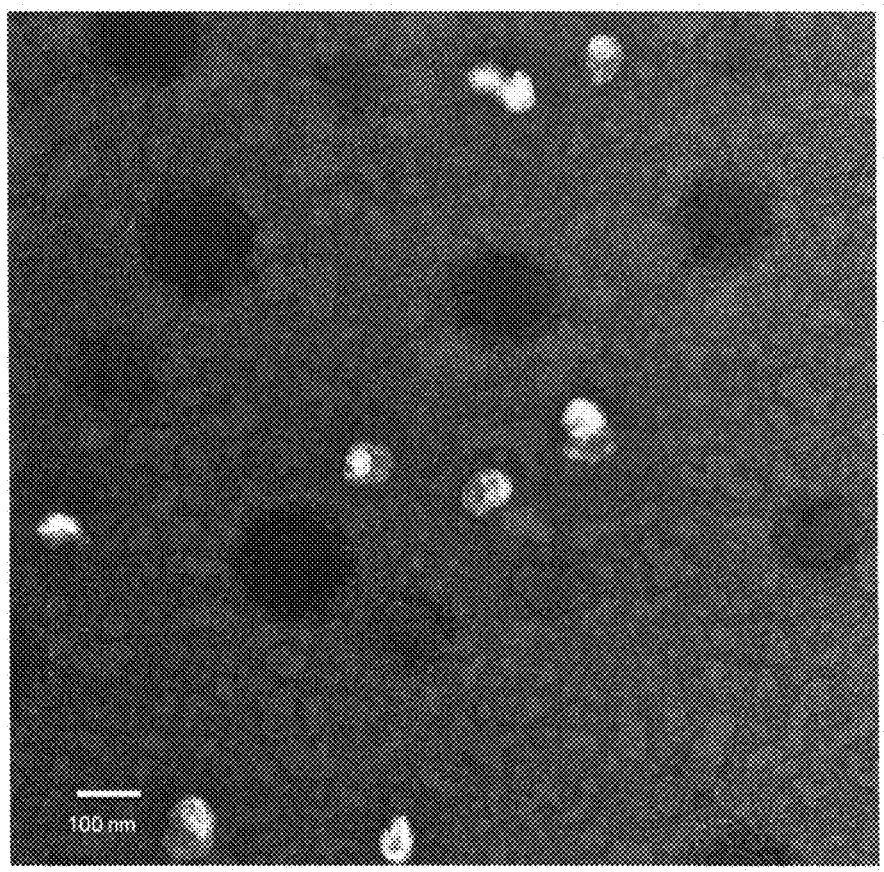

The particle size and zeta potential of GLN with various molar percentages of Lac-DOPE were evaluated and this characterization is shown in FIGS. 28A-B and 29A-B. 10% Lac-DOPE in the formulation was the optimal composition with an average diameter of 72.66 nm and a zeta potential of 3.49 mV. This composition was selected as the delivery vehicle for the following experiments and termed Lac-GLN. The size and morphology of Lac-GLN was further examined by TEM. The image in FIG. 28B shows the spherical shape and a uniform size distribution of Lac-GLN with less than 100 mm diameter, which was in accordance with data obtained by DLS.

Figure 29A:
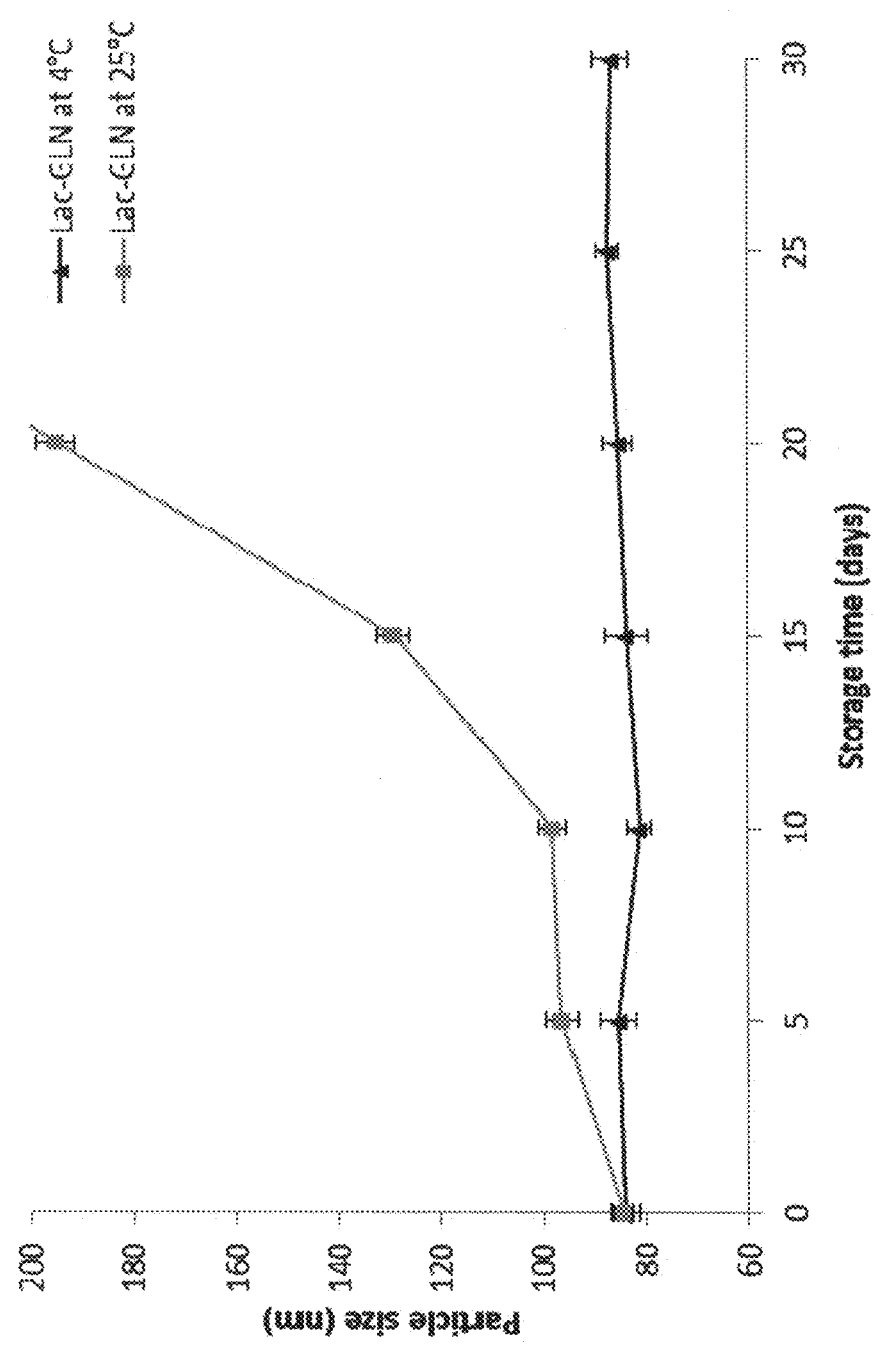
FIGS. 29A-29B: Characterization of Lac-GLN.
Figure 29B:
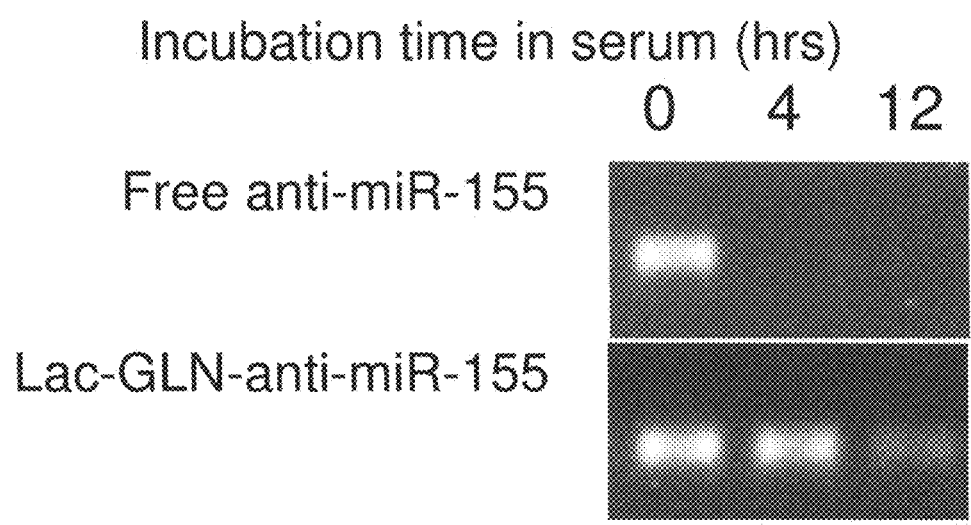

The encapsulation efficiency was calculated from the particle's ability to condense oligonucleotides. As shown in FIG. 30, the encapsulation efficiency of Lac-GLN was >85%. The colloidal stability was determined by monitoring the change of particle size over time. As shown in FIG. 29A, the average diameter of Lac-GLN remained unchanged over a 30 day period at 4° C., but a significant increase in the average diameter was observed under storage at 25° C.

Figure 31:
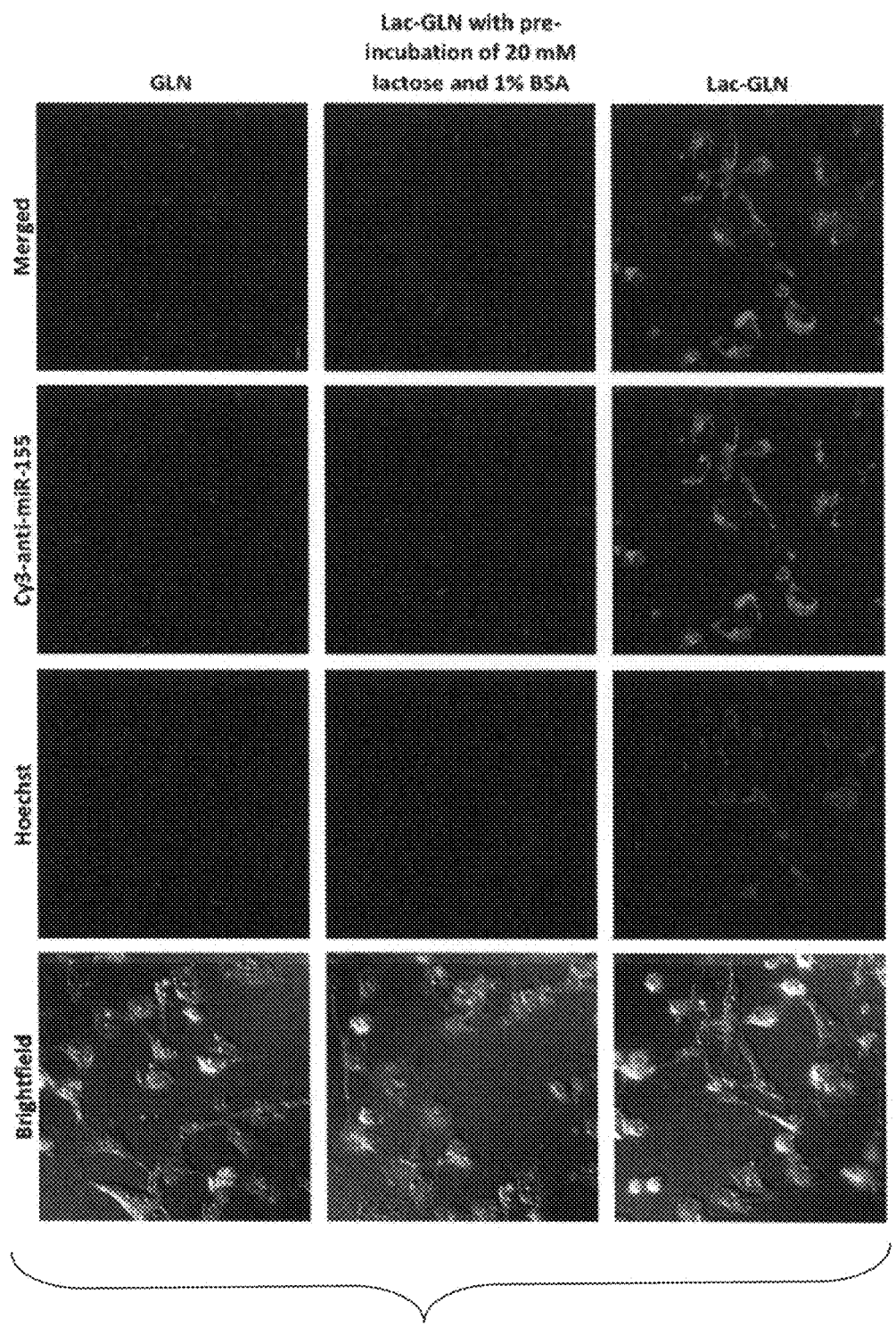
FIG. 31: Cellular uptake of Cy3-anti-miR-155 containing Lac-GLN and other control formulations in HepG2 cells as determined by confocal microscopy.

The ability of Lac-GLN to protect anti-miR was evaluated by a serum stability test. In this test, free anti-miR and anti-miR-155-Lac-GLN were mixed with FBS and culture at 37° C. for different time periods. As shown in FIG. 31, Lac-GLN was able to protect anti-miR-155 from nuclease degradation for up to 12 hrs, while free anti-miR-155 was completely digested within 4 hr serum incubation. This result demonstrated good serum stability for Lac-GLN.

The delivery efficiency was first examined by comparing the performances of GLN and Lac-GLN in HCC cell-specific uptake. HepG2 cells with a high expression of ASGR on the surface were treated with Cy3-anti-miR-155 containing non-targeted GLN and ASGR-targeted Lac-GLN. The pre-incubation with 20 mM lactose and 1% BSA was applied to block ASGR-mediated and non-specific uptake, respectively. Cells were evaluated by confocal microscopy. As shown in FIG. 29, cells treated with Lac-GLN showed a significantly stronger fluorescence signal than those treated with non-targeted GLN. This uptake enhancement was reduced in cells pretreated with blocking agents, which demonstrated that the cellular uptake of Lac-GLN was ASGR-specific. This result indicated a successful ASGR targeting of Lac-GLN.

Cellular uptake of GLN and Lac-GLN was further quantified by flow cytometry. As shown in FIG. 30A, the uptake of Lac-GLN was about 3.58-fold higher than that of non-targeted GLN in HepG2 cells. The fluorescence signal did not reduce significantly in the GLN pretreated cells with 20 mM lactose and 1% BSA, indicating non-specific uptake of GLN by HCC cells (FIG. 30C). However, the uptake of Lac-GLN was reduced by 3.51-fold in cells pre-incubated with blocking agents while in absence of blocking agents the uptake between GLN and Lac-GLN treated cells was comparable (FIG. 30B). This result further confirmed that ASGR-targeted delivery improved cellular uptake in HCC cells.

Figure 32A:
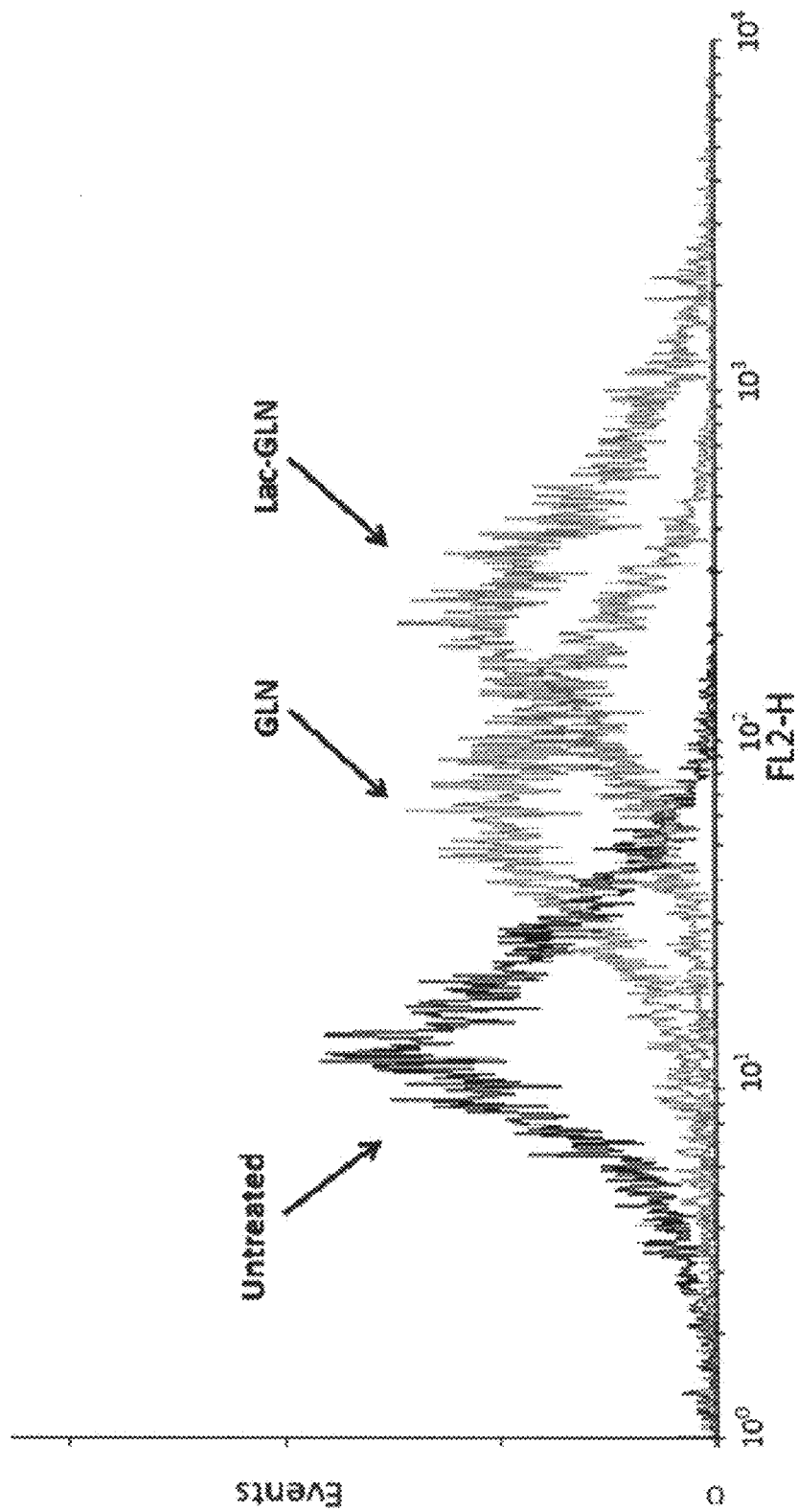
FIGS. 32A-C: HepG2 cells were treated with GLN, Lac-GLN, or Lac-GLN pre-incubated with 20 mM lactose and 1% BSA. Fluorescence signals were measured on a FACSCalibur flow cytometer.
Figure 32B:
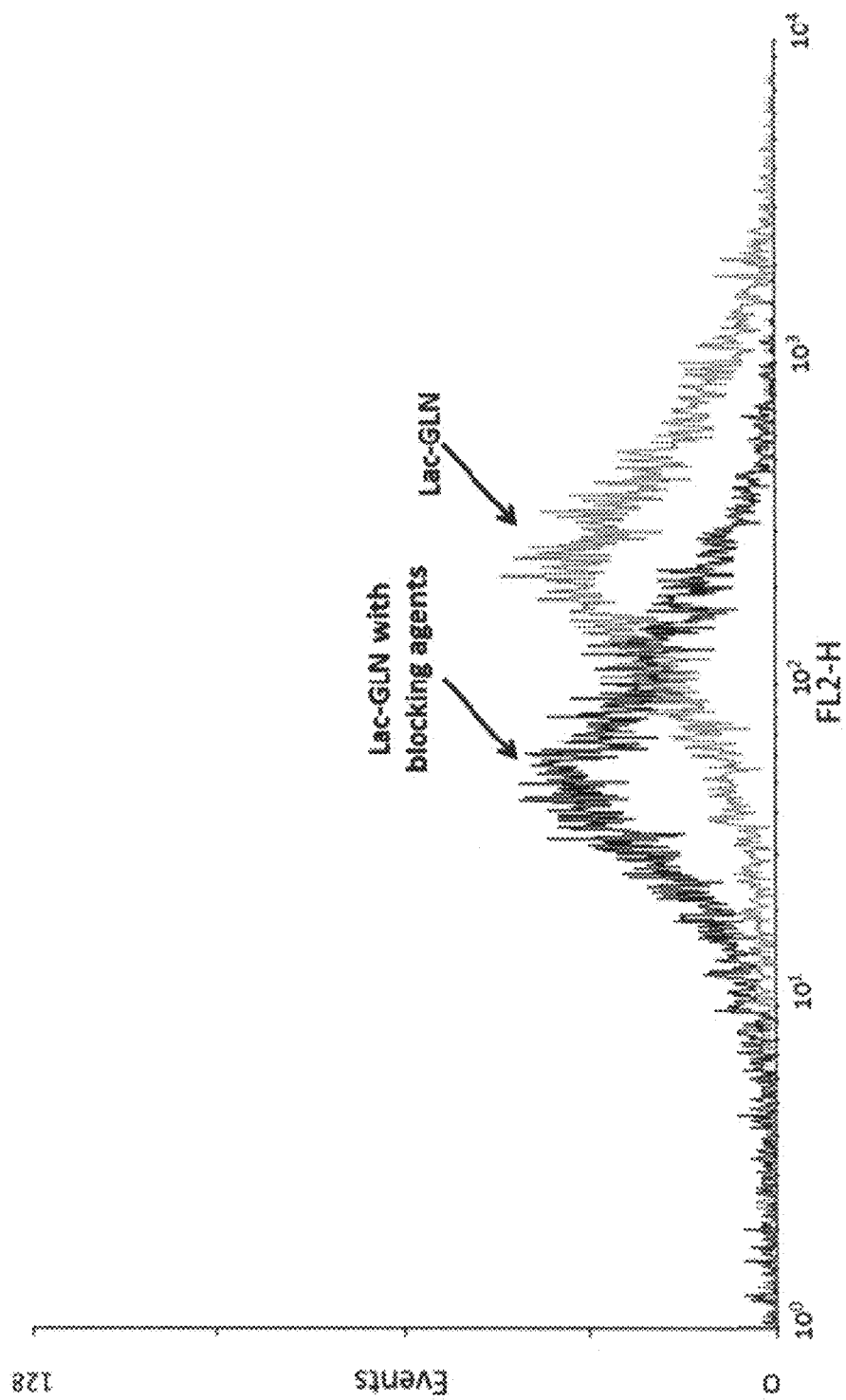
Figure 32C:
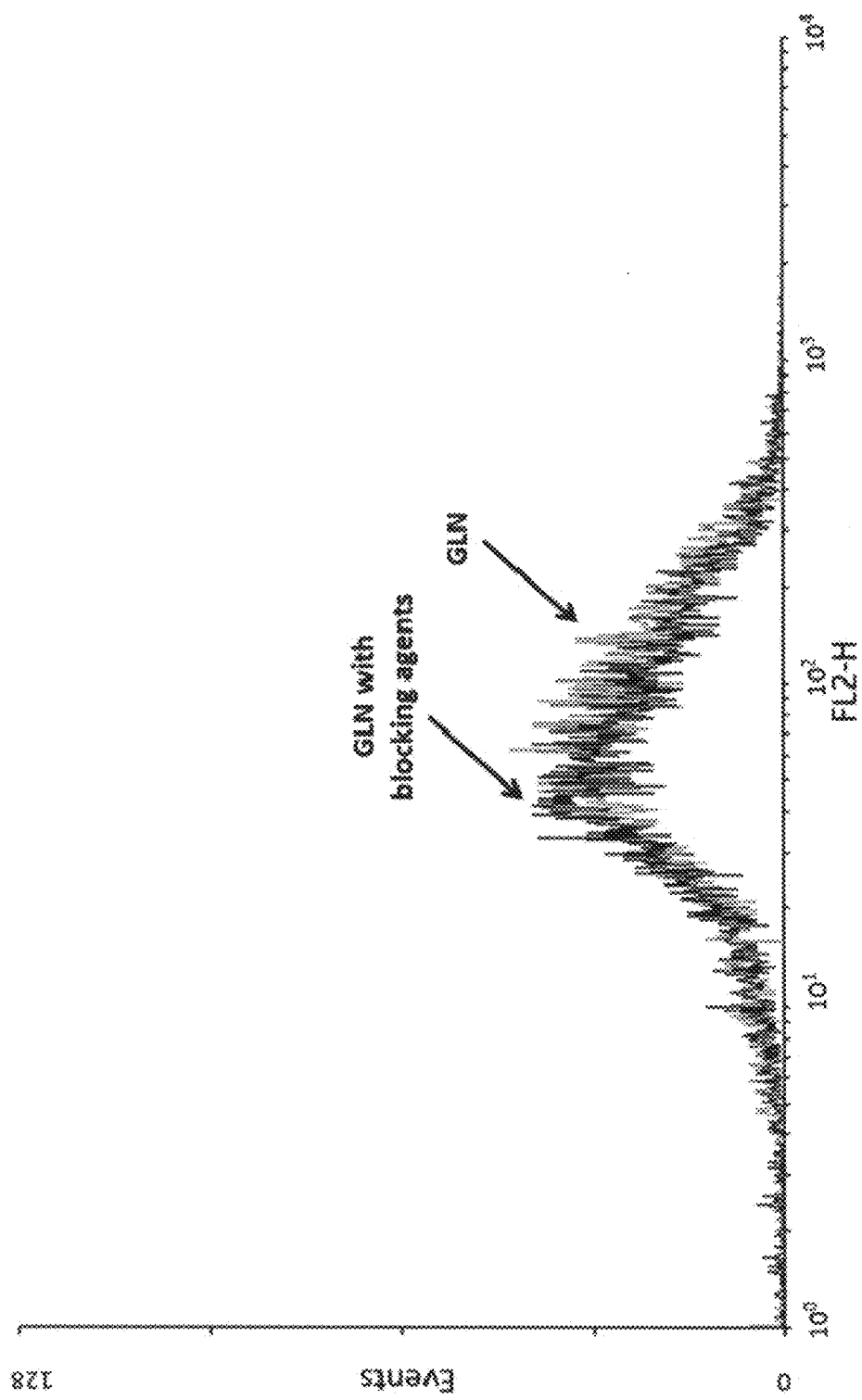

HCC SK-Hep1 cells, stably expressing firefly luciferase mRNA, were used to determine the transfection efficiency of different vehicles and the effect of several factors on transfection efficiency including targeting ligand, gramicidin A, and serum, by analyzing the silencing ability of siRNAs targeting luciferase gene. FIG. 32A shows a significantly lesser expression of luciferase in Lac-LN treated group (78.95%) compared to that in the LN treated group (96.35%) in FBS-free medium, which confirmed the advantage of ASGR-targeted strategy. However, media containing 20% FBS affected this transfection efficiency by only 6%. Treatment with the commercial Lipofectamine 2000 caused 7.84% reduction in luciferase expression, close to the LN treated group, and this transfection was strongly inhibited by serum at high concentration. Moreover, the effect of increasing concentration of gramicidin A as a competitor was analyzed. Surprisingly, in the Lac-GLN treated groups, neither 5% nor 10% gramicidin A was affected by the presence of FBS during transfection. This finding was in contrast to the previously reported studies, where transfection activities were sensitive to the presence of serum. Similar results were obtained in HepG2 cells (data not shown). Thus, this Lac-GLN formulation was advantageous since serum was the main barrier for in vivo delivery in a clinical setting.

Figure 33A:
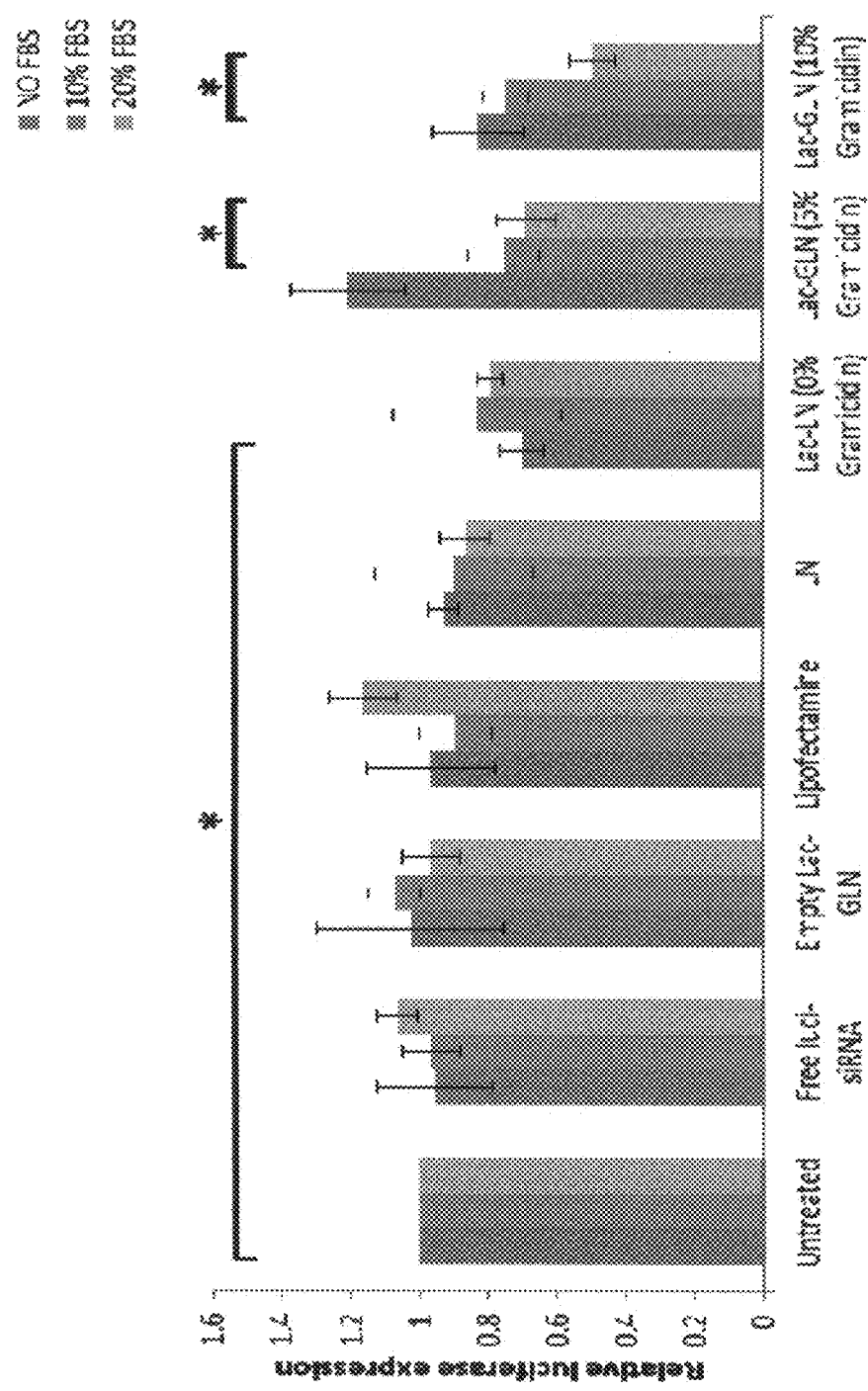
FIGS. 33A-33C: In vitro delivery of Lac-GLN and other formulations.
Figure 33B:
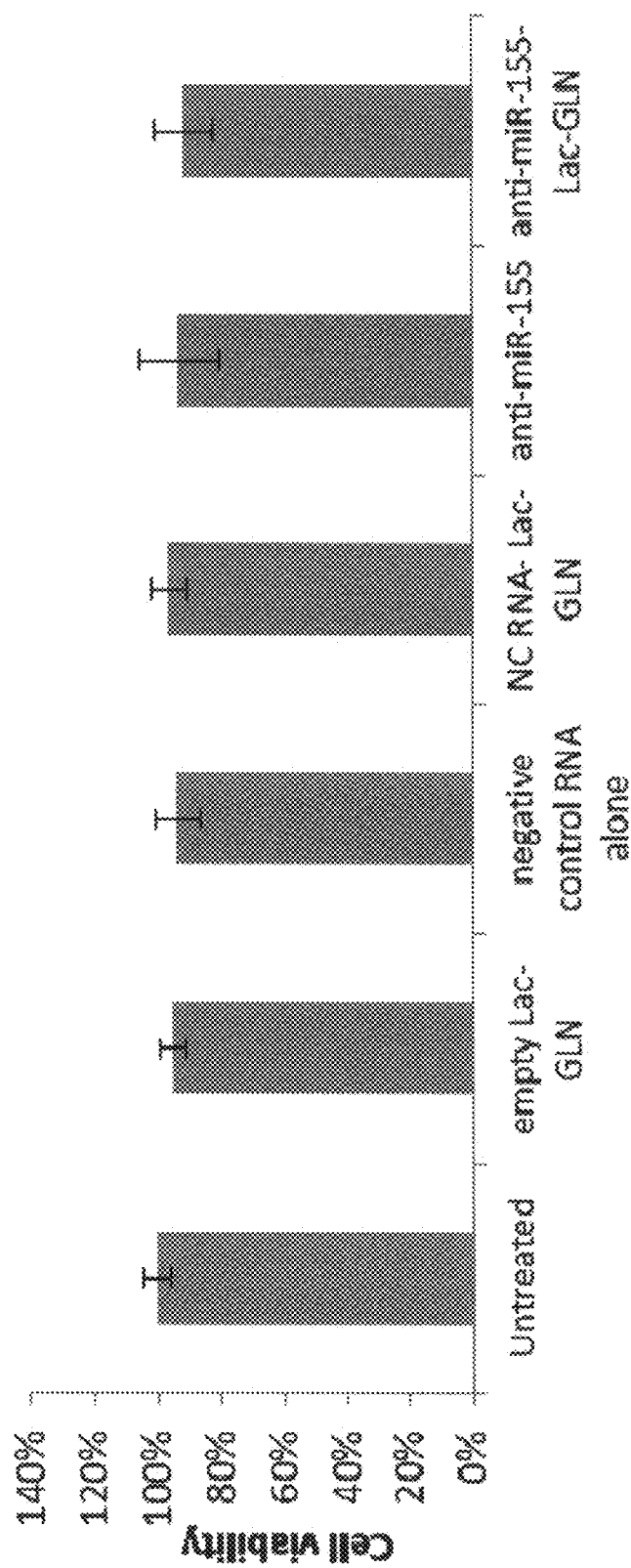

To assess the application of this vehicle in further in vitro and in vivo delivery, its cytotoxicity was first investigated on HCC cells. HepG2 cells were treated with equal amount of empty Lac-GLN, negative control RNA alone, anti-miR-155 alone, negative control RNA-Lac-GLN, and anti-miR-155-Lac-GLN. As shown in FIG. 33B, no significant change in cell viability was observed between treated cells and untreated cells. This result revealed a low cytotoxicity of Lac-GLN in HepG2 cells.

Figure 33C:
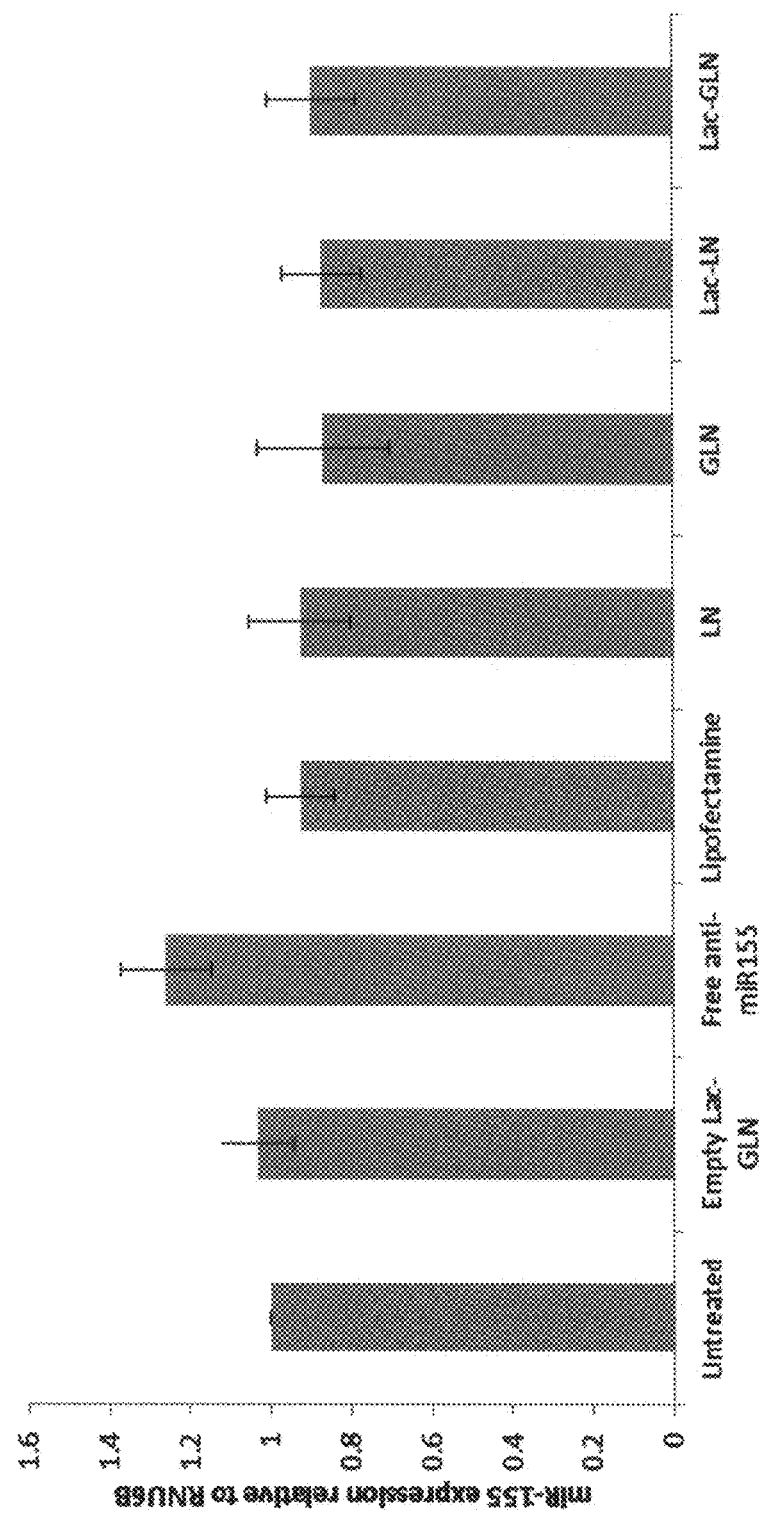
Figure 34A:
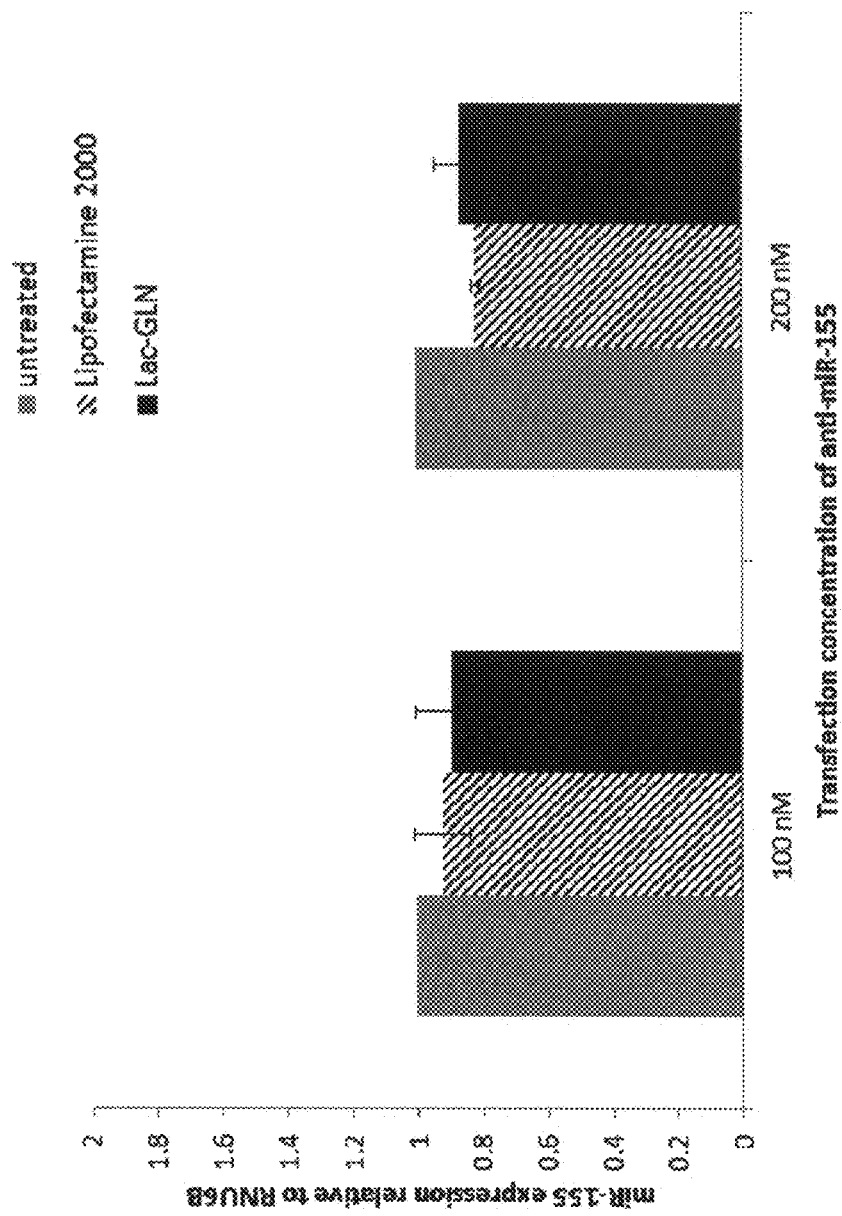
FIGS. 34A-B: In vitro evaluation of different concentrations of anti-miR-155 treatments on miR-155 and target gene expression.

Next, the effects of Lac-GLN containing anti-miR-155 on miR-155 and its downstream targets expression were evaluated in HepG2 cells. Cells were treated with anti-miR-155 containing Lac-GLN and other control formulations for 4 hr, and the miR-155 and its targeting gene expression was measured 48 hr after transfection by real time RT-PCR. FIG. 33C shows the miR-155 expression level from different treatment groups relative to the untreated group. The positive control, treated with Lipofectamine 2000, had 92.4% miR-155 expression of the untreated. In addition, LN, GLN, Lac-LN and Lac-GLN treated groups exhibited a similar miR-155 expression level to that of Lipofectamine 2000 treated group, and the differences among these groups were small. Based on the minor difference in miR-155 expression between the positive control and Lac-GLN treatment group, a doubled anti-miR-155 concentration was applied to examine whether the down-regulation of miR-155 was anti-miR-155 concentration-dependent. As shown in FIG. 34A, the miR-155 expression in the Lipofectamine 2000 treated group changed from 92.4% to 89.5% when the concentration of anti-miR-155 was doubled from 100 nm to 200 nM. This difference between the two treatments was still not statistically significant. In the Lac-GLN treated group, a similar trend was observed, where the expression of miR-155 was 87.2% and 82.9% in 100 nM and 200 nM anti-miR-155 treatments, respectively. These indicated that the miR-155 expression did not depend on anti-miR-155 concentration and anti-miR-155 delivery did not lead to miR-155 degradation.

Figure 34B:
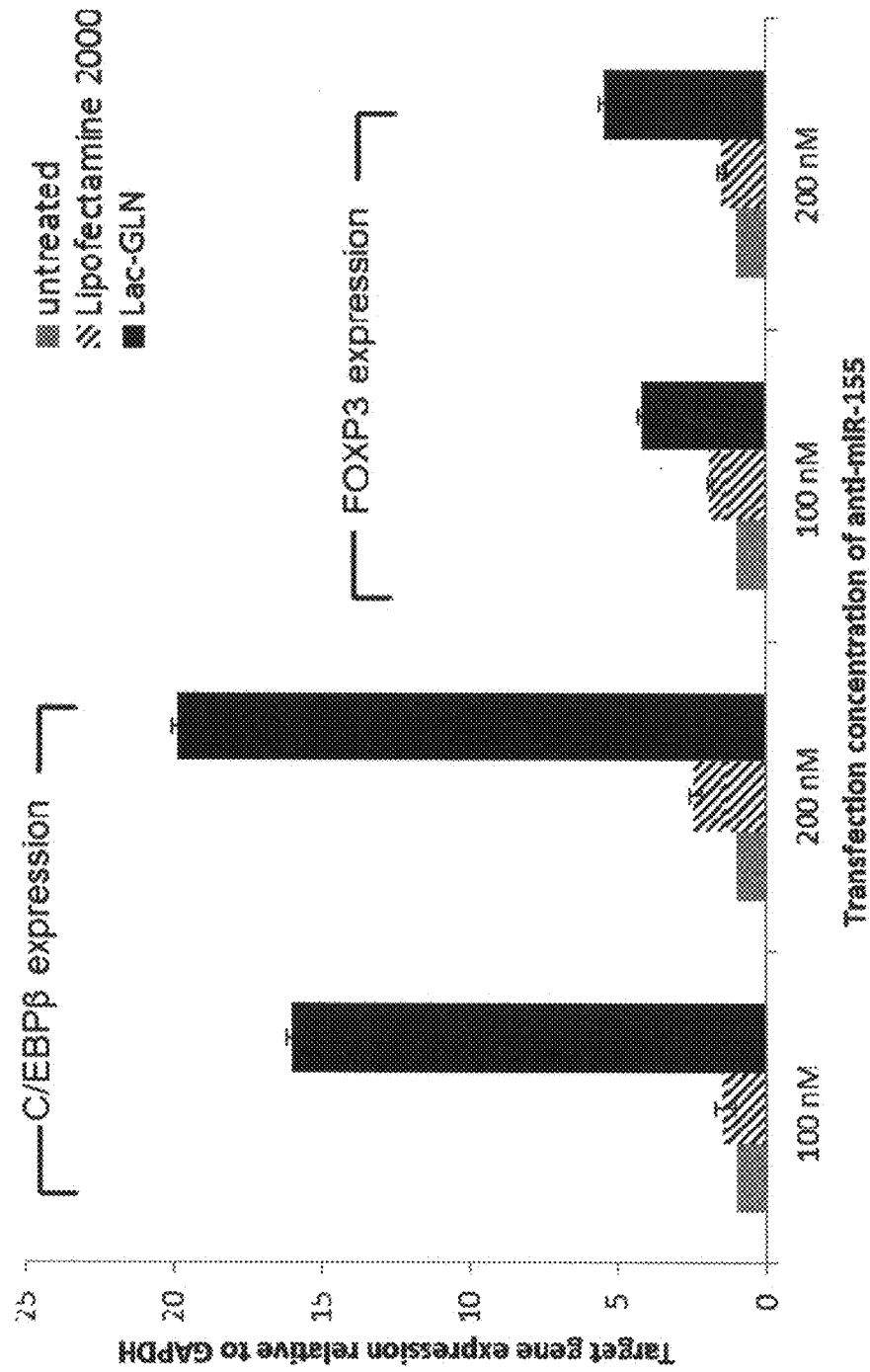

To further examine the delivery efficiency, the expression of miR-155 targeting genes, C/EBPβ and FOXP3, were evaluated. The results are summarized in FIG. 34B. In contrast to the steady expression of miR-155 (FIG. 32A), there were a 16.1- and 4.1-fold increase in C/EBPβ and FOXP3 expression, respectively, in the Lac-GLN 100 nM anti-miR-155 treatment group. Only a 1.4-, 1.9-fold increase of C/EBPβ and FOXP3 expression was observed in cells transfected with Lipofectamine 2000, respectively. Furthermore, doubling the anti-miR-155 concentration resulted in an improved up-regulation of C/EBPβ and FOXP3 expression, clearly demonstrating that the miR-155 targeting gene expression was dependent on anti-miR-155 concentration. Thus, the delivery of anti-miR-155 most likely resulted in functional inhibition of miR-155 rather than its degradation. In sum, these results show Lac-GLN's superiority over the commercial available agent in anti-miR delivery.

Figure 35A:
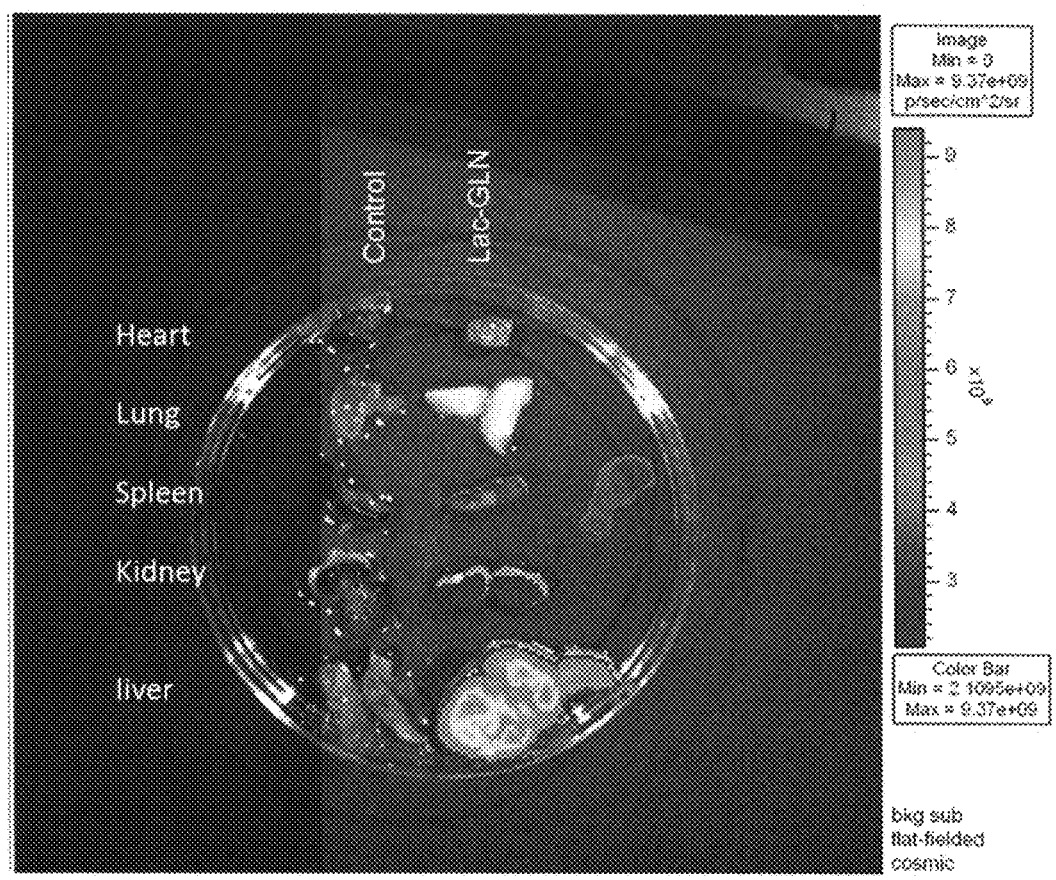
FIGS. 35A-35B: Tissue distribution of Cy5-anti-miR-155 containing GLN and Lac-GLN. Heart, lung, spleen, kidney, and liver were harvested from C57BL/6 mice 4 hr after intravenous administration of Cy5-anti-miR-155 containing GLN or Lac-GLN. Cy5 fluorescence signals were measured by IVIS Imaging System.
Figure 35B:
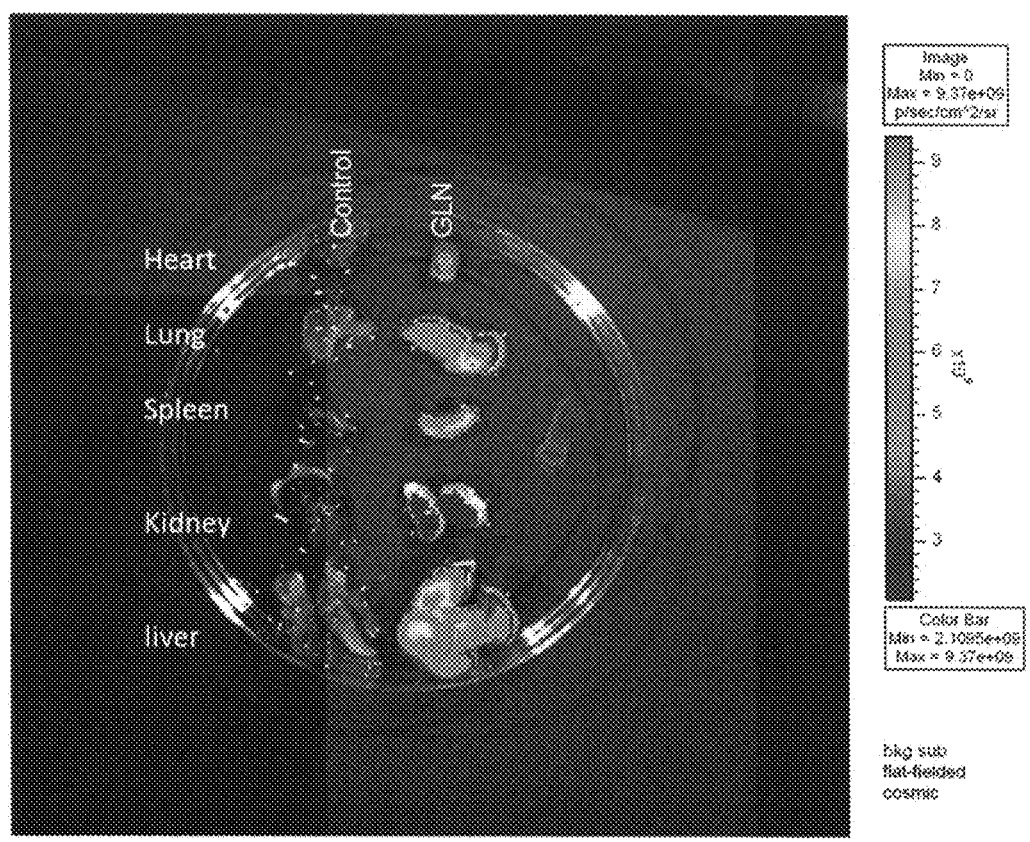

In order to assess the in vivo delivery efficiency and tissue specificity of Lac-GLN, tissue distribution study was performed in C57BL/6 mice that were administrated Cy5-anti-miR-155 containing GLN and Lac-GLN intravenously at a dose of 1.5 mg/kg. After 4 hr, organs were harvested and fluorescence signals were compared. As shown in FIG. 35, lung, spleen and liver were the major organs exhibiting fluorescence signals when mice were injected with non-targeted GLN. In contrast, maximal fluorescence signals accumulated in the liver when mice were treated with Lac-GLN with very weak signals in the spleen and kidney and no detectable signal in lung. These results show that the delivery of Cy5-anti-miR-155 by Lac-GLN was liver-specific and that Lac-GLN was able to minimize off-target uptake, thus improving the overall delivery efficiency.

Figure 36A:
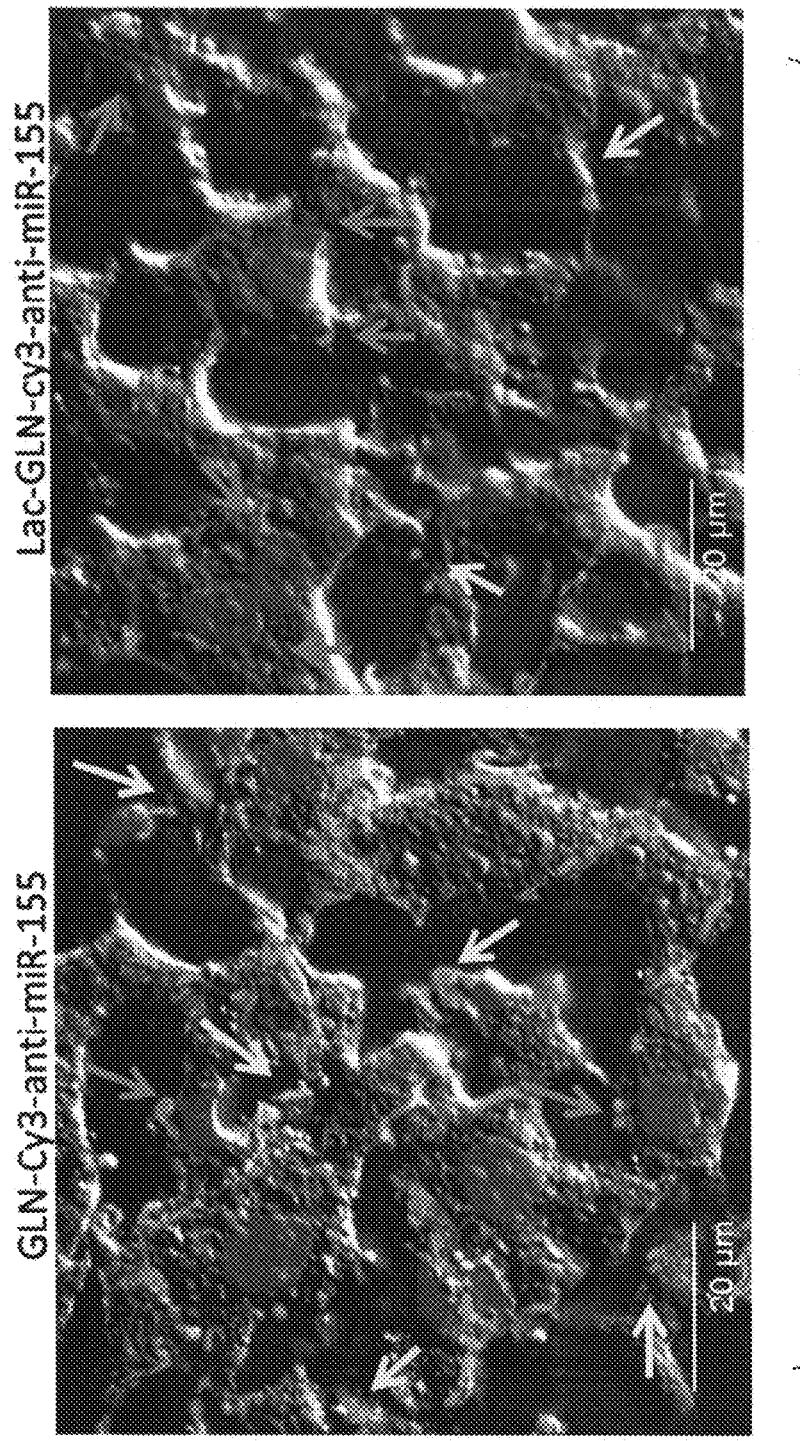
FIGS. 36A and 36B: Confocal microscopy of Cy3-anti-miR-155 containing GLN and Lac-GLN in liver and other organs.

Confocal microscopy was performed on the liver and other organs to further evaluate the delivery efficiency between GLN and Lac-GLN. Besides hepatocytes, the liver also contains a large population of Kupffer cells, known as residential macrophage. As shown in FIG. 36A, a larger proportion of fluorescence signals was taken up by hepatocytes than by Kupffer cells in liver when mice were treated with Lac-GLN, while the uptake was predominantly by Kupffer cells in the non-targeted GLN-Cy5-anti-miR-155 treated liver.

Figure 36B:
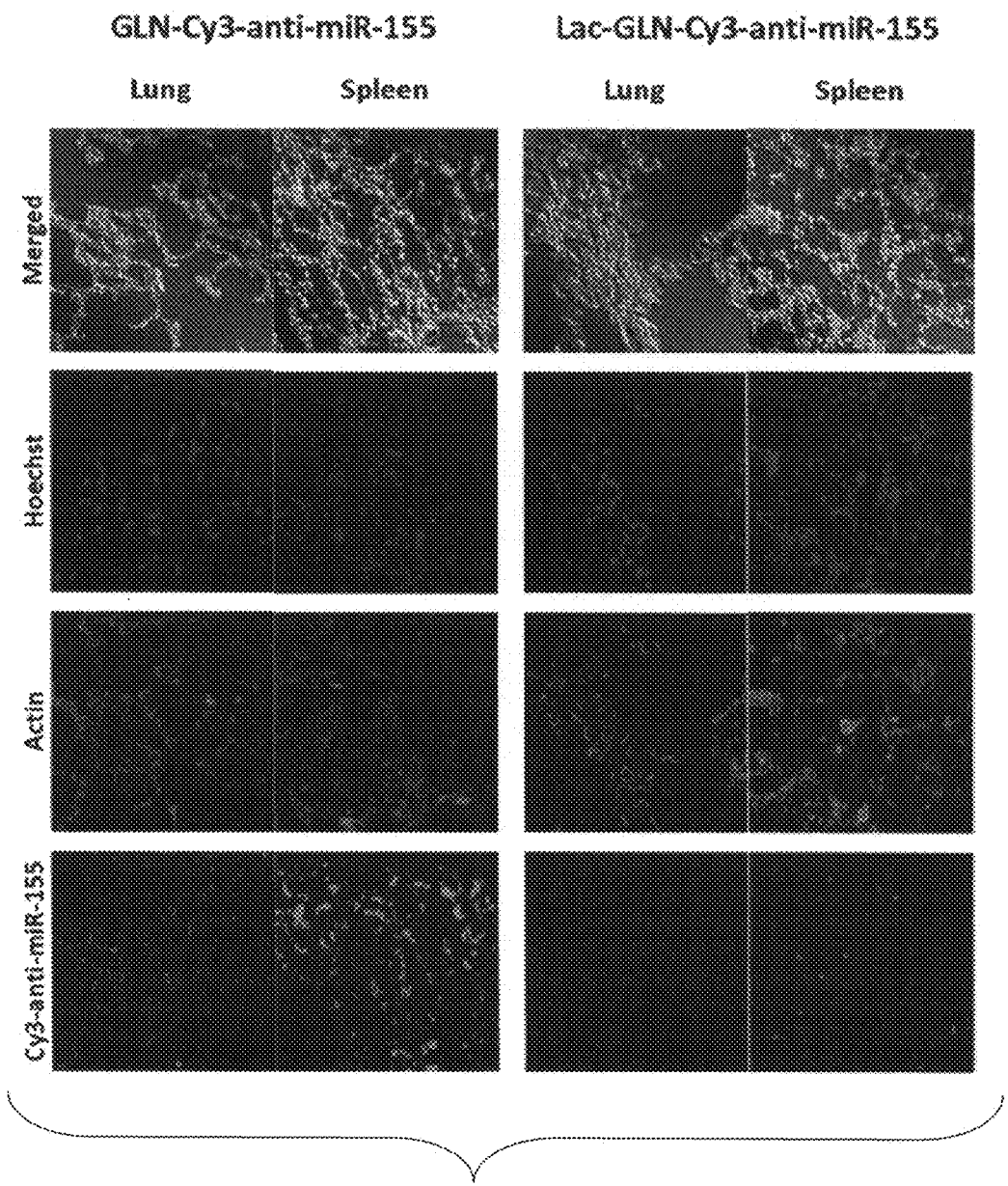

The distribution of fluorescence signals in lung and spleen were also examined to evaluate Lac-GLN delivery. As shown in FIG. 36B, fluorescence signals accumulating in lung and spleen in the Lac-GLN treated mice were less than those in the GLN treated mice, indicating high specificity of Lac-GLN for delivery to the liver.

Figure 37A:
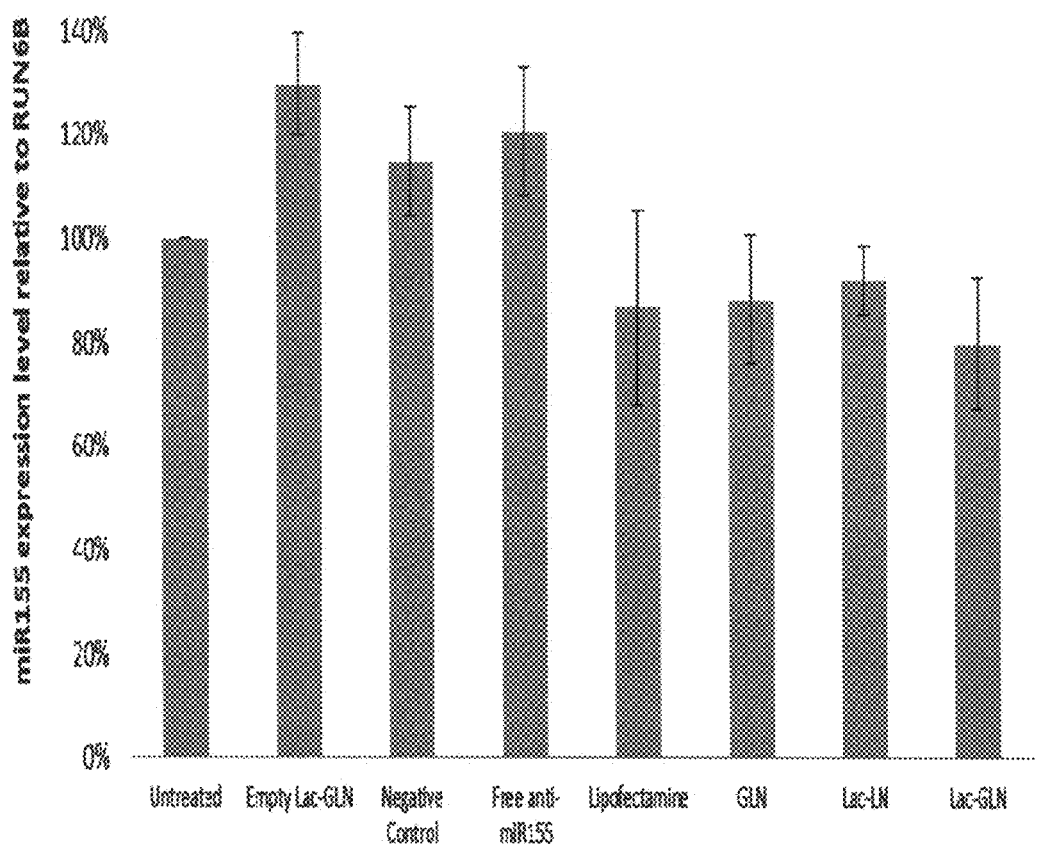
FIGS. 37A-C: In vivo evaluation of anti-miR-155 treatments on miR-155 and target gene expressions. C57BL/6 mice were treated with 1.5 mg/kg anti-miR-155 containing Lac-GLN and control formulations. 4 hr after intravenous administration, liver tissues were harvested and RNA was extracted. Each value represents the mean±SD of three measures.
Figure 37B:
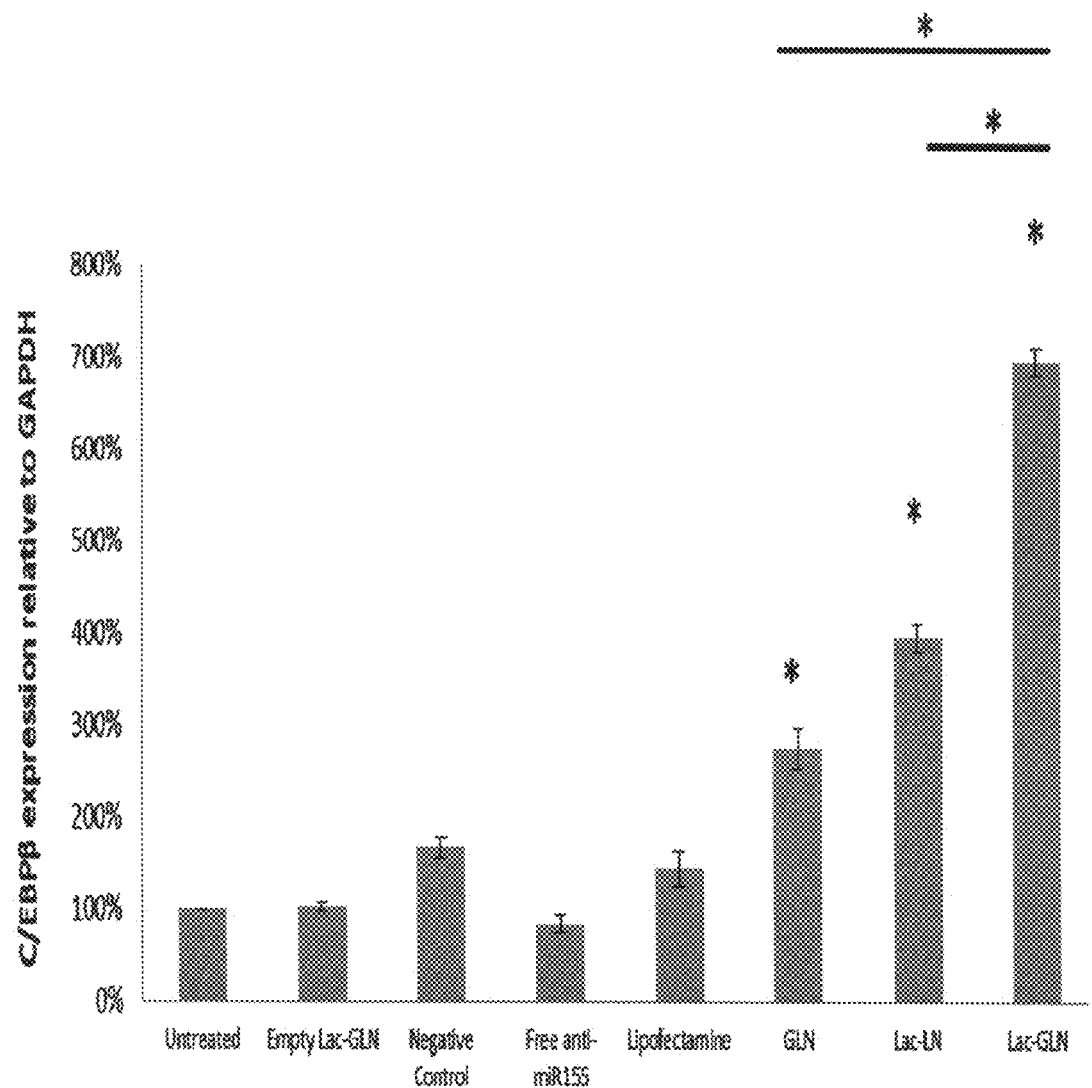
Figure 37C:
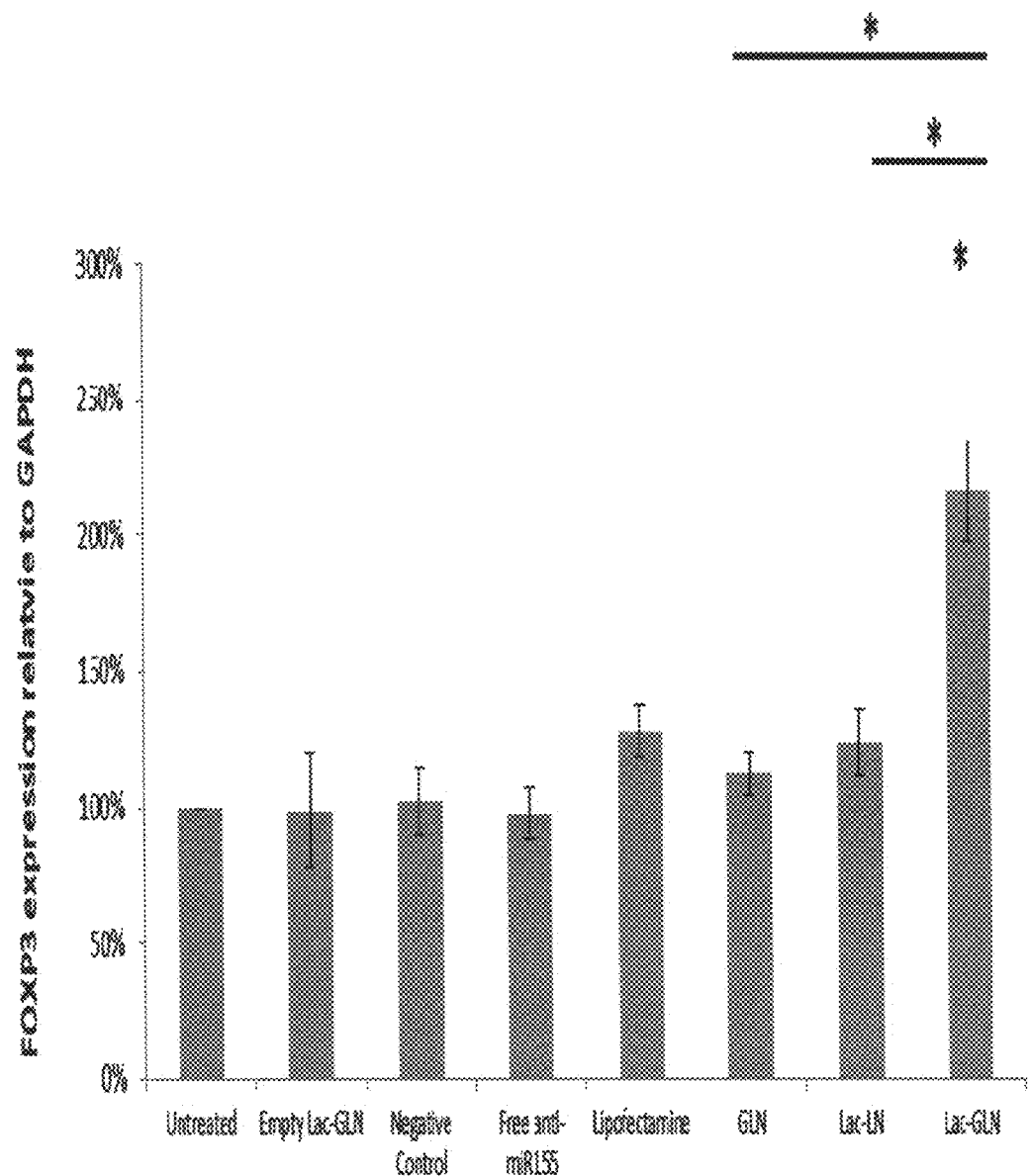

Next, the delivery efficiency of Lac-GLN-anti-miR-155 in C57BL/6 mouse liver was studied. For this purpose, mice were injected a single dose of 1.5 mg/kg anti-miR-155 formulated in Lipofectamine 2000, GLN, Lac-LN or Lac-GLN through tail vein. Injections of empty Lac-GLN, negative control RNA containing Lac-GLN or free anti-miR-155 were used as negative controls. 48 hr post administration, mice were sacrificed and livers were harvested. The expression of miR-155 and its target, C/EBPβ, was evaluated by real time RT-PCR. FIG. 37A illustrates the expression of miR-155. As noted, miR-155 level was not altered in the negative control groups. A slight decrease in miR-155 expression by 13% and 20% was observed when anti-miR-155 was delivered using Lipofecamine 2000 and Lac-GLN, respectively, compared to the untransfected control. Moreover, the differences among GLN, Lac-LN and Lac-GLN were not significant. On the contrary, the delivery efficiency reflected by C/EBPβ expression varied considerably among these groups as demonstrated by a 2.8-, 3.7- and 6.9-fold increase in its expression in GLN, Lac-LN and Lac-GLN treated groups, respectively, compared to the untreated group (FIG. 37B). No significant changes were observed in the negative control groups, and the Lipofectamine 2000 treated group only exhibited a 1.4-fold up-regulation of C/EBPβ. In addition, another miR-155 target gene, FOXP3 expression, was increased by 1.1-, 1.2-, and 2.1-fold in GLN, Lac-LN and Lac-GLN treated groups, respectively (FIG. 37C). These data demonstrate the improvement of delivery efficiency by Lac-GLN and agree with the results of in vitro experiments (FIG. 34).

Example 9 cRGD-PEG-DSPE conjugates were synthesized. cRGDfC and PEG-DSPE-maleimide was conjugated via —SH and -maleimide reaction resulting in a thioether linkage. The cRGDfC and PEG-PSPE-maleimide molar ratio used during the reaction was 1.5:1. cRGDfC and PEG-DSPE-maleimide was each dissolved in PBS buffer containing 5 mM EDTA (pH=7.0). The cRGDfC and PEG-DSPE solutions were combined and reacted at room temperature for 6 h with stirring. The product was purified by gel filtration on a PD-10 column to remove unreacted/excess cRGDfC from the product. For scaled-up reactions, the gel filtration can be replaced with GPC, dialysis using MWCO 2000 membrane, or tangential flow diafiltration. The product can be frozen or lyophilized for long-term stability. The product purity was confirmed by HPLC and by LC-MS. Minimum cRGDfC conjugation level (e.g., 80%) and free peptide content (e.g., <1%) can be established as specifications. The cRGDfC content in the product can be determined by BCA protein assay.

Certain embodiments of the formulations and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A nanoparticle comprising:
a combination of tertiary and quaternary amine-based cationic lipids,
wherein said combination consists of the tertiary amine-cationic lipid present at about 40.0 molar percent; wherein the tertiary amine-cationic lipid comprises N-[1-(2, 3-dioleyloyx) propyl]-N—N—N-dimethyl ammonium chloride (DODMA), and the concentration of the quaternary amine cationic lipid present at about 5.0 molar percent;
and at least one single stranded oligonucleotide encapsulated within the lipid combination.

2. The nanoparticle of claim 1, wherein the tertiary amine-cationic lipid further comprises one or more of: lipids are chosen from 1,2-dioleoyl-3-dimethylammonium-propane (DODAP), 3β-[N—(N',N'-dimethylaminoethane)-carbamoyl]cholesterol hydrochloride (DC-CHOL), N,N-dimethylhexadecylamine (DMHDA), and combinations thereof.

3. The nanoparticle of claim 1, wherein the quaternary amine-cationic lipids are selected from 1,2-dioleoyl-3-trimethylammonium-propane (DOTAP), N-[1-(2, 3-dioleyloyx) propyl]-N—N—N-trimethyl ammonium chloride (DOTMA), dimethyldioctadecylammonium bromide (DDAB), or combinations thereof.

4. The nanoparticle of claim 1, wherein the encapsulated single stranded oligonucleotide comprises: antisense oligonucleotides, miRs, anti-miRs, or combinations thereof.

5. The nanoparticle of claim 1, further comprising a cationic polymer.

6. The nanoparticle of claim 5, wherein the cationic polymer is selected from the group consisting of: spermine, dispermine, dispermine, tetraspermine, oligospermine, thermine, spermidine, dispermidine, trispermidine, oligospermidine, putrescine, polylysine, polyarginine, a polyethylenimine of branched or linear type, and polyallylamine.

7. The nanoparticle of claim 1, further comprising a fusogenic peptide covalently bonded to, or conjugated to the lipids.

8. The nanoparticle of claim 1, wherein the encapsulation rate is 20% or higher.

9. The nanoparticle of claim 1, wherein the nanoparticle has a diameter under 300 nm.

10. A nanoparticle having a diameter of less than 300 nm; comprising: the nanoparticle of claim 1; and
at least one peptide mixed with, covalently attached or conjugated to the lipids.

11. The nanoparticle of claim 10, wherein the peptide is selected from gramicidin A, B, C, D, or S; JTS-1; proteinase K (PrK); trichorovin-Xlla; rabies virus glycoprotein; interleukin-1 β; HIV-Tat; herpes simplex virus VP22 protein; and combinations thereof.

12. The nanoparticle of claim 10, wherein the peptide comprises an antibiotic.

13. The nanoparticle of claim 12, wherein the antibiotic is selected from gramicidin A, B, C, D, or S.

14. The nanoparticle of claim 10, wherein the peptide consists essentially of a lipidated JTS-1 fusogenic peptide.

15. The nanoparticle of claim 14, wherein the lipidated JTS-1 fusogenic peptide is present at about 0 to about 30 molar percent of the total formulation.

16. The nanoparticle of claim 10, further comprising proteinase K.

17. The nanoparticle of claim 16, wherein the proteinase K is present at about 0 to about 30 molar percent of the total formulation.

18. The nanoparticle of claim 10, wherein the encapsulated single stranded oligonucleotide comprises: antisense oligonucleotides, miRs, anti-miRs, or combinations thereof.

19. The nanoparticle of claim 1, further comprising a hydrophilic polymer covalently bonded to the lipids, or conjugated to the lipids.

20. The nanoparticle of claim 19, wherein the hydrophilic polymer is selected from polysorbate 80, D-alpha-tocopheryl polyethylene glycol 1000 succinate (TPGS), mPEG-1,2-distearoyl-sn-glycero-3-phosphoethanolamine-N (DSPE), methoxypolyethylene glycol (PEG-DMG), dipalmitoyl-phosphatidlyethanolamine-PEG2000 (DPPE-PEG) or mPEG dimyristoylphosphatidylethanolamine (DMPE).

21. The nanoparticle of claim 20, wherein the hydrophilic polymer is present at a concentration less than about 10.0 molar percent.

22. The nanoparticle of claim 1, further comprising a ligand capable of binding to a target cell or a target molecule.

23. The nanoparticle of claim 22, wherein the ligand is an antibody or an antibody fragment.

24. The nanoparticle of claim 22, wherein the ligand is selected from cRGD, galatose-containing moieties, transferrin, folate, low density lipoprotein, or epidermal growth factors.

25. The nanoparticle of claim 1, wherein the nanoparticle further encapsulates an at least one additional therapeutic agent selected from: antineoplastic agents, anti-infective agents, local anesthetics, anti-allergics, antianemics, angiogenesis, inhibitors, beta-adrenergic blockers, calcium channel antagonists, anti-hypertensive agents, anti-depressants, anti-convulsants, anti-bacterial, anti-fungal, anti-viral, anti-rheumatics, anthelminithics, antiparasitic agents, corticosteroids, hormones, hormone antagonists, immunomodulators, neurotransmitter antagonists, anti-diabetic agents, anti-epileptics, anti-hemmorhagics, anti-hypertonics, antiglaucoma agents, immunomodulatory cytokines, sedatives, chemokines, vitamins, toxins, narcotics, imaging agents, and combinations thereof.

26. The nanoparticle of claim 25, wherein the encapsulated therapeutic agent comprises a nucleic acid therapeutic agent.

27. The nanoparticle of claim 26, wherein the nucleic acid therapeutic agent is selected from: pDNA, miRNA, anti-miRNA, antisense oligonucleotide (ASO), and combinations thereof.

28. The nanoparticle of claim 26, wherein the nucleic acid therapeutic agent is stabilized by modifications to substituent nucleic acid base units and/or by modifying the ribose 2' position or substituting phosphodiester linkers.

29. The nanoparticle of claim 1, wherein the lipid nanoparticle has a diameter under about 200 nm.

30. The nanoparticle of claim 19, wherein the hydrophilic polymer is bound to an external surface of the nanoparticle via direct connection or via a linker.

31. The nanoparticle of claim 11, wherein the nanoparticle has an encapsulation efficiency of the molecule of at least about 40%.

32. A pharmaceutical composition comprising the nanoparticle of claim 1, and a pharmaceutically acceptable excipient.

33. The pharmaceutical composition of claim 32, wherein the pharmaceutical composition is a tablet, an inhalant, or a suppository.

34. The pharmaceutical composition of claim 32, wherein the pharmaceutical composition is a sterile solution, a sterile suspension, or a lyophilized powder.

35. A composition comprising anti-miR-221 combined nanoparticle of claim 1.

36. A composition comprising anti-miR-155 combined with the nanoparticle of claim 1.

37. The composition of claim 36, wherein the lipid nanoparticle comprises Lac-GLN, wherein Lac-GLN comprises a lipophilic asialoglycoprotein receptor (ASGR) targeting ligand composed of lactobionic acid (LA), bearing a galactose moiety, and linked to a phospholipid.

38. The composition of claim 36, further including gramicidin A incorporated into the lipid nanoparticle.

39. The composition of claim 36, wherein the anti-miR-155 has the sequence: 5'-A*C*CCCUAUCACGAUU AGCAUU*A*A-3', SEQ ID NO. 6.

40. The composition of claim 39, wherein the sequence contains phosphorothioate linkages (*) and 2'-O-Methyl.

* * * * *

UNITED STATES PATENT AND TRADEMARK OFFICE
CERTIFICATE OF CORRECTION

PATENT NO. : 9,750,819 B2
APPLICATION NO. : 14/403313
DATED : September 5, 2017
INVENTOR(S) : Robert J. Lee Page 1 of 1

It is certified that error appears in the above-identified patent and that said Letters Patent is hereby corrected as shown below:

In the Specification

Column 1, Lines 16-19, please update the Statement Regarding Federally Sponsored Research as shown:
This invention was made with government support under grant number CA135243 awarded by the National Institutes of Health. The government has certain rights in the invention.

Signed and Sealed this
Twenty-first Day of July, 2020

Andrei Iancu
*Director of the United States Patent and Trademark Office*

SEQUENCE LISTING

```
<160> NUMBER OF SEQ ID NOS: 17

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccctgtggat gactgagtac ctg                                                   23

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccagcctccg ttatcctgg                                                        19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ccggcacctg cacacctgga                                                       20

<210> SEQ ID NO 4
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (1)..(23)
<223> OTHER INFORMATION: 2'-O-methyl-modified nucleotide
<220> FEATURE:
<221> NAME/KEY: misc_feature
<222> LOCATION: (19)..(23)
<223> OTHER INFORMATION: Phosphorothioate linkage
<220> FEATURE:
<221> NAME/KEY: misc_feature
<222> LOCATION: (23)..(23)
<223> OTHER INFORMATION: U-Chol

<400> SEQUENCE: 4
gaaacccagc agacaaugua gcu                                            23

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgtgcgagtg tctaacgg                                                  18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggatcagtc tttgggtc                                                  18

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgtcttcccc tccatcg                                                   17

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctcgttaatg tcacgcac                                                  18
```

```
<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cggagcacgg ggacgggtat c                                              21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagacgaagg ggaagacgca catc                                           24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaagaccgt ggacaagcac ag                                             22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgaacaagt tccgcagggt gc                                             22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aatggcactg accaaggctt c                                              21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgtggaggaa ctctgggaat gtg                                            23

<210> SEQ ID NO 15
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cccctggcca aggtcatcca tgacaacttt                                           30

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggccatgagg tccaccaccc tgttgctgta                                           30

<210> SEQ ID NO 17
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(3)
<223> OTHER INFORMATION: Phosphorothioate linkage
<220> FEATURE:
<221> NAME/KEY: misc_feature
<222> LOCATION: (21)..(23)
<223> OTHER INFORMATION: Phosphorothioate linkage

<400> SEQUENCE: 17
accccuauca cgauuagcau uaa                                                  23
```